(12) United States Patent
Gerald et al.

(10) Patent No.: US 6,709,831 B1
(45) Date of Patent: Mar. 23, 2004

(54) DNA ENCODING MAMMALIAN NEUROPEPTIDE FF (NPFF) RECEPTORS AND USES THEREOF

(75) Inventors: Christophe P. G. Gerald, Ridgewood, NJ (US); Kenneth A. Jones, Bergenfield, NJ (US); James A. Bonini, Oakland, NJ (US); Beth E. Borowsky, Montclair, NJ (US); Douglas A. Craig, Emerson, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/405,558

(22) Filed: Sep. 24, 1999

Related U.S. Application Data

(63) Continuation-in-part of application No. 09/255,368, filed on Feb. 22, 1999, now Pat. No. 6,262,246, which is a continuation-in-part of application No. 09/161,113, filed on Sep. 25, 1998, now abandoned.

(51) Int. Cl.[7] ............... G01N 33/566; C07K 14/00; C12N 15/12; C12N 15/63
(52) U.S. Cl. ............... 435/7.2; 435/325; 435/320.1; 435/69.1; 530/350
(58) Field of Search ............... 435/7.2, 320.1, 435/325, 69.1; 530/350

(56) References Cited

FOREIGN PATENT DOCUMENTS

| EP | 0884387 | 12/1998 |
|---|---|---|
| WO | 0000606 | 1/2000 |
| WO | 0029441 | 5/2000 |
| WO | 0031107 | 6/2000 |

OTHER PUBLICATIONS

Allard, et al., "Mechanisms Underlying the Cardiovascular Responses to Peripheral Administration of NPFF in the Rat", *J. Pharmacol. Exp. Ther.* 274(1): 577–583 (Jul. 1995).

Devillers, et al., "Characterization of a Potent Agonist for NPFF Receptors: Binding Study on Rat Spinal Cord Membranes" *Neuropharmacology* 33(5): 661–669 (May 1994).

Dupouy, et al., "Species Differences in the Localization of Neuropeptide FF Receptors in Rodent and Lagomorph Brain and Spinal Cord" *Peptides* 17(3): 399–405 (1996).

Knapp, et al., "Molecular Biology and Pharmacology of Cloned Opioid Receptors" *FASEB J.* 9(7): 516–525 (Apr. 1995).

Payza, et al., "Modulation of Neuropeptide FF Receptors by Guanine Nucleotides and Cations in Membranes of Rat Brain and Spinal Cord" *J. Neurochem.* 60(5): 1894–1899 (May 1993).

Expressed Sequence Tags Database Accession No. AA 449919, published Jun. 4, 1997 (Exhibit 3).

Expressed Sequence Tags Database Accession No. AA 449920, published Jun. 4, 1997 (Exhibit 4).

Cikoš, et al., "Sequence and Tissue Distribution of a Novel G–Protein–Coupled Receptor Expressed Prominently in Human Placenta," *Biochem. and Biophysical Res. Comm.*, Mar. 16, 1999, 256: 352–356 (Exhibit 5).

*Primary Examiner*—Yvonne Eyler
*Assistant Examiner*—Joseph F. Murphy
(74) *Attorney, Agent, or Firm*—John P. White; Cooper & Dunham LLP

(57) ABSTRACT

This invention provides isolated nucleic acids encoding mammalian NPFF receptors, purified mammalian NPFF receptors, vectors comprising nucleic acid encoding mammalian NPFF receptors, cells comprising such vectors, antibodies directed to mammalian NPFF receptors, nucleic acid probes useful for detecting nucleic acid encoding mammalian NPFF receptors, antisense oligonucleotides complementary to unique sequences of nucleic acid encoding mammalian NPFF receptors, transgenic, nonhuman animals which express DNA encoding normal or mutant mammalian NPFF receptors, methods of isolating mammalian NPFF receptors, methods of treating an abnormality that is linked to the activity of the mammalian NPFF receptors, as well as methods of determining binding of compounds to mammalian NPFF receptors, methods of identifying agonists and antagonists of NPFF receptors, and agonists and antagonists so identified.

23 Claims, 33 Drawing Sheets

Figure 1

```
   1  ACCCTTCCTGGGCCCCAGTCTACCCGCTTGAAGGTGCCGCGCTCCTTTGGAGAGTGTCCC     60
  61  GGAGCAGACAGTATGGAGGCGGAGCGGAGCCCTCCCAGCCCTCAACGGCAGCTGGCCCTGGGT    120
 121  CAGAACGGGAGTGATGTGGAGACCAGCAGCATGGCAACCAGCCTCACCTTCTCCTCTACTAC    180
 181  CAACACTCCTCCGGTGGCAGCCCCTGGTCTGCTTCATTGTGCTCAAGGAACCGGCACATGCGCACT    240
 241  TGCATGGTGGGCAACACATGTTTATCCTCAACCTGGCCGTCAGCGACCTGCTGGTGGGCATCTTCTGC    300
 301  GTCACCAACATGTTTATCCTCAACCTGGACAACCTTATCACTGGTTGGCCTTTTGACAACGCCACATGC    360
 361  ATGCCCACACAACCCTTGTGGACAACCTTATCACTGGTTGGCCTTTTGACAACGCCACATGGCC    420
 421  AAGATGAGCGGCTTGGTGCAGGGCATGTCCGTGTCTCTGCATCGGTTTTCACACTGGTGGCC    480
 481  ATCGCTGTGGAAAGGTTCACCATCGCGGTGATCTGGGCTCTGCACCCTTTCCGCGAGAAGCTGACCCTTCGG    540
 541  AAGGCGCTGTTCACCATCGCGGTGATCTGGGCTCTGCTCATCATGTGCTCGTAACCGC    600
 601  GCGGTCACTCTGACAGTCACCCGAGAGGAGCCTGGGGCCTGGTGCGCGATCACTTCATGGATGCTCTAGTGATGTAC    660
 661  TCCTACCCGCTCTACTCGTGCTGCGCACATCGTGCTGGGAGGCCATCTGGTGCCGCTCATCGTAGTGATGTAC    720
 721  ACCGCGGTGCATCGCGCGCAAGCTATGCCGCGACACTTCGCGCGCCTCCTGCGCGACACGGAGGAGGCG    780
 781  GTGCGCATCGCGCGAGGGTGGCCGCACTTCGCGCGCCTCCTGCGCGACACGGAGGAGGCG    840
 841  GTGGCCGAGGGTGGCCACTGCACGTTGTCCTGTGCCACTGCACACCTGCCGTGGTGCTGCTCATGGATG    900
 901  GTGGCGCTCTTTCTTCACGTTGTCCTGTGCCACTGCACCTGCCGTGGTGCTGCTCATCGAC    960
 961  TATGGGAGCTGAGCGAGCCCTTCTTCCACAGCTGCAACTGCAACCCCATCATCTACGCCTTCCCCTTGGCA   1020
1021  CACTGGCTGGCCCTTCTTCCACAGCTGCAACTGCAACCCCATCATCTACGCCTACTTCAACGAG   1080
1081  AACTTCCGCCGGCCGGCCTTCCAGCGCTGCCTTCCGCAGCTCTGCTGGCCTCCCCTGGGCC   1140
1141  GCCCACAAGCAAGCCCAGCCTACTCGGAGCGGCCCTGCCATCGAGTCTGGCCACGGGGTGGTG   1200
1201  GACGTGCAACCGACTCCGCCACTGCGCCTGCCATGCAGAGTCTGGCCCCAGCAGCGGGGTCCCA   1260
1261  GGGCCTGGCGTGCAACCACCACATGCCCCTGCAATGGCGTGTGCCCAGCAGCGATGGCCCGGGGAA   1320
1321  GGGCCAGGCTGCAACCACCACATGCCCCTCACCATCCCGGCCTGGAACATTTGAGGTGGTCCA   1380
1381  GAGAAGGGAGGGCCAGTAGTCCTGTGCCCC                                  1410
```

```
  1  M E A E P S Q P P N G S W P L G Q N G S    20
 21  D V E T S M A T S L T F S S Y Y Q H S S    40
                     I
 41  P V A A M F I A A Y V L I F L L C M V G    60
 61  N T L V C F I V L K N R H M R T V T N M    80
                                         II
 81  F I L N L A V S D L L V G I F C M P T T   100
101  L V D N L I T G W P F D N A T C K M S G   120
                       III
121  L V Q G M S V S A S V F T L V A I A V E   140
141  R F R C I V H P F R E K L T L R K A L F   160
                                       IV
161  T I A V I W A L A L L I M C P S A V T L   180
181  T V T R E E H H F M L D A R N R S Y P L   200
201  Y S C W E A W P E K G M R K V Y T A V L   220
                                       V
221  F A H I Y L V P L A L I V V M Y V R I A   240
241  R K L C Q A P G P A R D T E E A V A E G   260
261  G R T S R R R A R V V H M L V M V A L F   280
              VI
281  F T L S W L P L W V L L L L I D Y G E L   300
                                   VII
301  S E L Q L H L L S V Y A F P L A H W L A   320
321  F F H S S A N P I I Y G Y F N E N F R R   340
341  G F Q A A F R A Q L C W P P W A A H K Q   360
361  A Y S E R P N R L L R R R V V V D V Q P   380
381  S D S G L P S E S G P S S G V P G P G R   400
401  L P L R N G R V A H Q D G P G E G P G C   420
421  N H M P L T I P A W N I                   432
```

Figure 4

```
  1 GAGCCCTCCCAGCCTCCCAATCAGCAGTTGGCCCCTAAGTCAGAATGGGACTAACACTGAG   60
 61 GCCACCCCGGCTACAAACCTCACCTTCCTCCTCCTACTATCAGCACACCTCCCCTGTGGCG  120
121 GCCATGTTCATTGTGGCCTATGCGCTCATCTTCCTGCTCTGCATGGTGTGGGCAACACCCTG  180
181 GTCTGTTTCATCGTGCTCAA                                           200
```

```
1   MEAEPSQPPNGSWPLGQNGSDVETSMATSLTFSSYYQHSSPVAAMFIAAY   rNPFF1
    |||||||   ||||   |||..  - |:..  ||:||||||||||:||
1   ...EPSQPPNSSWPLSQNGTNTEATPATNLTFSSYYQHTSPVAAMFIVAY   hNPFF1

51  VLIFLLCMVGNTLVCFIVL   rNPFF1
    |||||||||||||||||||
48  ALIFLLCMVGNTLVCFIVL   hNPFF1
```

Figure 7

```
  1  GCCGACAGGGCTCGCCGGGAGAGGTTCATCATGAATGAGAAATGGGACACAAACTCTTCA   60
 61  GAAAACTGGCATCCCATCTGGAATCTGGAATGTCAATGACACAAGCATCATCTGTACTCAGATATT  120
121  AATATTACCTATGTGAACTACTATCTTCACCAGCCTCAAGTGGCAGCAATCTTCATTATT  180
181  TCCTACTTTCTGATCTTCTTTTTGTGCATGATGGGAAATCTCTTCATCTTAAACCTGGTTGCTTTATTGTA  240
241  ATGAGGAACAAACATATGCACACAGTCACTAATCTCTTCATCTTAAACCTGGCCATAAGT  300
301  GATTTACTAGTTGGCATATTCTGCATGCCTATAACACTGCTGGACAATATTATAGCAGGA  360
361  TGGCCATTTGGAAACACGATGTGCAAGATCAGTGGATTGGTCCAGGAATATCTGTCGCA  420
421  GCTTCAGTCTTTACGTTAGTTGCAATGCTGTAGATAGGTTCCAGTGTGTGGTCTACCCT  480
481  TTTAAACCAAAGCTCACTATCAAGACAGCGTTTGTCATTATTATGATCATCTGGGTCCTA  540
541  GCCATCACCATTATGTCTCCATCTGCAGTAATGTTACATGTCAAGAAGAAAATATTAC  600
601  CGAGTGAGACTCAACTCCCAGAATAAAACCAGTCCAGTCGTTGCCAACATCTACCTGGCT  660
661  CCAAATCAGGAGAAATGAGGAAGATCTCATCATGTATGGAAGGATTGGAATTTCACTCTTCAGGGCTGCA  720
721  CCCCTCTCCCTCATTGTCATCATGAACCAGGAGAAGAACCAGTGGTGTCCAGGAAGAAGCAG  780
781  GTTCCTCACACAGGCAGGAAGAAGAACCAGGAGCACGTGGTGTCCAGGAAGAAGCAG  840
841  AAGATCATTAAGATGCTCCTGACTGCCCTGCGTTTATTCTCTCCAAATGAACTGCAGATCATC  900
901  TGGACTCTAATGATGCTCTCAGATACGCTGACCTTTCCAAATGAACTGCAGATCATC  960
961  AACATCTACATCTACCCCTTTTGCAACGAGAATTTCCGCCGTGGTTTCCAAGAAGCTTTCCAGCTC 1020
1021 ATCATTATGTTTCTTCAACAGACAAGCAAGCAGTGCCTATGGAAGCTTATGCCCTAAAAGCTAAAAGCCAT 1080
1081 CAGCTCTCTGCCATAAACACATCTAATCAGCTTGTCCAGAATCTACATTTCAAAACCCTCATGGG 1140
1141 GTGTCATAAAACACATCTAATCAGCTTGTCCAGAATCTACATTTCAAAACCCTCATGGG 1200
1201 GAAACCTTGCTTTATAGGAAAAGTGCTGAAAAACCCCAACAGGAATTAGTGATGGAAGAA 1260
1261 TTAAAGAAACTACTAACAGCAGTGAGATTTAAAAGAGCTA                     1302
```

```
  1  M N E K W D T N S S E N W H P I W N V N   20
 21  D T K H H L Y S D I N I T Y V N Y Y L H   40
                              I
 41  Q P Q V A A I F I I S Y F L I F F L C M   60
 61  M G N T V V C F I V M R N K H M H T V T   80
                             II
 81  N L F I L N L A I S D L L V G I F C M P  100
101  I T L L D N I I A G W P F G N T M C K I  120
                             III
121  S G L V Q G I S V A A S V F T L V A I A  140
141  V D R F Q C V V Y P F K P K L T I K T A  160
                              IV
161  F V I I M I I W V L A I T I M S P S A V  180
181  M L H V Q E E K Y Y R V R L N S Q N K T  200
201  S P V Y W R E D W P N Q E M R K I Y T    220
                               V
221  T V L F A N I Y L A P L S L I V I M Y G  240
241  R I G I S L F R A A V P H T G R K N Q E  260
261  Q W H V V S R K K Q K I I K M L L I V A  280
                         VI
281  L L F I L S W L P L W T L M M L S D Y A  300
301  D L S P N E L Q I I N I Y I Y P F A H W  320
                                   VII
321  L A F G N S S V N P I I Y G F F N E N F  340
341  R R G F Q E A F Q L Q L C Q K R A K P M  360
361  E A Y A L K A K S H V L I N T S N Q L V  380
381  Q E S T F Q N P H G E T L L Y R K S A E  400
401  K P Q Q E L V M E E L K E T T N S S E I  420
```

Figure 10

```
rNPFF1    MEAEPSQPPNGSWPLGQNGSDVETSMAT..SLTFSSYYQHSSPVAAMFIA  48
          | .    ..|    | .| .  : .  .:|: .|| |   |||.||
hNPFF2    MNEKWDTNSSENWHPIWNVNDTKHHLYSDINITYVNYYLHQPQVAAIFII  50 rNPFF1    AYVLIFLLCMVGNTLVCFIVLKNRHMRTVTNMFILNLAVSDLLVGIFCMP  98
          .|  |||  |||.|||.!||||::|:|| ||||:|||||:||||||||||
hNPFF2    SYFLIFFLCMMGNTVVCFIVMRNKHMHTVTNLFILNLAISDLLVGIFCMP  100 rNPFF1    TTLVDNLITGWPFDNATCKMSGLVQGMSVSASVFTLVAIAVERFRCIVHP  148
          ||.||:| ||||  |   ||.||||||.||.||||||||||||:||.|:|:|
hNPFF2    TTLLDNIIAGWPFGNTMCKIGGLVQGISVAAGVFTLVAIAVDRFQCVVYP  150 rNPFF1    FREKLTLRKALFTIAVIWALALLIMCPSAVTLTVTREEHH.FMLDARNRS  197
          |: |||::  |   | :|| ||: ||  |||| | |  |.::    |...|:.
hNPFF2    FKPKLTIKTAFVIIMIIWVLAITIMSPSAVMLHVQEEKYYRVRLNSQNKT  200 rNPFF1    YPLYSCWEAWPEKGMRKVYTAVLFAHIYLVPLALIVVMYVRIARKLCQAP  247
          |.| | | || . |||:|| ||||.||| ||.|||:|| ||    | .|
hNPFF2    SPVYWCREDWPNQEMRKIYTTVLFANIYLAPLSLIVIMYGRIGISLFRAA  250 rNPFF1    GPARDTEEAVAEGGRTSRRRARVVHMLVMVALFFTLSWLPLWVLLLLIDY  297
           |   .    :   ||:: ::: ||..||| | |||||||| |::| ||
hNPFF2    VPHTGRKNQ.EQWHVVSRKKQKIIKMLLIVALLFILSWLPLWTLMMLSDY  299 rNPFF1    GELSELQLHLLSVYAFPLAHWLAFFHSSANPIIYGYFNENFRRGFQAAFR  347
          :||  :| ::..:| :| |||||| .|| ||||||:||||||||||| ||.
hNPFF2    ADLSPNELQIINIYIYPFAHWLAFGNSSVNPIIYGFFNENFRRGFQEAFQ  349 rNPFF1    AQLCWPPWAAHKQAYSERPNRLLRRVVVDVQPSDSGLP.SESGPSSGVP  396
          |||       .    ..|   || |    | |  | |.
hNPFF2    LQLCQKRAKPMEAYALKAKSHVLINTSNQLVQESTFQNPHGETLLYRKSA  399 rNPFF1    GPGRLPLRNGRVAHQDGPGEGPGCNHMPLTIPAWNI  432
          .  |  .    |
hNPFF2    EKPQQELVMEELKETTNSSEI................  420
```

Figure 11

```
   1 ATGGAGGGGGAGCCCTCCCAGCCTCCCAACAGCAGTTGGCCCCTAAGTCAGAATGGGACT     60
  61 AACACTGAGGCCACCCCGGCTACAAACCTCACCTTCTCTCCTACTATCAGCACACCTCC    120
 121 CCTGTGGCGGCCATGTTCATTGTGGCCTATGCCTCTTCCTGCTCTGCATGGTGGGC       180
 181 AACACCCTGGTCTGTGTTTCATCGTGCTCAAGAACCGGCACATGCATATCTGTCACCAACATG  240
 241 TTCATCCTCAACCTGCTGTCAGTGACCTGCTGGTGGGCATCTTCTGCATGCCCACCACC    300
 301 CTTGTGGACAACCTCATCACTGGGTGGCCCTTCGACAATGCCACATGCAAGATGAGCGGC    360
 361 TTGGTGCAGGGCATGTCTGTGTCGGCTTCCGTTTTCACACTGGTGGCCATTGCTGTGAA    420
 421 AGGTTCCGCTGCATCGTGCACCCTTTCCGCGCTGCTCATCATGTGTCCCTCGGCCGTCACGCTG  480
 481 ACCATCGCCGTCATCTGGGCCCTGCCCGTGTGTCATCATGGTGACGCCCGCAACCGCTCCTACCCTC  540
 541 ACCGTCACCCGTGAGGAGCACCACTTCATGTGACGCAGGTCATGCCGAGGTCTACACCACTGTGCTC  600
 601 TACTCCTGCTGGGAGGGCCTGGCCCGCGCTGGCCTCATCGTGGTCATGTACGCCCGCATCGCG     660
 661 TTCTCGCACATCTACCTGGCCCAGGCCCCCGGCCCCCGGAGGCTGCGAGAGCTGCGACCCGCGA  720
 721 CGCAAGCTCTGCCAGAGCGCGAGAGCGCGTGGTGCACATGCTGGTCATGTCTGGTGGCCTGTTCTTCACG  780
 781 GCATCGGCGCAGAGCGCGCTCGGGCCGCTCTGCGCGTGTGCACATGCTGCTGCTGCTCATCGACTACGGCCAGCTCAGCGCG  840
 841 CTGTCCTGGCTGCCGCTGCCGCTCTGCACGCCCTTCACCCCGCGTAGCAGCTACGGGCAGCTCAGCGCG  900
 901 CCGCAGCTGCACCTGGTCACCGTGACCTGCACGCCCTTCCCCCTTCGCGCACTGGCTGGCCTTCTTC  960
 961 AACAGCAGGCGCCAACCCATCATCTACGGCTACTTCAACGAGAACTTCCGCCGCGGCTTC   1020
1021 CAGGCCGCCTTCCGCGGCCCCGGGAGCCCACAAGGAGGCCTAC   1080
1081 TCCGAGCGGCCGGCGGGCTTCTGCACAGGCGGGTCTTCGTGGTGCGGCCCAGCGAC   1140
1141 TCCGGGCTGCCCTCTGAGTCGGGCCTAGCAGTGGGGCCCCCAGGCCCGGCCGCCCTCCCG   1200
1201 CTGCGGAATGGGCGGGTGCTCACCACGCGTTGCCCAGGGAAGGGCCTGGCCTGCTCCCAC   1260
1261 CTGCCCCTCACCATTCCAGCCTGGGATATCTGA     1293
```

```
  1  M E G E P S Q P P N S S W P L S Q N G T   20
 21  N T E A T P A T N L T F S S Y Y Q H T S   40
                      I
 41  P V A A M F I V A Y A L I F L L C M V G   60
 61  N T L V C F I V L K N R H M H T V T N M   80
                                        II
 81  F I L N L A V S D L L V G I F C M P T T  100
101  L V D N L I T G W P F D N A T C K M S G  120
          III
121  L V Q G M S V S A S V F T L V A I A V E  140
141  R F R C I V H P F R E K L T L R K A L V  160
                                       IV
161  T I A V I W A L A L L I M C P S A V T L  180
181  T V T R E E H H F M V D A R N R S Y P L  200
201  Y S C W E A W P E K G M R R V Y T T V L  220
                                   V
221  F S H I Y L A P L A L I V V M Y A R I A  240
241  R K L C Q A P G P A P G G E E A A D P R  260
                          VI
261  A S R R R A R V V H M L V M V A L F F T  280
281  L S W L P L W A L L L L I D Y G Q L S A  300
301  P Q L H L V T V Y A F P F A H W L A F F  320
                       VII
321  N S S A N P I I Y G Y F N E N F R R G F  340
341  Q A A F R A R L C P R P S G S H K E A Y  360
361  S E R P G G L L H R R V F V V V R P S D  380
381  S G L P S E S G P S S G A P R P G R L P  400
401  L R N G R V A H H G L P R E G P G C S H  420
421  L P L T I P A W D I                      430
```

Figure 14

```
hNPFF2    1 MNEKWDTNSSENWHPIWNVNDTKHHLYSDINITYVNYYLHQPQVAAIFII  50
            . :  .    |    . | |         |:|:  .|| |    |||.||:
hNPFF1    1 ..MEGEPSQPPNSSWPLSQNGTNTEATPATNLTFSSYYQHTSPVAAMFIV  48 hNPFF2   51 SYFLIFFLCMMGNTVVCFIVMRNKHMHTVTNLFILNLAISDLLVGIFCMP 100
            .i |||  |||.|||.|||||::|:|||||||:||||||:||||||||||
hNPFF1   49 AYALIFLLCMVGNTLVCFIVLKNRHMHTVTNMFILNLAVSDLLVGIFCMP  98 hNPFF2  101 ITLLDNIIAGWPFGNTMCKISGLVQGISVAASVFTLVAIAVDRFQCVVYP 150
            ||.||:| ||||  |  ||.||||||.||.|||||||||||||:||.|:|:|
hNPFF1   99 TTLVDNLITGWPFDNATCKMSGLVQGMSVSASVFTLVAIAVERFRCIVHP 148 hNPFF2  151 FKPKLTIKTAFVIIMIIWVLAITIMSPSAVMLHVQEEKYYRVRLNSQNKT 200
            |:  |||::  |  |  :|| ||: || |||| | |  |.::.   ....|:.
hNPFF1  149 FREKLTLRKALVTIAVIWALALLIMCPSAVTLTVTREEHH.FMVDARNRS 197 hNPFF2  201 SPVYWCREDWPNQEMRKIYTTVLFANIYLAPLSLIVIMYGRIGISLFRAA 250
            |.| | | ||  .  ||::|||||..||||||.|||:||  || |  | .|
hNPFF1  198 YPLYSCWEAWPEKGMRRVYTTVLFSHIYLAPLALIVVMYARIARKLCQAP 247 hNPFF2  251 VPHTGRKNQEQWHVVSRKKQKIIKMLLIVALLFILSWLPLWTLMMLSDYA 300
            | |.       ||:: :::  ||..||| | |||||||| |:::| ||
hNPFF1  248 GPAPGGEEAADPR.ASRRARVVHMLVMVALFFTLSWLPLWALLLLIDYG 296 hNPFF2  301 DLSPNELQIINIYIYPFAHWLAFGNSSVNPIIYGFFNENFRRGFQEAFQL 350
            ||  :|  ::  :|  :|||||||| |||  ||||||:|||||||||| ||.
hNPFF1  297 QLSAPQLHLVTVYAFPFAHWLAFFNSSANPIIYGYFNENFRRGFQAAFRA 346 hNPFF2  351 QLCQKRAKPMEAYALKAKSHVLINTSNQLVQESTFQNPHGETLLYRKSAE 400
            .|| |       |   :   |:.   .|   .      |.
hNPFF1  347 RLC.PRPSGSHKEAYSERPGGLLHRRVFVVVRPSDSGLPSESGPSSGAPR 395 hNPFF2  401 KPQQELVMEELKETTNSSEI*..............              420
            . |   .       |
hNPFF1  396 PGRLPLRNGRVAHHGLPREGPGCSHLPLTIPAWDI*              431
```

Figure 22A

```
1    AGCCTCTCCTTTGATAAGGTCCACCATGGGCAAGAGAGATGGGACTCAAACTCTTCAGGAAG    60
61   CTGGGATCACACATCTGGAGTGGCAATGACACAGCATCCTTGGTATTCAGATATCAACAT   120
121  CACATACATGAACTACTATCTCCACCAGCCCCACGTGACAGCTGTCTTCATTAGCTCCTA   180
181  CTTCCTGATCTTCTTCCTGTGCATGGGTGGGAAACACTGTCGTCGTTTGCTTTGTAATAAG   240
241  GAATAGGTACACATGCACACGGTCACTAATTTCTTCATCTTCAACCTCGCAATAAGTGACTT   300
301  ACTGGTTGGAATATTCTGCATGCCTATCACATTGCTGGACAACATCATAGCAGGATGGCC   360
361  GTTTGGAAGCAGCATGTGCAAGATCAGCGGGCTGGTTGCAAGGATATCGGTTGTGGTCTTC   420
421  TGTCTTCACCTTGGTTGCCATAGCCGTCAAGACAGCCTTTGTCATGATCGTGATCATCTGGGGCCAT   480
481  GCCCAAGCTCACTGTCAAGACAGCCTTTGTCATGATCGTGATCATCTGGGGCCTGGCCAT   540
541  CACCATTATGACCCCATCTGCAATCATGTTACATGTTACATGGAAGAAAATACTACCGTGT   600
601  GAGGCTCAGCTCCCCACAATAAAACCAGCACAGTCTACTGGTGTCGGGAGGATTGGCCAAA   660
```

Figure 22B

```
 661  CCAGGAAATGAGGAGGATCTACACCACCGTGCTCTTTGCCACTATCTACCTGGCTCCACT   720
 721  CTCCCTCATTGTTATCATGTATGCAAGGATTGGGGCTTCCCTCTTCAAGACCTCAGCACA   780
 781  CAGCACAGGTAAGCAGCGCCTGGAGCAGTGGCATGTATCCAAGAGAAACAGAAGGTCAT    840
 841  CAAGATGCTGCTGACTGTGGCCCTCCTTTCATCCTTTCCTGGCTTCCCCCTGTGGACTCT   900
 901  GATGATGCTCTCAGACTATGCTCACCTAACAAACTACGTGTCATCAATATTTA          960
 961  TGTCTACCCTTTTGCCCACTGGCTCGGCCCTTCTGCAATAGCAGTGTCAACCCCATCATTTA 1020
1021  TGGTTTCTTTAATGAAAATTTTCGCAGTGGTTTCCAAGATGCTTTCCAGTTCTGCCAAAA  1080
1081  GAAAGTCAAACCCCAGGAAGCCTATGGCCTAAGAGCTAAACGCAACCTGGACATAAACAC  1140
1141  ATCTGGCCTGTTGGTCCATGAACCTGCATCTCAAAACCCAAGTGGGGAAAACTTGGGATG  1200
1201  TAGAAAAGTGCAGACAATCCCACACAGGAATCCTTGATGGAGGAAACGGGAGAAGCTAC   1260
1261  CAACAGTACTGAGACTTAGAAAGATAGTATGCTATCCAATGTTATATAGCATACGAAGCC  1320
```

Figure 22C

1321 AACTCCGATGGCTG 1334

```
hNPFF2    1  MNEKWDTNSSENWHPIWNVNDTKHHLYSDINITYVNYYLHQPQVAAIFII   50
             : ||  ||  |  |   ||    | ||||||| |||| |||||  || |
rNPFF2    1  MGKRWDSNSSGSWDHIWSGNDTQHPWYSDINITYMNYYLHQPHVTAVFIS   50 hNPFF2   51  SYFLIFFLCMMGNTVVCFIVMRNKHMHTVTNLFILNLAISDLLVGIFCMP  100
             |||||||||| ||||||| |  |:| ||||||  |||||||||||||||
rNPFF2   51  SYFLIFFLCMVGNTVVCFVVRNRYMHTVTNFFIFNLAISDLLVGIFCMP  100 hNPFF2  101  ITLLDNIIAGWPFGNTMCKISGLVQGISVAASVFTLVAIAVDRFQCVVYP  150
             |||||||||||||| ||:|||||||||||||||||||||||||||:||||
rNPFF2  101  ITLLDNIIAGWPFGSSMCKISGLVQGISVAASVFTLVAIAVDRFRCVVYP  150 hNPFF2  151  FKPKLTIKTAFVIIMIIWVLAITIMSPSAVMLHVQEEKYYRVRLNSQNKT  200
             ||||||:|||| :|:|||:||||||:||| ||||||||||||||||| |:
rNPFF2  151  FKPKLTVKTAFVMIVIIWGLAITIMTPSAIMLHVQEEKYYRVRLSSHNKT  200 hNPFF2  201  SPVYWCREDWPNQEMRKIYTTVLFANIYLAPLSLIVIMYGRIGISLFRAA  250
             |:|||||||||||||| ||||||||| |||||||||||| ||:|| : |
rNPFF2  201  STVYWCREDWPNQEMRRIYTTVLFATIYLAPLSLIVIMYARIGASLFKTS  250
```

Figure 24B

```
hNPFF2  251  VPHTGRKNQEQWHVVSRKKQKIIKMLLIVALLFILSWLPLWTLMMLSDYA  300
              ||:. ||| |:||| |:::|||||:||||||||||||||||||||||||
rNPFF2  251  AHSTGKQRLEQWH.VSKKKQKVIKMLLTVALLFILSWLPLWTLMMLSDYA  299 hNPFF2  301  DLSPNELQIINIYIYPFAHWLAFGNSSVNPIIYGFFNENFRRGFQEAFQL  350
              |||||:|| :||||:|||||||| |||||||||||||||||:  :|:|
rNPFF2  300  DLSPNKLRVINIYVYPFAHWLAFCNSSVNPIIYGFFNENFRSGFQDAF..  347 hNPFF2  351  QLCQKRAKPMEAYALKAKSHVLINTSNQLVQESTFQNPHGETLLYRKSAE  400
              :|||:||||:||| |:::.. ||||:||.:|:|:|:|.|||:| |||:|
rNPFF2  348  QFCQKKVKPQEAYGLRAKRNLDINTSGLLVHEPASQNPSGENLGCRKSAD  397 hNPFF2  401  KPQQELVMEELKETTNSSEI                              420
              ||:|||:|||. |:|||:|
rNPFF2  398  NPTQESLMEETGEATNSTET                              417
```

Figure 25A

```
rNPFF1    1  MEAEPSQPPNGSWPLGQNGSDVETSMAT..SLTFSSYYQHSSPVAAMFIA  48
              |||  . .  .|.|   .||.  ..:. ..:|.||| :|||.||.|:.|||
rNPFF2    1  MGKRWDSNSSGSWDHIWSGNDTQHPWYSDINITYMNYYLHQPHVTAVFIS  50 rNPFF1   49  AYLIFLLCMVGNTLVCFIVLKNRHMRTVTNMFILNLAVSDLLVGIFCMP   98
             .|||.|||||||||.||.:::|||.|:||..||.||:||||||||||||
rNPFF2   51  SYFLIFFLCMVGNTVVCFVVIRNRYMHTVTNFFIFNLAISDLLVGIFCMP  100 rNPFF1   99  TTLVDNLITGWPFDNATCKMSGLVQGMSVSASVFTLVAIAVERFRCIVHP  148
             :|.:|||:..|||...:|.|||||||:||.|||||||||||:|||:|:|
rNPFF2  101  ITLLDNIIAGWPFGSSMCKISGLVQGISVAASVFTLVAIAVDRFRCVVYP  150 rNPFF1  149  FREKLTLRKALFTIAVIWALALLIMCPSAVTLTVTREEHH.FMLDARNRS  197
             |::|||.||||.|:||:|.||:|||||||:|||||||.: :..||:|:|
rNPFF2  151  FKPKLTVKTAFVMIVIIWGLAITIMTPSAIMLHVQEEKYYRVRLSSHNKT  200 rNPFF1  198  YPLYSCWEAWPEKGMRKVYTAVLFAHIYLVPLALIVVMYVRIARKLCQAP  247
             ||.| |.|:|::|.|.||::||.||:||:|||:||:||:|||||.|:..
rNPFF2  201  STVYWCREDWPNQEMRRIYTTVLFATIYLAPLSLIVIMYARIGASLFKT.  249
```

Figure 25B

```
rNPFF1  248 GPARDTEEAVAEGGRTSRRRARVVHMLVMVALFFTLSWLPLWVLLLLIDY 297
                :||   .| :||.  ||| ||:|||||||||||| |::||
rNPFF2  250 .SAHSTGKQRLEQWHVSKKKQKVIKMLLTVALLFILSWLPLWTLMMLSDY 298 rNPFF1  298 GELSELQLHLLLSVYAFPPLAHWLAFFHSSANPIIYGYFNENFRRGFQAAFR 347
             :|| . : :| ||  ||| ||||| | :||||||| |||||||| ||
rNPFF2  299 ADLSPNKLRVINIYVYPFAHWLAFCNSSVNPIIYGFFNENFRSGFQDAF. 347 rNPFF1  348 AQLCWPPWAAHKQAYSERPNRLLRRRVVVDVQPSDSGL.....PSESGPSS 393
                  .:        ||  |  | |       |:  . |
rNPFF2  348 .QFCQKK.VKPQEAYGLRAKRNL.......DI..NTSGLLVHEPASQNPSG 387 rNPFF1  394 GVPGPGRLPLRNGRVAHQDGPGEGPGCNHMPLTIPAWNI 432
              :     :               ==
rNPFF2  388 ENLGCRKSADNPTQESLMEETGEATNSTET......... 417
```

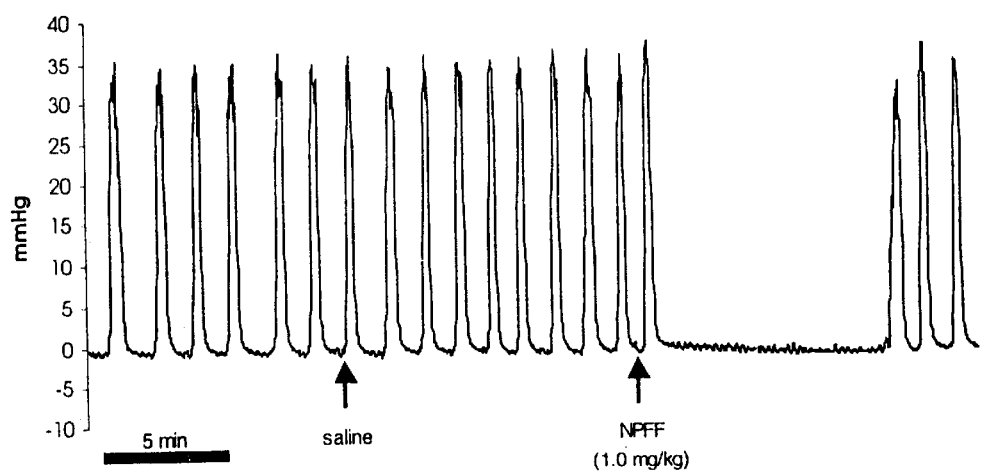

DNA ENCODING MAMMALIAN NEUROPEPTIDE FF (NPFF) RECEPTORS AND USES THEREOF

This application is a continuation-in-part of U.S. Ser. No. 09/255,368, filed Feb. 22, 1999, now U.S. Pat. No. 6,262, 246 which is a continuation-in-part of U.S. Ser. No. 09/161, 113, filed Sep. 25, 1998, now abandoned the contents of both of which are hereby incorporated by reference into the subject application.

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the art to which this invention pertains.

Neuroregulators comprise a diverse group of natural products that subserve or modulate communication in the nervous system. They include, but are not limited to, neuropeptides, amino acids, biogenic amines, lipids and lipid metabolites, and other metabolic byproducts. Many of these neuroregulator substances interact with specific cell surface receptors which transduce signals from the outside to the inside of the cell. G-protein coupled receptors (GPCRs) represent a major class of cell surface receptors with which many neurotransmitters interact to mediate their effects. GPCRs are predicted to have seven membrane-spanning domains and are coupled to their effectors via G-proteins linking receptor activation with intracellular biochemical sequelae such as stimulation of adenylyl cyclase. Neuropeptide FF (NPFF) is an octapeptide isolated from bovine brain in 1985 by Yang and coworkers (1) using antibodies to the molluscan neuropeptide FMRFamide (FMRFa). FMRFamide-like immunoreactivity was observed in rat brain, spinal cord, and pituitary, suggesting the existence of mammalian homologs of the FMRFa family of invertebrate peptides. The isolation of NPFF, named for its N- and C-terminal phenylalanines (also called F8Famide) and a second mammalian peptide, NPAF (also called A18Famide), confirmed the existence of mammalian family of peptides sharing C-terminal sequence homology with FMRFa (1). Molecular cloning has revealed that NPFF and NPAF are encoded by the same gene and cleaved from a common precursor protein (2). Studies of the localization, radioligand binding, and function of NPFF-like peptides (see below) indicate they are neuromodulatory peptides whose effects are likely to be mediated by G protein-coupled receptors (for review, see 3).

NPFF, also called "morphine modulating peptide", is an endogenous modulator of opioid systems with effects on morphine analgesia, tolerance, and withdrawal (for review see 3,4). NPFF appears to represent an endogenous "anti-opioid" system in the CNS acting at specific, high-affinity receptors distinct from opiate receptors (5,6). Endogenous NPFF has been suggested to play a role in morphine tolerance: agonists of NPFF precipitate "morphine abstinence syndrome" (i.e. symptoms of morphine withdrawal) in morphine-dependent animals (7,8), while antagonists and anti-NPFF IgG restore morphine sensitivity and ameliorate symptoms of withdrawal (9–12). NPFF antagonists potentially could be useful as therapeutic agents to prevent the development of morphine tolerance, and to treat opiate addiction. NPFF has also been suggested to participate in the regulation of pain threshold, showing both "anti-opiate" effects and analgesic effects depending on test system and route of administration (for review, see 4). As an anti-opiate, NPFF has been shown to inhibit morphine- and stress-induced analgesia (1, 13, 14, 15), whereas anti-NPFF IgG (which blocks the biological activity of NPFF) potentiates these two phenomena (16, 17). An NPFF antagonist may be clinically useful in potentiating the analgesic effects of morphine, allowing use of lower doses without the development of tolerance. NPFF agonists may also exhibit analgesic activity in some model systems (14, 18, 19). The analgesia elicited by NPFF is typically sensitive to naloxone, indicating that it is mediated by release of endogenous opioid peptides (19, 20). The interaction of NPFF and opioid systems in regulating pain pathways is thus complex and may involve multiple mechanisms and sites of action. NPFF has additional biological activities in accord with its pattern of expression in the nervous system.

NPFF peptide localization in rat CNS was examined using specific antibodies ((21–23); see also (3)). The highest levels of NPFF are found in spinal cord and posterior pituitary; pituitary NPFF is believed to originate in the hypothalamus. In the brain, immunoreactive cell bodies are found in two major cell groups: medial hypothalamus (between dorsomedial and ventromedial) and nucleus of the solitary tract. Immunoreactive fibers are observed in lateral septal nucleus, amygdala, hypothalamus, nucleus of solitary tract, ventral medulla, trigeminal complex, and dorsal horn of spinal cord. This localization pattern is consistent with a role for NPFF in sensory processing and modulation of opioid systems. In addition, its presence in the hypothalamus and other limbic structures could subserve roles in the regulation of appetitive and affective states. In the periphery, NPFF-like immunoreactivity (as well as NPFF binding) has been observed in the heart (24). In addition, injection of NPFF raises blood pressure in rats (24, 25). These observations, combined with the colocalization of NPFF with catecholaminergic neurons in the nucleus of the solitary tract (26), suggest that NPFF is involved in central and peripheral cardiovascular regulation.

The ability of NPFF peptides to modulate the opioid system raised the possibility that NPFF interacts directly with opiate receptors. However, radioligand binding assays using a tyrosine-substituted NPFF analog [$^{125}$I]Y8Fa demonstrate that NPFF acts through specific high affinity binding sites distinct from opiate receptors (27–30) that are sensitive to inhibition by guanine nucleotides (31). The latter observation indicates that NPFF receptors are likely to belong to the superfamily of G protein-coupled receptors which share common structural motifs. However, no reports of cloning NPFF receptors have appeared as yet.

To address the issue of potential degradation of the peptide radioligand, a more stable NPFF analog (called (1DMe)Y8Fa(18)) has also been radioiodinated and the binding characterized in spinal cord membranes (32). The binding was saturable and of high affinity; inhibition of binding with unlabeled NPFF analogs yielded Ki values of 0.16 nM and 0.29 nM for (1DMe)Y8Fa and NPFF, respectively, with a Bmax=15 fmol/mg protein. No inhibition by various opioid compounds (naloxone, morphine, enkephalins, dynorphins, etc.) or other peptides (NPY, SP, CGRP, for examples) was observed at a concentration of 10 μM, confirming the specificity of NPFF receptors. Interestingly, the related molluscan peptide FMRFa inhibited the binding of [$^{125}$I](1DMe)Y8Fa with a Ki=30 nM. The effectiveness of FMRFamide and the C-terminal fragment NPFF(6–8) at NPFF receptors suggests an important role for the common C-terminus. Full activity is retained by NPFF (3–8); it has been suggested that although the C-terminus is important for receptor recognition, the N-terminus is necessary for formation of a high-affinity conformation (33).

Allard et al. (29) examined the distribution of NPFF binding sites in rat brain and spinal cord using [$^{125}$I]Y8Fa ([$^{125}$I]YLFQPQRFamide) The highest densities were observed in the external layers of dorsal horn of spinal cord, several brainstem nuclei, the suprachiasmatic nucleus, restricted nuclei of the thalamus, and the presubiculum of the hippocampus. Lower densities were seen in central gray, reticular formation, ventral tegmental area, lateral and anterior hypothalamus, medial preoptic area, lateral septum, the head of caudate-putamen and cingulate cortex. No binding was observed in cortex, nucleus accumbens, hippocampus (except in presubiculum) or cerebellum. The localization of NPFF binding sites is in good agreement with the location of the peptide itself, consistent with the binding sites mediating the biological actions of NPFF in these tissues (29, 34, 35). Less is known about the signal transduction pathways activated by NPFF receptors; NPFF was shown to activate adenylyl cyclase in mouse olfactory bulb membranes (36) but no other reports of functional coupling via G proteins have appeared.

Until now, no direct evidence for NPFF receptor subtypes has been reported in mammals. Recent physiological data suggest complex (biphasic) effects on nociception and antiopiate activity of NPFF (for review, see (3, 4)) that could possibly signal the presence of multiple subtypes. Short term ICV injection of NPFF causes a hyperesthesic effect followed by long lasting analgesic effect. Intrathecal NPFF and FMRFa both produce long-lasting analgesia, but subeffective doses caused different modulatory effects on morphine-induced analgesia (F8Fa potentiated, FMRFa decreased). The analgesic effects of NPFF are sensitive to naloxone, suggesting that NPFF receptors may have distinct presynaptic (possibly associated with increase release of opioids) and postsynaptic (anti-opiate) effects mediated by multiple receptors. Little is known of the biological effects of A18Famide, which shares its C-terminal 4 amino acids with NPFF, but the existence of a family of related peptides often is predictive of multiple receptor subtypes.

No nonpeptide agonists or antagonists of NPFF are available, but several useful peptidic analogs have been developed that exhibit increased agonist stability or antagonist activity. For example, desamino Y8Fa (daY8Fa) can antagonize the behavioral effects of NPFF and restore morphine-sensitivity (tail-flick analgesia) to morphine-tolerant rats at lower doses, although at higher doses it can act as NPFF agonist (10)(see also (3)). (1DMe)Y8Fa, in which L-Phe$^1$ is replaced by D-Tyr and the second peptidic bond is N-methylated, has been shown to inhibit morphine-induced analgesia (18), and has higher affinity and stability than Y8Fa: (1DMe)Y8Fa was 90% stable after 150 min. incubation with rat spinal cord membranes compared with Y8Fa, which was fully degraded after 30 minutes. These analogs may be useful in predicting the effects of agonist or antagonist drugs that would act at NPFF receptors.

Despite the numerous studies linking NPFF with analgesia (for review, see (4)), only recently has NPFF been observed to play a role in animal models of chronic pain. For example, NPFF has recently been shown to be involved in inflammatory pain (37) and neuropathic pain (38). Importantly, NPFF was shown to attenuate the allodynia associated with neuropathic pain, suggesting that it may be clinically useful in treating this condition. In addition to its potential therapeutic roles in the treatment of pain and morphine tolerance ((4) and above), NPFF and related peptides have a number of other biological activities that may be therapeutically relevant. NPFF and FMRFamide have been shown to reduce deprivation- and morphine-induced feeding in rats (39–41), indicating that NPFF receptors may be important targets in the treatment of eating disorders. FMRFamide has also been shown to produce antipsychotic (42) and antianxiety (85)effects in rats, indicating that NPFF receptors may be valuable targets for the treatment of psychosis and anxiety. There is evidence for a role of NPFF in learning and memory. Kavaliers and Colwell (79) have shown that i.c.v. administered NPFF has a biphasic effect of spatial learning in mice: low doses improve and high doses impair learning. This suggests the possibility that different NPFF receptor subtypes may have opposite roles in some types of learning behavior. NPFF is known to have indirect effects on water and electrolyte balance. Arima et al. (86) have shown that NPFF will reduce increase in vasopressin release produced by salt loading or hypovolemia. Additionally, NPFF may be involved in the control of plasma aldosterone levels (87). These observations raise the possibility that agents targeting NPFF receptors may be of value in the treatment of diuresis or in the treatment of cardiovascular conditions such as hypertension and congestive heart failure. Drugs acting at NPFF receptors may be of value in the treatment of diabetes, since NPFF and A-18-Famide have been shown to produce significant inhibition of glucose- and arginine-induced insulin release in rats (88). Several investigators have reported effects of NPFF and analogs on intestinal motility in mice (89) and guinea pigs (90, 91). When administered to isolated preparations of guinea pig ileum, the actions of NPFF oppose those of opioids. Conversely, i.c.v. administration of NPFF in mice produces effects similar to those of morphine on intestinal motility. Together, these results indicate a complex modulatory role for NPFF in intestinal motility, but indicate that NPFF receptors are potential targets for drugs to treat GI motility disorders, including irritable bowel syndrome. NPFF has been shown to precipitate nicotine abstinence syndrome in a rodent model (43). These authors have raised the possibility that nicotine dependence may be attenuated by measures which inactivate NPFF. Thus, NPFF receptor antagonists may be of use for this purpose. Finally, NPFF is known to elicit two acute cardiovascular responses when administered peripherally: elevation of blood pressure and heart rate (24, 25). These actions may be mediated peripherally, centrally, or both. Thus, agents acting at NPFF receptors may be of value in the treatment of hypertension (also see above) or hypotension. The cloning of NPFF receptors will facilitate the elucidation of the roles of NPFF and related peptides in these and other important biological functions.

Described herein is the isolation and characterization of a new family of neuropeptide FF (NPFF) receptors, referred to herein as the NPFF receptors. Cloned NPFF receptors will serve as invaluable tools for drug design for pathophysiological conditions such as memory loss, affective disorders, schizophrenia, pain, hypertension, locomotor problems, circadian rhythm disorders, eating/body weight disorders, sexual/reproductive disorders, nasal congestion, diarrhea, gastrointestinal, and cardiovascular disorders. Also described herein are experimental data which indicate that NPFF receptors will be useful targets for the design of drugs to treat disorders of the lower urinary tract, including incontinence and bladder instability.

SUMMARY OF THE INVENTION

This invention provides an isolated nucleic acid encoding a mammalian NPFF receptor.

This invention provides a nucleic acid encoding a mammalian NPFF receptor, wherein the nucleic acid (a) hybridizes to a nucleic acid having the defined sequence shown in FIG. 1 (SEQ ID NO: 1) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement. This invention further provides a nucleic acid encoding a mammalian NPFF receptor, wherein the nucleic acid (a) hybridizes to a nucleic acid having the defined sequence shown in FIG. 4 (SEQ ID NO: 3) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement. This invention also provides a nucleic acid encoding a mammalian NPFF receptor, wherein the nucleic acid (a) hybridizes to a nucleic acid having the defined sequence shown in FIG. 7 (SEQ ID NO: 5) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

This invention further provides a nucleic acid encoding a mammalian NPFF receptor, wherein the nucleic acid (a) hybridizes to a nucleic acid having the defined sequence shown in FIG. 11 (SEQ ID NO: 7) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

This invention further provides a nucleic acid encoding a mammalian NPFF receptor, wherein the nucleic acid (a) hybridizes to a nucleic acid having the defined sequence shown in FIGS. 22A–C (SEQ ID NO: 43) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

This invention also provides a purified mammalian NPFF receptor protein.

This invention further provides a vector comprising a nucleic acid encoding a mammalian NPFF receptor, particularly a vector adapted for expression of the mammalian NPFF receptor in mammalian or non-mammalian cells.

This invention provides a plasmid designated pEXJ-rNPFF1 (ATCC Accession No. 203184). This invention also provides a plasmid designated pWE15-hNPFF1 (ATCC Accession No. 203183). This invention further provides a plasmid designated pCDNA3.1-hNPFF2b (ATCC Accession No. 203255). This invention still further provides a plasmid designated pcDNA3.1-hNPFF1 (ATCC Accession No. 203605). This invention still further provides a plasmid designated pcDNA3.1-rNPFF2-f (ATCC Patent Deposit Designation No. PTA-535).

This invention additionally provides a cell comprising a vector which in turn comprises a nucleic acid encoding a mammalian NPFF receptor as well as a membrane preparation isolated from such a cell.

Moreover, this invention provides a nucleic acid probe comprising at least 15 nucleotides, which probe specifically hybridizes with a nucleic acid encoding a mammalian NPFF receptor, wherein the probe has a unique sequence corresponding to a sequence present within one of the two strands of the nucleic acid encoding the mammalian NPFF1 receptor and contained in plasmid pEXJ-rNPFF1 (ATCC Accession No. 203184), plasmid pWE15-hNPFF1 (ATCC Accession No. 203183), plasmid pCDNA3.1-hNPFF2b (ATCC Accession No. 203255), plasmid pcDNA3.1-hNPFF1 (ATCC Accession No. 203605) or plasmid pcDNA3.1-rNPFF2-f (ATCC Patent Deposit Designation No. PTA-535).

This invention further provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 1 (SEQ ID NO: 1) or (b) the reverse complement thereto.

This invention further provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 4 (SEQ ID NO: 3) or (b) the reverse complement thereto.

This invention further provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 7 (SEQ ID NO: 5) or (b) the reverse complement thereto.

This invention further provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 11 (SEQ ID NO: 7) or (b) the reverse complement thereto.

This invention further provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIGS. 22A–C (SEQ ID NO: 43) or (b) the reverse complement thereto.

This invention still further provides an antisense oligonucleotide having a sequence capable of specifically hybridizing to RNA encoding the mammalian NPFF receptor, so as to prevent translation of the RNA. This invention also provides an antisense oligonucleotide having a sequence capable of specifically hybridizing to genomic DNA encoding a mammalian NPFF receptor, so as to prevent transcription thereof.

This invention further provides an antibody capable of binding to a mammalian NPFF receptor. This invention also provides an agent capable of competitively inhibiting the binding of the antibody to a mammalian NPFF receptor.

In addition, this invention provides a pharmaceutical composition comprising (a) an amount of the oligonucleotide described above capable of passing through a cell membrane and effective to reduce expression of a mammalian NPFF receptor and (b) a pharmaceutically acceptable carrier capable of passing through the cell membrane.

This invention also provides a transgenic, nonhuman mammal expressing DNA encoding a mammalian NPFF receptor. This invention also provides a transgenic, nonhuman mammal comprising a homologous recombination knockout of the native mammalian NPFF receptor. This invention further provides a transgenic, nonhuman mammal whose genome comprises antisense DNA complementary to the DNA encoding a mammalian NPFF receptor so placed within the genome as to be transcribed into antisense mRNA which is complementary to mRNA encoding the mammalian NPFF receptor and which hybridizes to mRNA encoding the mammalian NPFF receptor, thereby reducing its translation.

This invention provides a process for identifying a chemical compound which specifically binds to a mammalian NPFF receptor which comprises contacting cells containing DNA encoding and expressing on their cell surface the mammalian NPFF receptor, wherein such cells do not normally express the mammalian NPFF receptor, with the compound under conditions suitable for binding, and detecting specific binding of the chemical compound to the mammalian NPFF receptor.

This invention further provides a process for identifying a chemical compound which specifically binds to a mammalian NPFF receptor which comprises contacting a membrane preparation from cells transfected with DNA encoding and expressing on their cell surface the mammalian NPFF receptor, wherein such cells do not normally express the mammalian NPFF receptor, with the compound under conditions suitable for binding, and detecting specific binding of the chemical compound to the mammalian NPFF receptor.

This invention provides a process involving competitive binding for identifying a chemical compound which specifically binds to a mammalian NPFF receptor which comprises separately contacting cells expressing on their cell surface the mammalian NPFF receptor, wherein such cells do not normally express the mammalian NPFF receptor, with both the chemical compound and a second chemical compound known to bind to the receptor, and with only the second chemical compound, under conditions suitable for binding of both compounds, and detecting specific binding of the chemical compound to the mammalian NPFF receptor, a decrease in the binding of the second chemical compound to the mammalian NPFF receptor in the presence of the chemical compound indicating that the chemical compound binds to the mammalian NPFF receptor.

This invention further provides a process involving competitive binding for identifying a chemical compound which specifically binds to a mammalian NPFF receptor which comprises separately contacting a membrane fraction from cells expressing on their cell surface the mammalian NPFF receptor, wherein such cells do not normally express the mammalian NPFF receptor, with both the chemical compound and a second chemical compound known to bind to the receptor, and with only the second chemical compound, under conditions suitable for binding of both compounds, and detecting specific binding of the chemical compound to the mammalian NPFF receptor, a decrease in the binding of the second chemical compound to the mammalian NPFF receptor in the presence of the chemical compound indicating that the chemical compound binds to the mammalian NPFF receptor.

This invention provides a method of screening a plurality of chemical compounds not known to bind to a mammalian NPFF receptor to identify a compound which specifically binds to the mammalian NPFF receptor, which comprises (a) contacting cells transfected with and expressing DNA encoding the mammalian NPFF receptor with a compound known to bind specifically to the mammalian NPFF receptor; (b) contacting the preparation of step (a) with the plurality of compounds not known to bind specifically to the mammalian NPFF receptor, under conditions permitting binding of compounds known to bind to the mammalian NPFF receptor; (c) determining whether the binding of the compound known to bind to the mammalian NPFF receptor is reduced in the presence of any compound within the plurality of compounds, relative to the binding of the compound in the absence of the plurality of compounds; and if so (d) separately determining the binding to the mammalian NPFF receptor of compounds included in the plurality of compounds, so as to thereby identify the compound which specifically binds to the mammalian NPFF receptor.

This invention also provides a method of screening a plurality of chemical compounds not known to bind to a mammalian NPFF receptor to identify a compound which specifically binds to the mammalian NPFF receptor, which comprises (a) contacting a membrane preparation from cells transfected with and expressing DNA encoding a mammalian NPFF receptor with a compound known to bind to the mammalian NPFF receptor; (b) determining whether the binding of a compound known to bind to the mammalian NPFF receptor is reduced in the presence of any compound within the plurality of compounds, relative to the binding of the compound in the absence of the plurality of compounds; and if so (c) separately determining the binding to the mammalian NPFF receptor of compounds included in the plurality of compounds, so as to thereby identify the compound which specifically binds to the mammalian NPFF receptor.

Still further, this invention provides a method of detecting expression of a mammalian NPFF receptor by detecting the presence of mRNA coding for the mammalian NPFF receptor which comprises obtaining total mRNA from the cell and contacting the mRNA so obtained with a nucleic acid probe under hybridizing conditions, detecting the presence of mRNA hybridizing to the probe, and thereby detecting the expression of the mammalian NPFF receptor by the cell.

This invention provides a method of detecting the presence of a mammalian NPFF receptor on the surface of a cell which comprises contacting the cell with an antibody under conditions permitting binding of the antibody to the receptor, detecting the presence of the antibody bound to the cell, and thereby detecting the presence of the mammalian NPFF receptor on the surface of the cell.

This invention provides a method of determining the physiological effects of varying levels of activity of mammalian NPFF receptors which comprises producing a transgenic, nonhuman mammal whose levels of mammalian NPFF receptor activity are varied by use of an inducible promoter which regulates mammalian NPFF receptor expression.

This invention also provides a method of determining the physiological effects of varying levels of activity of mammalian NPFF receptors which comprises producing a panel of transgenic, nonhuman mammals each expressing a different amount of mammalian NPFF receptor.

This invention further provides a method for identifying an antagonist capable of alleviating an abnormality wherein the abnormality is alleviated by decreasing the activity of a mammalian NPFF receptor comprising administering a compound to a transgenic, nonhuman mammal as described above and determining whether the compound alleviates the physical and behavioral abnormalities displayed by the transgenic, nonhuman mammal as a result of overactivity of a mammalian NPFF receptor, the alleviation of the abnormality identifying the compound as an antagonist. This invention also provides an antagonist identified by this method. This invention still further provides a pharmaceutical composition comprising an antagonist identified by this method and a pharmaceutically acceptable carrier.

This invention additionally provides a method of treating an abnormality in a subject wherein the abnormality is alleviated by decreasing the activity of a mammalian NPFF receptor which comprises administering to the subject an effective amount of the preceding pharmaceutical composition containing a mammalian NPFF receptor antagonist, thereby treating the abnormality.

This invention also provides a method for identifying an agonist capable of alleviating an abnormality in a subject wherein the abnormality is alleviated by increasing the activity of a mammalian NPFF receptor comprising administering a compound to a transgenic, nonhuman mammal, and determining whether the compound alleviates the physical and behavioral abnormalities displayed by the transgenic, nonhuman mammal, the alleviation of the abnormality identifying the compound as an agonist. This invention also provides an agonist identified by this method. This invention further provides a pharmaceutical composition comprising an agonist identified by this method and a pharmaceutically acceptable carrier. This invention provides a method of treating an abnormality in a subject wherein the abnormality is alleviated by increasing the activity of a mammalian NPFF receptor which comprises administering to the subject an effective amount of the preceding pharmaceutical composition containing a mammalian NPFF receptor agonist, thereby treating the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian NPFF receptor and labeled with a detectable marker; (e) detecting labeled bands which have hybridized to the DNA encoding a mammalian NPFF receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same.

This invention provides a method of preparing a purified mammalian NPFF receptor which comprises: (a) culturing cells which express the mammalian NPFF receptor; (b) recovering the mammalian NPFF receptor from the cells; and (c) purifying the mammalian NPFF receptor so recovered.

This invention provides a method of preparing a purified mammalian NPFF receptor which comprises: (a) inserting a nucleic acid encoding the mammalian NPFF receptor into a suitable vector; (b) introducing the resulting vector into a suitable host cell; (c) placing the resulting cell in suitable condition permitting the production of the mammalian NPFF receptor; (d) recovering the mammalian NPFF receptor produced by the resulting cell; and (e) isolating and/or purifying the mammalian NPFF receptor so recovered.

This invention provides a process for determining whether a chemical compound is a mammalian NPFF receptor agonist which comprises contacting cells transfected with and expressing DNA encoding the mammalian NPFF receptor with the compound under conditions permitting the activation of the mammalian NPFF receptor, and detecting an increase in mammalian NPFF receptor activity, so as to thereby determine whether the compound is a mammalian NPFF receptor agonist. This invention also provides a pharmaceutical composition which comprises an amount of a mammalian NPFF receptor agonist determined by this process effective to increase activity of a mammalian NPFF receptor and a pharmaceutically acceptable carrier.

This invention provides a process for determining whether a chemical compound is a mammalian NPFF receptor antagonist which comprises contacting cells transfected with and expressing DNA encoding the mammalian NPFF receptor with the compound in the presence of a known mammalian NPFF receptor agonist, under conditions permitting the activation of the mammalian NPFF receptor, and detecting a decrease in mammalian NPFF receptor activity, so as to thereby determine whether the compound is a mammalian NPFF receptor antagonist. This invention also provides a pharmaceutical composition which comprises an amount of a mammalian NPFF receptor antagonist determined by this process effective to reduce activity of a mammalian NPFF receptor and a pharmaceutically acceptable carrier.

This invention provides a process for determining whether a chemical compound specifically binds to and activates a mammalian NPFF receptor, which comprises contacting cells producing a second messenger response and expressing on their cell surface the mammalian NPFF receptor, wherein such cells do not normally express the mammalian NPFF receptor, with the chemical compound under conditions suitable for activation of the mammalian NPFF receptor, and measuring the second messenger response in the presence and in the absence of the chemical compound, a change in the second messenger response in the presence of the chemical compound indicating that the compound activates the mammalian NPFF receptor. This invention also provides a compound determined by this process. This invention further provides a pharmaceutical composition which comprises an amount of the compound (a NPFF receptor agonist) determined by this process effective to increase activity of a mammalian NPFF receptor and a pharmaceutically acceptable carrier.

This invention provides a process for determining whether a chemical compound specifically binds to and inhibits activation of a mammalian NPFF receptor, which comprises separately contacting cells producing a second messenger response and expressing on their cell surface the mammalian NPFF receptor, wherein such cells do not normally express the mammalian NPFF receptor, with both the chemical compound and a second chemical compound known to activate the mammalian NPFF receptor, and with only the second chemical compound, under conditions suitable for activation of the mammalian NPFF receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian NPFF receptor. This invention also provides a compound determined by this process. This invention further provides a pharmaceutical composition which comprises an amount of the compound (a mammalian NPFF receptor antagonist) determined by this effective to reduce activity of a mammalian NPFF receptor and a pharmaceutically acceptable carrier.

This invention provides a method of screening a plurality of chemical compounds not known to activate a mammalian NPFF receptor to identify a compound which activates the mammalian NPFF receptor which comprises: (a) contacting cells transfected with and expressing the mammalian NPFF receptor with the plurality of compounds not known to activate the mammalian NPFF receptor, under conditions permitting activation of the mammalian NPFF receptor; (b) determining whether the activity of the mammalian NPFF receptor is increased in the presence of the compounds; and if so (c) separately determining whether the activation of the mammalian NPFF receptor is increased by each compound included in the plurality of compounds, so as to thereby identify the compound which activates the mammalian NPFF receptor. This invention also provides a compound identified by this method. This invention further provides a pharmaceutical composition which comprises an amount of the compound (a mammalian NPFF receptor agonist) identified by this method effective to increase activity of a mammalian NPFF receptor and a pharmaceutically acceptable carrier.

This invention provides a method of screening a plurality of chemical compounds not known to inhibit the activation of a mammalian NPFF receptor to identify a compound which inhibits the activation of the mammalian NPFF receptor, which comprises: (a) contacting cells transfected with and expressing the mammalian NPFF receptor with the plurality of compounds in the presence of a known mammalian NPFF receptor agonist, under conditions permitting activation of the mammalian NPFF receptor; (b) determining whether the activation of the mammalian NPFF receptor is reduced in the presence of the plurality of compounds, relative to the activation of the mammalian NPFF receptor in the absence of the plurality of compounds; and if so (c) separately determining the inhibition of activation of the mammalian NPFF receptor for each compound included in the plurality of compounds, so as to thereby identify the compound which inhibits the activation of the mammalian NPFF receptor. This invention also provides a compound identified by this method. This invention further provides a pharmaceutical composition which comprises an amount of the compound (a mammalian NPFF receptor antagonist) identified by this process effective to decrease activity of a mammalian NPFF receptor and a pharmaceutically acceptable carrier.

This invention provides a method of treating an abnormality in a subject wherein the abnormality is alleviated by increasing the activity of a mammalian NPFF receptor which comprises administering to the subject an amount of a compound which is a mammalian NPFF receptor agonist effective to treat the abnormality.

This invention provides a method of treating an abnormality in a subject wherein the abnormality is alleviated by decreasing the activity of a mammalian NPFF receptor which comprises administering to the subject an amount of a compound which is a mammalian NPFF receptor antagonist effective to treat the abnormality.

This invention provides a process for making a composition of matter which specifically binds to a mammalian NPFF receptor which comprises identifying a chemical compound using any of the processes described herein for identifying a compound which binds to and/or activates or inhibits activation of a mammalian NPFF receptor and then synthesizing the chemical compound or a novel structural and functional analog or homolog thereof. This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of a mammalian NPFF receptor or a novel structural and functional analog or homolog thereof.

BRIEF DESCRIPTION OF THE FIGURES

FIG. 1

Nucleotide sequence encoding a rat neuropeptide FF receptor (NPFF1)(SEQ ID NO: 1). In addition, partial 5' and 3' untranslated sequences are shown. In FIG. 1, two start (ATG) codons (at positions 73–75 and 148–150) and the stop (TAG) codon (at positions 1369–1371) are underlined.

FIG. 2

Deduced amino acid sequence (SEQ ID NO: 2) of the rat neuropeptide FF receptor (NPFF1) encoded by the nucleotide sequence shown FIGS. 1 (SEQ ID NO: 1).

FIG. 3

Deduced amino acid sequence for rat NPFF1 (SEQ ID NO: 2). Seven solid lines designated I–VII located above portions of the sequence indicate the seven putative transmembrane (TM) spanning regions.

FIG. 4

Partial coding sequence of human neuropeptide FF receptor (NPFF1)(SEQ ID NO: 3).

FIG. 5

Partial deduced amino acid sequence of the human neuropeptide FF (NPFF1) receptor (SEQ ID NO: 4) encoded by the partial nucleotide sequence of FIG. 3.

FIG. 6

Partial amino acid alignment of rat and human NPFF1. Vertical lines represent identical residues and dots represent similar residues.

FIG. 7

Nucleotide sequence of hNPFF2b (SEQ ID NO: 5). The initiating methionine and the stop codon are underlined.

FIG. 8

Deduced amino acid sequence of human NPFF2b (hNPFF2) (SEQ ID NO: 6) encoded by the nucleotide sequence shown in FIG. 7.

FIG. 9

Deduced amino acid sequence for human hNPFF2 (SEQ ID NO: 6), with potential transmembrane domains underlined.

FIG. 10

Amino acid alignment of rat NPFF1 and human NPFF2. Vertical lines represent identical residues and dots represent similar residues.

Figure Legends

FIG. 11

Nucleotide sequence of a human neuropeptide FF receptor (NPFF1)(SEQ ID NO: 7). The initiating methionine (at positions 1–3) and the stop codon (at positions 1291–1293) are underlined.

FIG. 12

Deduced amino acid sequence of the human neuropeptide FF receptor (NPFF1)(SEQ ID NO: 8).

FIG. 13

Deduced amino acid sequence for human NPFF1 (SEQ ID NO: 8). Seven solid lines designated I–VII indicate the seven putative transmembrane (TM) spanning regions.

FIG. 14

Amino acid alignment of the human NPFF1 and human NPFF2 receptors. Vertical lines represent identical residues and dots represent similar residues.

FIG. 15A–15C

Electrophysiological responses to NPFF and related peptides from voltage clamped oocytes expressing NPFF1 and chimeric G-protein.

FIGS. 16A–16C

Figure 16A:
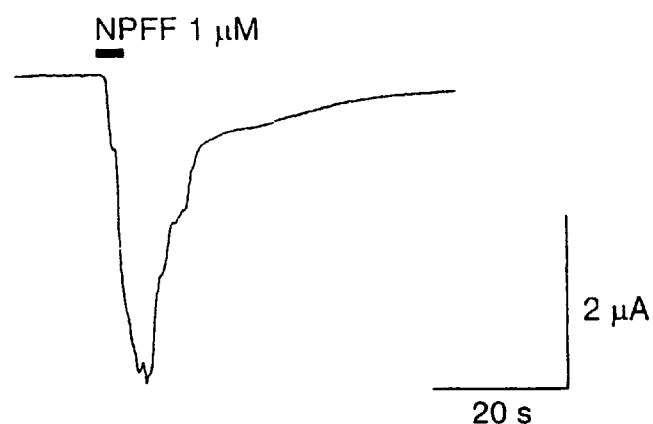
Figure 16B:
Figure 16C:
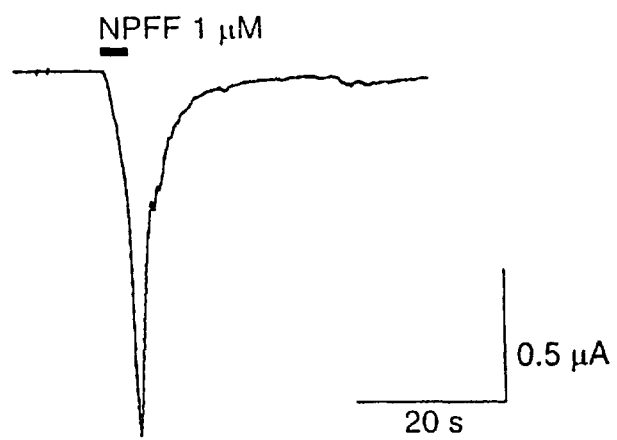

Electrophysiological responses in voltage-clamped oocytes expressing NPFF2 mRNA. FIG. 16A: Oocyte injected with NPFF2 mRNA (from ligation PCR) generates an inward current in response to NPFF at 1 μM. FIG. 16B: In a different oocyte, no response is observed when challenged with a mixture of galanin, NPY, orexin A and neurokinin A, each at 1 μM. A subsequent application of NPFF elicits a response. FIG. 16C: Oocyte injected with NPFF2 mRNA (from BO89) generates an inward current in response to NPFF at 1 μM. Oocytes were clamped at a holding potential of –80 mV.

Figure 17A:
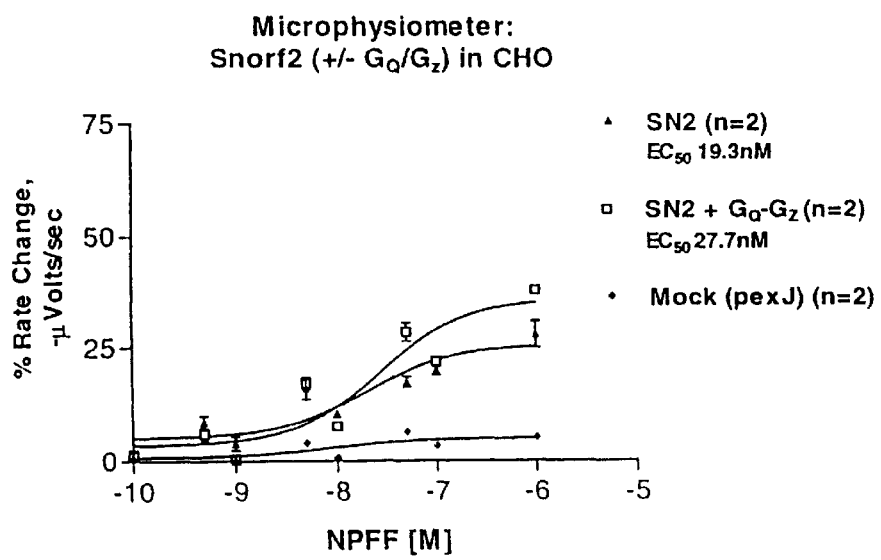
Figure 17B:
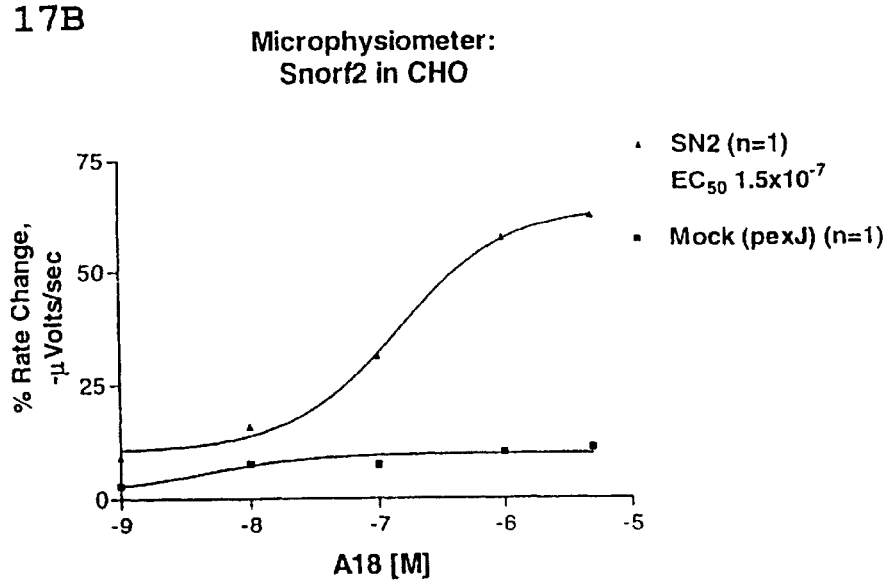

FIGS. 17A and 17B

Microphysiometric response of CHO cells transiently transfected with either NPFF1 (SN2) alone or NPFF1 accompanied by Gq/Gz. FIG. 17A: Cells expressing either NPFF1 alone or NPFF1+Gq/Gz produced a dose-dependent response to NPFF with an EC50 value of 19.3 nM and 27.7 nM respectively. Mock control cells transfected with empty vector produced little if any response to NPFF even at the highest concentrations used. FIG. 17B: Cells expressing NPFF1 alone produced a dose-dependent response to A-18-F-amide with an EC50 value of 150 nM. In both FIGS. 17A and 17B control cells mock transfected with empty vector produced little if any response to drug even at the highest concentrations used. Responses are reported as percentage increase in the acidification rate as observed just prior to drug challenge (immediate prior basal rate).

Figure 18A:
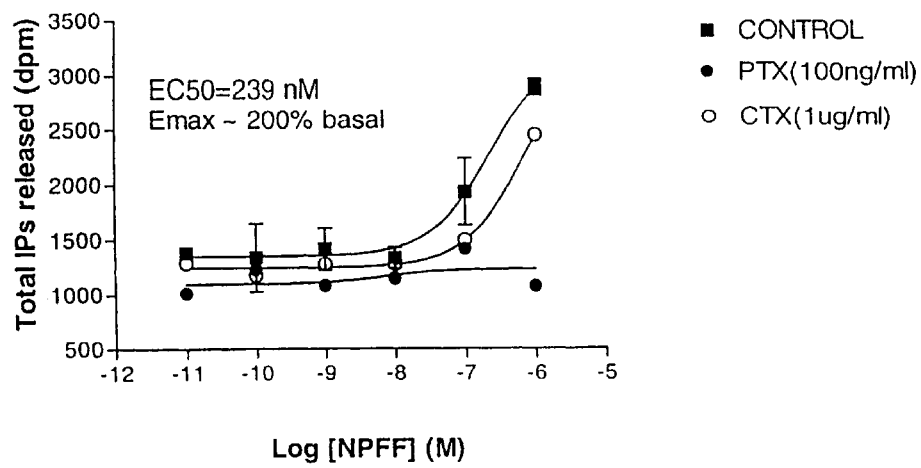
Figure 18B:
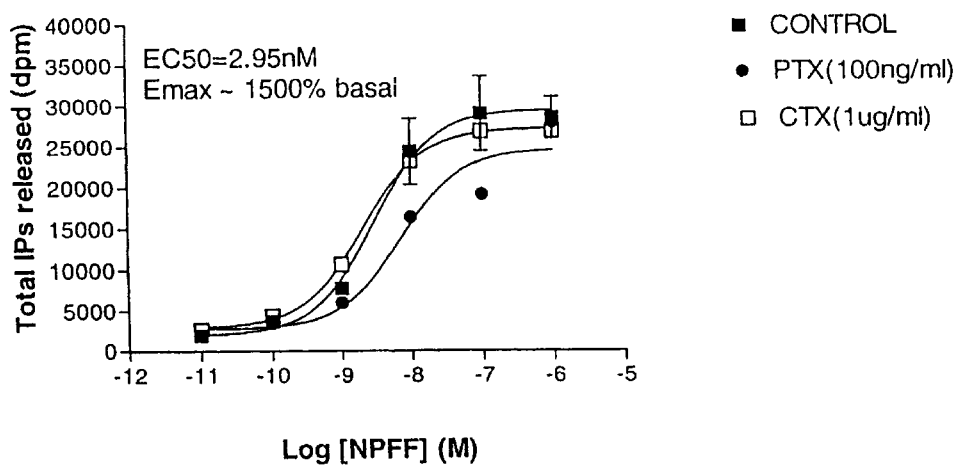

FIGS. 18A and 18B

NPFF stimulation of Inositol phosphate release in NPFF-1 transfected Cos-7 cells. FIG. 18A: Cos-7 cells were transiently transfected with NPFF-1 receptor cDNA. FIG. 18B: Cos-7 cells were transiently co-transfected with cDNAs for the NPFF-1 receptor and the Gq/Gz chimera. The accumulation of total inositol phosphate release was measured by prelabelling cells with [$^3$H]myoinositol (2 μCi/ml) overnight. Cells were washed to remove unincorporated radioactivity and resuspended in medium containing 10 mM LiCl. [$^3$H] myoinositol labeled cells were incubated with appropriate drugs for 1 hr at 37° C. The reaction was stopped by addition of 5% TCA and IPs were isolated by ion exchange chromatography (Berridge et al., 1982). Columns were washed with water and total [$^3$H] inositol phosphates were then eluted with 1M ammonium formate/0.1 M formic acid. Radioactivity in the final fraction was measured by liquid scintillation spectroscopy. Cells were either treated with vehicle (water, control) or cholera toxin (CTX; 1 μg/ml) or pertussis toxin (PTX, 100 ng/ml) overnight. Data are from one experiment representative of at least one other.

FIG. 19

RT-PCR was performed as described on a panel of mRNA extracted from rat tissue as indicated at the bottom of the gel. After amplification, PCR reactions were size fractionated on 10% polyacrylamide gels, and stained with SYBR Green I. Images were analyzed using a Molecular Dynamics Storm 860 workstation. The amplified band corresponding to NPFF1 (490 base pairs) is indicated (arrow). RT-PCR indicates a broad distribution of mRNA encoding NPFF1 with highest concentrations found in nervous system structures.

FIG. 20

Autoradiograph demonstrating hybridization of radiolabeled rat NPFF1 probe to RNA extracted from rat tissue in a solution hybridization/nuclease protection assay using $^{32}$P labeled riboprobe. 2μg of RNA was used in each assay. The single band (arrow) represents mRNA coding for the NPFF1 receptors extracted from the indicated tissue. Highest levels of mRNA coding for NPFF1 are found in: hypothalamus and pituitary gland. The smaller bands representing NPFF1 mRNA from the pituitary, adrenal gland, and ovary (double arrow) may indicate a splice variant present in this tissue. Integrity of RNA was assessed using hybridization to mRNA coding for GAPDH (not shown).

FIG. 21

RT-PCR was performed as described on a panel of mRNA extracted from tissue as indicated at the bottom of the gel. After amplification, PCR reactions were size fractionated on 10% polyacrylamide gels, and stained with SYBR Green I. Images were analyzed using a Molecular Dynamics Storm 860 workstation. The amplified band corresponding to NPFF2 receptors (approximately 325 base pairs) is indicated (arrow). RT-PCR indicates a broad distribution of mRNA encoding NPFF2 receptors. The only tissue containing mRNA coding for NPFF2 receptors were HeLa cells and Jurkat cells.

FIGS. 22A–22C

Nucleotide sequence encoding a rat neuropeptide FF receptor (NPFF2). In addition, partial 5' and 3' untranslated sequences are shown. Two start (ATG) codons (at positions 26–28 and 128–130) and the stop (TAG) codon (at positions 1277–1279) are underlined.

Figure 23A:
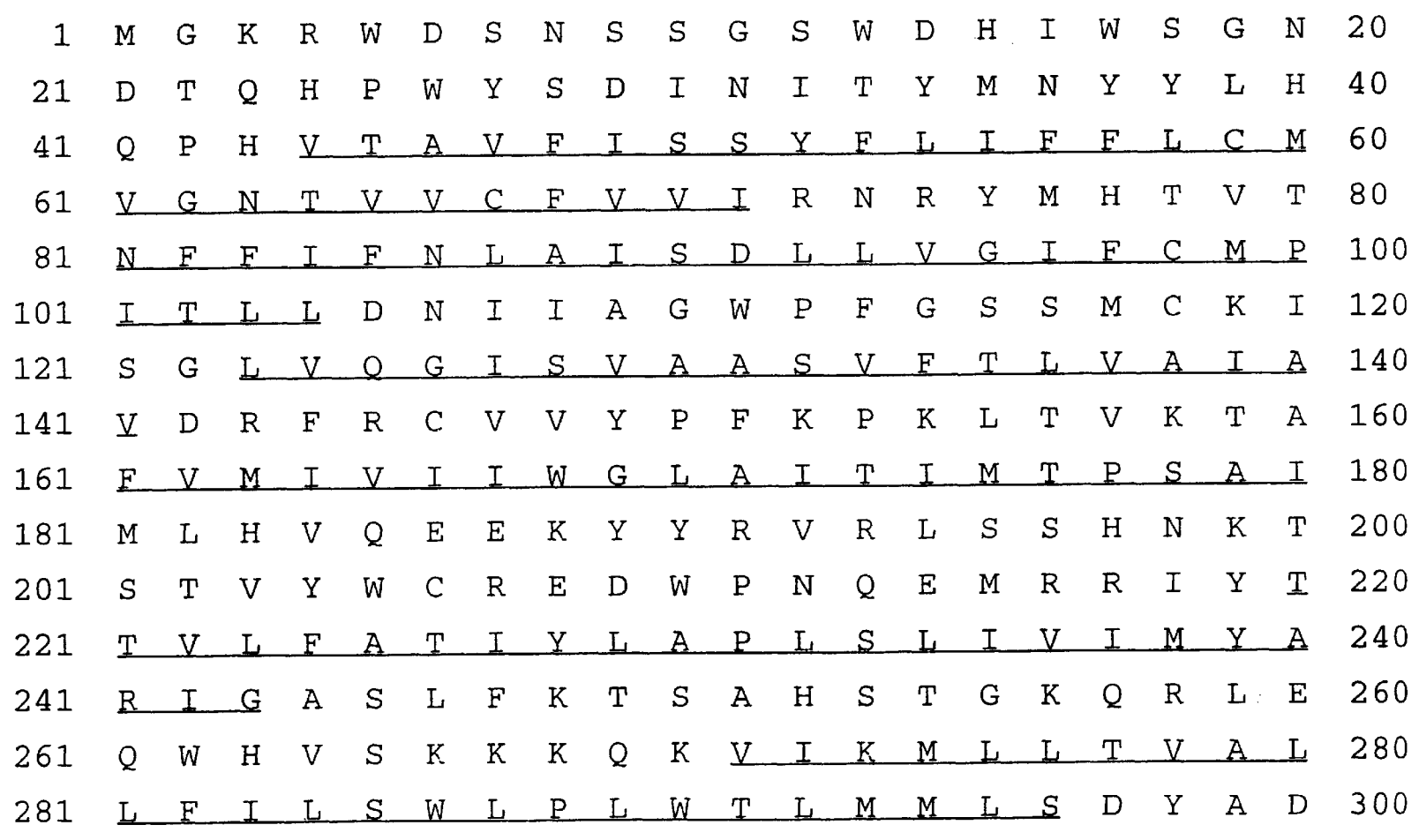
Figure 23B:
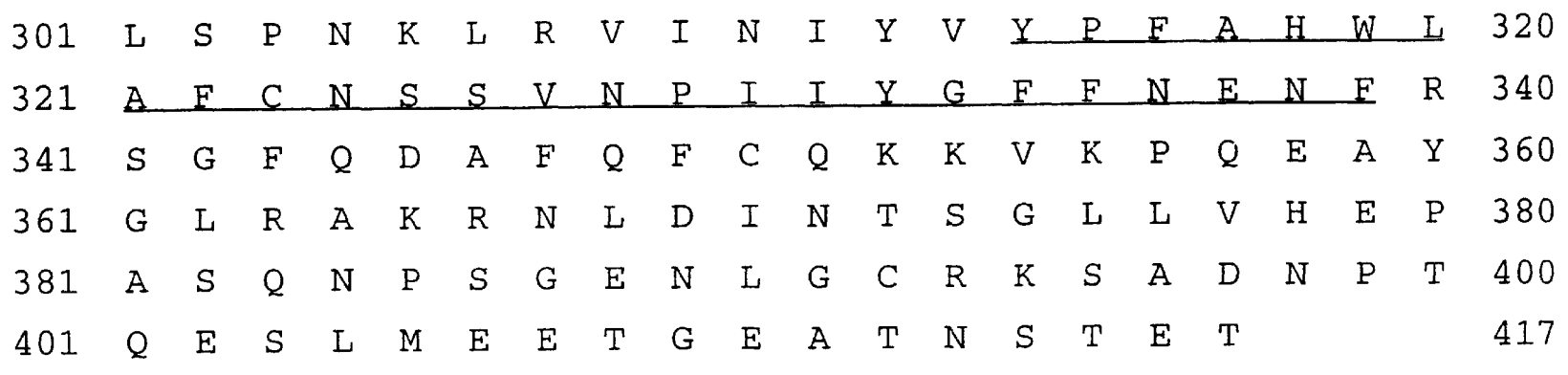

FIGS. 23A and 23B

Deduced amino acid sequence of the rat neuropeptide FF receptor (NPFF2) encoded by the nucleotide sequence shown in FIGS. 22A–22C. Seven putative transmembrane spanning regions are indicated by underlining.

FIGS. 24A and 24B

Amino acid alignment of human NPFF2 and rat NPFF2. Vertical lines represent identical residues and dots represent similar residues.

FIGS. 25A and 25B

Amino acid alignment of rat NPFF1 and rat NPFF2. Vertical lines represent identical residues and dots represent similar residues.

FIG. 26

Inhibition of distension-induced rhythmic contractions of the bladder in an anesthetized rat by NPFF (1.0 mg/kg) administered intravenously.

FIG. 27

Effect of saline, frog pancreatic polypeptide (fPP), and increasing concentrations of NPFF on the disappearance time of the bladder contractions in the distension-induced rhythmic contraction model of micturition in anesthetized rats. Presented are the mean values ± sem from experiments on "n" different rats.

FIG. 28

Inhibition of distension-induced rhythmic contractions of the bladder in an anesthetized rat by frog Pancreatic Polypeptide (fPP) (0.3 mg/kg) administered intravenously.

DETAILED DESCRIPTION OF THE INVENTION

Throughout this application, the following standard abbreviations are used to indicate specific nucleotide bases:

| | |
|---|---|
| A = | adenine |
| G = | guanine |
| C = | cytosine |
| T = | thymine |
| U = | uracil |
| M = | adenine or cytosine |
| R = | adenine or guanine |
| W = | adenine, thymine, or uracil |
| S = | cytosine or guanine |
| Y = | cytosine, thymine, or uracil |
| K = | guanine, thymine, or uracil |
| V = | adenine, cytosine, or guanine (not thymine or uracil |
| H = | adenine, cytosine, thymine, or uracil (not guanine) |
| D = | adenine, guanine, thymine, or uracil (not cytosine) |
| B = | cytosine, guanine, thymine, or uracil (not adenine) |
| N = | adenine, cytosine, guanine, thymine, or uracil (or other modified base such as inosine) |
| I = | inosine |

Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

The activity of a G-protein coupled receptor such as the polypeptides disclosed herein may be measured using any of a variety of functional assays in which activation of the receptor in question results in an observable change in the level of some second messenger system, including, but not limited to, adenylate cyclase, calcium mobilization, arachidonic acid release, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an oocyte expression system.

It is possible that the mammalian NPFF receptor genes contain introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns et al., 1996 (82); Chu et al., 1996 (83)). Such variants may exhibit pharmacologic properties differing from the polypeptide encoded by the original gene.

This invention provides splice variants of the mammalian NPFF receptors disclosed herein. This invention further provides for alternate translation initiation sites and alternately spliced or edited variants of nucleic acids encoding the mammalian NPFF receptors of this invention.

The nucleic acids of the subject invention also include nucleic acid analogs of the rat and human NPFF receptor genes, wherein the rat NPFF1 receptor gene comprises the nucleic acid sequence shown in FIG. 1 or contained in plasmid pEXJ-rNPFF1 (ATCC Accession No. 203184); the human NPFF1 receptor gene comprises the nucleic acid shown in FIG. 4 and contained in plasmid pWE15-hNPFF1 (ATCC Accession No. 203183); the human NPFF2 receptor gene comprises the nucleic acid shown in FIG. 7 and contained in plasmid pCDNA3.1-hNPFF2b (ATCC Accession No.203255); the human NPFF1 receptor gene comprises the nucleic acid shown in FIG. 11 and contained in plasmid pcDNA3.1-hNPFF1 (ATCC Accession No. 203605); or the rat NPFF2 receptor gene comprises the nucleic acid shown in FIGS. 22A–22C and contained in plasmid pcDNA3.1-rNPFF2-f (ATCC Patent Deposit Designation No. PTA-535). Nucleic acid analogs of the rat and human NPFF receptor genes differ from the rat and human NPFF receptor genes described herein in terms of the identity or location of one or more nucleic acid bases (deletion analogs containing less than all of the nucleic acid bases shown in FIGS. 1, 4, 7, 11 or 22A–C or contained in plasmids pEXJ-rNPFF1, pWE15-hNPFF1, pCDNA3.1-hNPFF2b, pcDNA3.1-hNPFF1, or pcDNA3.1-rNPFF2-f respectively, substitution analogs wherein one or more nucleic acid bases shown in FIGS. 1, 4, 7, 11 or 22A–C or contained in plasmids pEXJ-rNPFF1, pWE15-hNPFF1, pCDNA3.1-hNPFF2b, pcDNA3.1-hNPFF1, or pcDNA3.1-rNPFF2-f respectively, are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 1, 4, 7, 11 or 22A–C or contained in plasmids pEXJ-rNPFF1, pWE15-hNPFF1, pCDNA3.1-hNPFF2b, pcDNA3.1-hNPFF1, or pcDNA3.1-rNPFF2-f respectively. In one embodiment of the present invention, the nucleic acid analog encodes a protein which has an amino acid sequence identical to that shown in FIGS. 2, 5 8, 12 or 23A–B or encoded by the nucleic acid sequence contained in plasmids pEXJ-rNPFF1, pWE15-hNPFF1, pCDNA3.1-hNPFF2b, pcDNA3.1-hNPFF1, or pcDNA3.1-rNPFF2-f respectively. In another embodiment, the nucleic acid analog encodes a protein having an amino acid sequence which differs from the amino acid sequences shown in FIGS. 2, 5, 8, 12 or 23A–B or encoded by the nucleic acid contained in plasmids pEXJ-rNPFF1, pWE15-hNPFF1, pCDNA3.1-hNPFF2b, pcDNA3.1-hNPFF1 or pCDNA3.1-rNPFF2-f respectively. In a further embodiment, the protein encoded by the nucleic acid analog has a function which is the same as the function of the receptor proteins having the amino acid sequence shown in FIGS. 2, 5, 8, 12 or 23A–B. In another embodiment, the function of the protein encoded by the nucleic acid analog differs from the function of the receptor protein having the amino acid sequence shown in FIGS. 2, 5, 8, 12 or 23A–B. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA. Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 1 (SEQ ID NO: 1), 4 (SEQ ID NO: 3), 7 (SEQ ID NO: 5), 11 (SEQ ID NO: 7) or 22A–C (SEQ ID NO: 43) or the nucleotide sequence contained in the plasmids pEXJ-rNPFF1, pWE15-hNPFF1, pCDNA3.1-hNPFF2b, pcDNA3.1-hNPFF1, or pcDNA3.1-rNPFF2-f respectively, that is, a nucleotide sequence which is translated into the same amino acid sequence.

This invention also encompasses DNAs and cDNAs which encode amino acid sequences which differ from those of the polypeptides of this invention, but which should not produce phenotypic changes. Alternately, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (R. F. Spurney et al. (1997); Fong, T. M. et al. (1995); Underwood, D. J. et al. (1994); Graziano, M. P. et al. (1996); Guam X. M. et al. (1995)).

The modified polypeptides of this invention may be transfected into cells either transiently or stably using methods well-known in the art, examples of which are disclosed herein. This invention also provides for binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention provides an isolated nucleic acid encoding a mammalian NPFF receptor. In one embodiment, the nucleic acid is DNA. In another embodiment, the DNA is cDNA. In another embodiment, the DNA is genomic DNA. In another embodiment, the nucleic acid is RNA.

In one embodiment, the mammalian NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In a further embodiment, the mammalian NPFF receptor is a NPFF2 receptor. In one embodiment, the mammalian NPFF2 receptor is a human NPFF2 receptor. In another embodiment, the mammalian NPFF2 receptor is a rat NPFF2 receptor.

This invention also provides an isolated nucleic acid encoding species homologs of the NPFF receptors encoded by the nucleic acid sequence shown in FIGS. 1 (SEQ ID NO: 1), 4 (SEQ ID NO: 3), 7 (SEQ ID NO: 5), 11 (SEQ ID NO: 7) or 22A–C (SEQ ID NO: 43) encoded by the plasmid pEXJ-rNPFF1, pWE15-hNPFF1, pCDNA3.1-hNPFF2b, pcDNA3.1-hNPFF1, or pcDNA3.1-rNPFF2-f respectively. In one embodiment, the nucleic acid encodes a mammalian NPFF receptor homolog which has substantially the same amino acid sequence as does the NPFF receptor encoded by the plasmid pEXJ-rNPFF1, pWE15-hNPFF1, pCDNA3.1-hNPFF2b, pcDNA3.1-hNPFF1 or pcDNA3.1-rNPFF2-f. In another embodiment, the nucleic acid encodes a mammalian NPFF receptor homolog which has above 65% amino acid identity to the NPFF receptor encoded by the plasmid pEXJ-rNPFF1, pWE15-hNPFF1, pCDNA3.1-hNPFF2b, pcDNA3.1-hNPFF1 or pcDNA3.1-rNPFF2-f; preferably above 75% amino acid identity to the NPFF receptor encoded by the plasmid pEXJ-rNPFF1, pWE15-hNPFF1, pCDNA3.1-hNPFF2b, pcDNA3.1-hNPFF1 or pcDNA3.1-rNPFF2-f; more preferably above 85% amino acid identity to the NPFF receptor encoded by the plasmid pEXJ-rNPFF1, pWE15-hNPFF1, pCDNA3.1-hNPFF2b, pcDNA3.1-hNPFF1 or pcDNA3.1-rNPFF2-f; most preferably above 95% amino acid identity to the NPFF receptor encoded by the plasmid pEXJ-rNPFF1, PWE15-hNPFF1, pCDNA3.1-hNPFF2b, pcDNA3.1-hNPFF1, or pcDNA3.1-rNPFF2-f. In another embodiment, the mammalian NPFF receptor homolog has above 70% nucleic acid identity to the NPFF receptor gene contained in plasmid pEXJ-rNPFF1, pWE15-hNPFF1, pCDNA3.1-hNPFF2b, pcDNA3.1-hNPFF1 or pcDNA3.1-rNPFF2-f; preferably above 80% nucleic acid identity to the NPFF receptor gene contained in the plasmid pEXJ-rNPFF1, pWE15-hNPFF1, pCDNA3.1-hNPFF2b, pcDNA3.1-hNPFF1 or pcDNA3.1-rNPFF2-f; more preferably above 90% nucleic acid identity to the NPFF receptor gene contained in the plasmid pEXJ-rNPFF1, pWE15-hNPFF1, pCDNA3.1-hNPFF2b, pcDNA3.1-hNPFF1 or pcDNA3.1-rNPFF2-f. Examples of methods for isolating and purifying species homologs are described elsewhere (e.g., U.S. Pat. No. 5,602,024, WO94/14957, WO97/26853, WO98/15570).

In separate embodiments of the present invention, the nucleic acid encodes a NPFF receptor which has an amino acid sequence identical to that encoded by the plasmid pEXJ-rNPFF1, pWE15-hNPFF1, pCDNA3.1-hNPFF2b, pcDNA3.1-hNPFF1 or pcDNA3.1-rNPFF2-f. In further embodiments, the NPFF receptor has a sequence substantially the same as the amino acid sequence shown in FIG. 2 (SEQ ID NO: 2), FIG. 5 (SEQ ID NO: 4), FIG. 8 (SEQ ID NO: 6), FIG. 12 (SEQ ID NO: 8) or FIG. 23A–B (SEQ ID NO: 44). In other embodiments, the NPFF receptor has an amino acid sequence identical to the amino acid sequence shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–B (SEQ ID NO: 44).

This invention provides an isolated nucleic acid encoding a modified mammalian NPFF receptor, which differs from a mammalian NPFF receptor by having an amino acid(s) deletion, replacement, or addition in the third intracellular domain.

This invention provides a nucleic acid encoding a mammalian NPFF receptor, wherein the nucleic acid (a) hybridizes to a nucleic acid having the defined sequence shown in FIG. 1 (SEQ ID No: 1) under low stringency conditions or a sequence complementary thereto and (b) is further characterized by its ability to cause a change in the pH of a culture of CHO cells when an NPFF peptide is added to the culture and the CHO cells express the nucleic acid which hybridized to the nucleic acid having the defined sequence or its complement. This invention further provides a nucleic acid encoding a mammalian NPFF receptor, wherein the nucleic acid (a) hybridizes to a nucleic acid having the defined sequence shown in FIG. 4 (SEQ ID NO: 3) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement. This invention also provides a nucleic acid encoding a mammalian NPFF receptor, wherein the nucleic acid (a) hybridizes to a nucleic acid having the defined sequence shown in FIG. 7 (SEQ ID NO: 5) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

This invention further provides a nucleic acid encoding a mammalian NPFF receptor, wherein the nucleic acid (a) hybridizes to a nucleic acid having the defined sequence shown in FIG. 11 (SEQ ID NO: 7) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

This invention further provides a nucleic acid encoding a mammalian NPFF receptor, wherein the nucleic acid (a) hybridizes to a nucleic acid having the defined sequence shown in FIGS. 22A–22C (SEQ ID NO: 43) under low stringency conditions or a sequence complementary thereto and (b) is further characterized by its ability to cause a change in the pH of a culture of CHO cells when a NPFF peptide is added to the culture and the CHO cells express the nucleic acid which hybridized to the nucleic acid having the defined sequence or its complement.

In one embodiment, the mammalian NPFF receptor is a rat NPFF1 receptor. In another embodiment, the mammalian NPFF receptor is a human NPFF1 receptor. In a further embodiment, the mammalian NPFF receptor is a human NPFF2 receptor. In a further embodiment, the mammalian NPFF receptor is a rat NPFF2 receptor. For purpose of the invention hybridization under low stringency conditions means hybridization performed at 40° C. in a hybridization buffer containing 25% formamide, 5×SCC, 7 mM Tris, 1×Denhardt's, 25 $\mu$l/ml salmon sperm DNA. Wash at 40° C. in 0.1×SCC, 0.1% SDS. Changes in pH are measured through microphysiometric measurement of receptor mediated extracellular acidification rates. Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway. General guidelines for transient receptor expression, cell preparation and microphysiometric recording are described elsewhere (Salon, J. A. and Owicki, J. A., 1996). Receptors and/or control vectors are transiently expressed in CHO-K1 cells, by liposome mediated transfection according to the manufacturers recommendations (LipofectAMINE, GibcoBRL, Gaithersburg, Md.), and maintained in Ham's F-12 complete (10% serum). A total of 10 $\mu$g of DNA is used to transfect each 75cm$^2$ flask which had been split 24 hours prior to the transfection and judged to be 70–80% confluent at the time of transfection. 24 hours post transfection, the cells are harvested and 3×10$^5$ cells seeded into microphysiometer capsules. Cells are allowed to attach to the capsule membrane for an additional 24 hours; during the last 16 hours, the cells are switched to serum-free F-12 complete to minimize ill-defined metabolic stimulation caused by assorted serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established. A standard recording protocol specifies a 100 $\mu$l/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 $\mu$M final concentration. Ligand samples are then washed out and the acidification rates reported are expressed as a percentage increase of the peak response over the baseline rate observed just prior to challenge. Endogenous NPFF peptides include rat NPFF (FLFQPQRF-NH2) (SEQ ID NO: 45) and rat A18Fa (AGEGLSSPFWSLAAPQRF-NH2) (SEQ ID NO: 46).

This invention provides a purified mammalian NPFF receptor protein. In one embodiment, the purified mammalian NPFF receptor protein is a human NPFF1 receptor protein. In another embodiment, the purified mammalian NPFF receptor protein is a rat NPFF1 receptor protein. In a further embodiment, the purified mammalian NPFF receptor protein is a human NPFF2 receptor protein. In a further embodiment, the purified mammalian NPFF receptor protein is a rat NPFF2 receptor protein.

This invention provides a vector comprising nucleic acid encoding a mammalian NPFF receptor. In one embodiment, the mammalian NPFF receptor protein is a NPFF1 receptor protein. In another embodiment of the present invention the mammalian NPFF receptor protein is a NPFF2 receptor protein. In one embodiment, the mammalian NPFF receptor is a rat NPFF1 receptor. In another embodiment, the mammalian NPFF receptor is a human NPFF1 receptor. In a further embodiment, the mammalian NPFF receptor is a human NPFF2 receptor. In a further embodiment, the purified mammalian NPFF receptor protein is a rat NPFF2 receptor.

In an embodiment, the vector is adapted for expression in a cell which comprises the regulatory elements necessary for expression of the nucleic acid in the cell operatively linked to the nucleic acid encoding the mammalian NPFF receptor as to permit expression thereof. In separate embodiments, the cell is a bacterial cell, an amphibian cell, a yeast cell, an insect cell or a mammalian cell. In another embodiment, the vector is a baculovirus. In one embodiment, the vector is a plasmid.

This invention provides a plasmid designated pEXJ-rNPFF1 (ATCC Accession No. 203184). This plasmid comprises the regulatory elements necessary for expression of DNA in a mammalian cell operatively linked to DNA encoding the mammalian NPFF1 receptor so as to permit expression thereof. This invention also provides a plasmid designated pWE15-hNPFF1 (ATCC Accession No. 203183). This invention further provides a plasmid designated pCDNA3.1-hNPFF2b (ATCC Accession No. 203255). This invention additionally provides a plasmid designated pcDNA3.1-hNPFF1 (ATCC Accession No. 203605). This invention additionally provides a plasmid designated pcDNA3.1-rNPFF2-f (ATCC Patent Deposit Designation No.PTA-535).

These plasmids (pEXJ-rNPFF1 and pWE15-hNPFF1) were deposited on Sep. 9, 1998, with the American Type Culture Collection (ATCC), 10801 University Blvd., Manassas, Va. 20110–2209, U.S.A. under the provisions of the Budapest Treaty for the International Recognition of the Deposit of Microorganisms for the Purposes of Patent Procedure and were accorded ATCC Accession Nos. 203184 and 203183, respectively. Plasmid pCDNA3.1-hNPFF2b was deposited on Sep. 22, 1998, with the American Type Culture Collection (ATCC), 10801 University Blvd., Manassas, Va. 20110–2209, U.S.A. under the provisions of the Budapest Treaty for the International Recognition of the Deposit of Microorganisms for the Purposes of Patent Procedure and was accorded ATCC Accession No. 203255. Plasmid pcDNA3.1-hNPFF1 was deposited on Jan. 21, 1999, with the American Type Culture Collection (ATCC), 10801 University Blvd., Manassas, Va. 20110–2209, U.S.A. under the provisions of the Budapest Treaty for the International Recognition of the Deposit of Microorganisms for the Purposes of Patent Procedure and was accorded ATCC Accession No. 203605. Plasmid pcDNA3.1-rNPFF2-f was deposited on Aug. 17, 1999, with the American Type Culture Collection (ATCC), 10801 University Blvd., Manassas, Va. 20110–2209, U.S.A. under the provisions of the Budapest Treaty for the International Recognition of the Deposit of Microorganisms for the Purposes of Patent Procedure and was accorded ATCC Patent Deposit Designation No. PTA-535.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising a vector comprising a nucleic acid encoding the mammalian NPFF receptor. In an embodiment, the cell is a non-mammalian cell. In a further embodiment, the non-mammalian cell is a Xenopus oocyte cell or a Xenopus melanophore cell. In another embodment, the cell is a mammalian cell. In a further embodiment, the mammalian cell is a COS-7 cell, a 293 human embryonic kidney cell (HEK-293 cell), a NIH-3T3 cell, a LM(tk–) cell, a mouse Y1 cell, or a CHO cell.

This invention provides an insect cell comprising a vector adapted for expression in an insect cell which comprises a nucleic acid encoding a mammalian NPFF receptor. In another embodiment, the insect cell is an Sf9 cell, an Sf21 cell or a Trichoplusia ni 5B1-4 (HighFive) cell.

This invention provides a membrane preparation isolated from any one of the cells described above.

This invention provides a nucleic acid probe comprising at least 15 nucleotides, which probe specifically hybridizes with a nucleic acid encoding a mammalian NPFF receptor, wherein the probe has a unique sequence corresponding to a sequence present within one of the two strands of the nucleic acid encoding the mammalian NPFF receptor and are contained in plasmid pEXJ-rNPFF1, plasmid pWE15-hNPFF1, pCDNA3.1-hNPFF2b, pcDNA3.1-hNPFF1 or pcDNA3.1-rNPFF2-f. This invention also provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 1 (SEQ ID NO: 1) or (b) the reverse complement thereto. This invention also provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 4 (SEQ ID NO: 3) or (b) the reverse complement thereto. This invention also provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 7 (SEQ ID NO: 5) or (b) the reverse complement thereto. This invention also provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIG. 11 (SEQ ID NO: 7) or (b) the reverse complement thereto. This invention also provides a nucleic acid probe comprising at least 15 nucleotides, which probe specifically hybridizes with a nucleic acid encoding a mammalian NPFF receptor, wherein the probe has a unique sequence corresponding to a sequence present within (a) the nucleic acid sequence shown in FIGS. 22A–22C (SEQ ID NO: 43) or (b) the reverse complement thereto. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or flourescent dye, to facilitate detection of the probe. DNA probe molecules may be produced by insertion of a DNA molecule which encodes the polypeptides of this invention into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the polypeptides of this invention downstream of a bacteriophage promoter such as T3, T7, or SP6. Large amounts of RNA probe may be produced by incubating the labeled nucleotides with the linearized fragment where it contains an upstream promoter in the presence of the appropriate RNA polymerase.

This invention provides an antisense oligonucleotide having a sequence capable of specifically hybridizing to RNA encoding a mammalian NPFF receptor, so as to prevent translation of the RNA. This invention also provides an antisense oligonucleotide having a sequence capable of specifically hybridizing to genomic DNA encoding a mammalian NPFF receptor, so as to prevent translation of the genomic DNA. In one embodiment, the oligonucleotide comprises chemically modified nucleotides or nucleotide analogues.

This invention provides an antibody capable of binding to a mammalian NPFF receptor encoded by a nucleic acid encoding a mammalian NPFF receptor. In one embodiment, the mammalian NPFF receptor is a rat NPFF1 receptor. In another embodiment, the mammalian NPFF receptor is a human NPFF1 receptor. In a further embodiment, the mammalian NPFF receptor is a human NPFF2 receptor. In a further embodiment, the mammalian NPFF receptor is a rat NPFF2 receptor. This invention also provides an agent capable of competitively inhibiting the binding of the antibody to a mammalian NPFF receptor. In one embodiment, the antibody is a monoclonal antibody or antisera.

This invention provides a pharmaceutical composition comprising (a) an amount of the oligonucleotide capable of passing through a cell membrane and effective to reduce expression of a mammalian NPFF receptor and (b) a pharmaceutically acceptable carrier capable of passing through the cell membrane. In an embodiment, the oligonucleotide is coupled to a substance which inactivates mRNA. In a further embodiment, the substance which inactivates mRNA is a ribozyme. In another embodiment, the pharmaceutically acceptable carrier comprises a structure which binds to a mammalian NPFF receptor on a cell capable of being taken up by the cells after binding to the structure. In a further embodiment, the pharmaceutically acceptable carrier is capable of binding to a mammalian NPFF receptor which is specific for a selected cell type.

This invention provides a pharmaceutical composition which comprises an amount of an antibody effective to block binding of a ligand to a human NPFF receptor and a pharmaceutically acceptable carrier.

As used herein, the phrase "pharmaceutically acceptable carrier" means any of the standard pharmceutically acceptable carriers. Examples include, but are not limited to, phosphate buffered saline, physiological saline, water, and emulsions, such as oil/water emulsions.

This invention provides a transgenic, nonhuman mammal expressing DNA encoding a mammalian NPFF receptor. This invention also provides a transgenic, nonhuman mammal comprising a homologous recombination knockout of the native mammalian NPFF receptor. This invention further provides a transgenic, nonhuman mammal whose genome comprises antisense DNA complementary to the DNA encoding a mammalian NPFF receptor so placed within the genome as to be transcribed into antisense mRNA which is complementary to mRNA encoding the mammalian NPFF receptor and which hybridizes to mRNA encoding the mammalian NPFF receptor, thereby reducing its translation. In an embodiment, the DNA encoding the mammalian NPFF receptor additionally comprises an inducible promoter. In another embodiment, the DNA encoding the mammalian NPFF receptor additionally comprises tissue specific regulatory elements. In a further embodiment, the transgenic, nonhuman mammal is a mouse.

Animal model systems which elucidate the physiological and behavioral roles of the polypeptides of this invention are produced by creating transgenic animals in which the activity of the polypeptide is either increased or decreased, or the amino acid sequence of the expressed polypeptide is altered, by a variety of techniques. Examples of these techniques include, but are not limited to: 1) Insertion of normal or mutant versions of DNA encoding the polypeptide, by microinjection, electroporation, retroviral transfection or other means well known to those in the art, into appropriate fertilized embryos in order to produce a transgenic animal or 2) Homologous recombination of mutant or normal, human or animal versions of these genes with the native gene locus in transgenic animals to alter the regulation of expression or the structure of these polypeptide sequences. The technique of homologous recombination is well known in the art. It replaces the native gene with the inserted gene and so is useful for producing an animal that cannot express native polypeptides but does express, for example, an inserted mutant polypeptide, which has replaced the native polypeptide in the animal's genome by recombination, resulting in underexpression of the transporter. Microinjection adds genes to the genome, but does not remove them, and so is useful for producing an animal which expresses its own and added polypeptides, resulting in overexpression of the polypeptides.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a polypeptide of this invention is purified from a vector by methods well known in the art. Inducible promoters may be fused with the coding region of the DNA to provide an experimental means to regulate expression of the trans-gene. Alternatively, or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a process for identifying a chemical compound which specifically binds to a mammalian NPFF receptor which comprises contacting cells containing DNA encoding and expressing on their cell surface the mammalian NPFF receptor, wherein such cells do not normally express the mammalian NPFF receptor, with the compound under conditions suitable for binding, and detecting specific binding of the chemical compound to the mammalian NPFF receptor. This invention also provides a process for identifying a chemical compound which specifically binds to a mammalian NPFF receptor which comprises contacting a membrane fraction from a cell extract of cells containing DNA encoding and expressing on their cell surface the mammalian NPFF receptor, wherein such cells do not normally express the mammalian NPFF receptor, with the compound under conditions suitable for binding, and detecting specific binding of the chemical compound to the mammalian NPFF receptor. In one embodiment, the NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In one embodiment, the mammalian NPFF receptor is a NPFF2 receptor. In a further embodiment, the mammalian NPFF2 receptor is a human NPFF2 receptor. In a further embodiment, the mammalian NPFF2 receptor is a rat NPFF2 receptor. In another embodiment, the mammalian NPFF receptor has substantially the same amino acid sequence as the NPFF receptor encoded by plasmid pEXJ-rNPFF1, plasmid pWE15-hNPFF1, plasmid pCDNA3.1-hNPFF2b, plasmid pcDNA3.1-hNPFF1, or plasmid pcDNA3.1-rNPFF2-f. In a further embodiment, the mammalian NPFF receptor has substantially the same amino acid sequence as that shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–23B (SEQ ID NO: 44). In another embodiment, the mammalian NPFF receptor has the amino acid sequence shown in FIG. 2 (SEQ ID NO: 2), FIG. 5 (SEQ ID NO: 4) FIG. 8 (SEQ ID NO: 6), FIG. 12 (SEQ ID NO: 8) or FIGS. 23A–23B (SEQ ID NO: 44). In one embodiment, the compound is not previously known to bind to a mammalian NPFF receptor. This invention further provides a compound identified by the above-described processes.

In one embodiment of the above-described processes, the cell is an insect cell. In another embodiment, the cell is a mammalian cell. In a further embodiment, the cell is non-neuronal in origin. In a further embodiment, the nonneuronal cell is a COS-7 cell, 293 human embryonic kidney cell, a CHO cell, a NIH-3T3 cell, a mouse Y1 cell, or a LM(tk–) cell. In an embodiment, the compound is a compound not previously known to bind to a mammalian NPFF receptor. This invention also provides a compound identified by the above-described process.

This invention provides a process involving competitive binding for identifying a chemical compound which specifically binds to a mammalian NPFF receptor which comprises separately contacting cells expressing on their cell surface the mammalian NPFF receptor, wherein such cells do not normally express the mammalian NPFF receptor, with both the chemical compound and a second chemical compound known to bind to the receptor, and with only the second chemical compound, under conditions suitable for binding of both compounds, and detecting specific binding of the chemical compound to the mammalian NPFF receptor, a decrease in the binding of the second chemical compound to the mammalian NPFF receptor in the presence of the chemical compound indicating that the chemical compound binds to the mammalian NPFF receptor.

This invention also provides a process involving competitive binding for identifying a chemical compound which specifically binds to a mammalian NPFF receptor which comprises separately contacting a membrane preparation from cells expressing on their cell surface the mammalian NPFF receptor, wherein such cells do not normally express the mammalian NPFF receptor, with both the chemical compound and a second chemical compound known to bind to the receptor, and with only the second chemical compound, under conditions suitable for binding of both compounds, and detecting specific binding of the chemical compound to the mammalian NPFF receptor, a decrease in the binding of the second chemical compound to the mammalian NPFF receptor in the presence of the chemical compound indicating that the chemical compound binds to the mammalian NPFF receptor.

In an embodiment of the present invention, the second chemical compound is NPFF or a homolog or analog of NPFF.

In one embodiment, the mammalian NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In another embodiment, the mammalian NPFF receptor is a NPFF2 receptor. In a further embodiment, the NPFF2 receptor is a human NPFF2 receptor. In a further embodiment, the NPFF2 receptor is a rat NPFF2 receptor. In another embodiment, the mammalian NPFF receptor has substantially the same amino acid sequence as the NPFF receptor encoded by plasmid pEXJ-rNPFF1, pWE15-hNPFF1, pCDNA3.1-hNPFF2b, pcDNA3.1-hNPFF1 or pcDNA3.1-rNPFF2-f. In a further embodiment, the mammalian NPFF receptor has substantially the same amino acid sequence as that shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–B (SEQ ID NO: 44). In another embodiment, the mammalian NPFF receptor has the amino acid sequence shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–B (SEQ ID NO: 44).

In one embodiment, the cell is an insect cell. In another embodiment, the cell is a mammalian cell. In a further embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk–) cell. In one embodiment, the compound is not previously known to bind to a mammalian NPFF receptor.

This invention provides a compound identified by the above-described processes.

This invention provides a method of screening a plurality of chemical compounds not known to bind to a mammalian NPFF receptor to identify a compound which specifically binds to the mammalian NPFF receptor, which comprises (a) contacting cells transfected with and expressing DNA encoding the mammalian NPFF receptor with a compound known to bind specifically to the mammalian NPFF receptor; (b) contacting the preparation of step (a) with the plurality of compounds not known to bind specifically to the mammalian NPFF receptor, under conditions permitting binding of compounds known to bind the mammalian NPFF receptor; (c) determining whether the binding of the compound known to bind to the mammalian NPFF receptor is reduced in the presence of the compounds within the plurality of compounds, relative to the binding of the compound in the absence of the plurality of compounds; and if so (d) separately determining the binding to the mammalian NPFF receptor of compounds included in the plurality of compounds, so as to thereby identify the compound which specifically binds to the mammalian NPFF receptor.

This invention provides a method of screening a plurality of chemical compounds not known to bind to a mammalian NPFF receptor to identify a compound which specifically binds to the mammalian NPFF receptor, which comprises (a) contacting a membrane preparation from cells transfected with and expressing DNA encoding the mammalian NPFF receptor with the plurality of compounds not known to bind specifically to the mammalian NPFF receptor under conditions permitting binding of compounds known to bind to the mammalian NPFF receptor; (b) determining whether the binding of a compound known to bind to the mammalian NPFF receptor is reduced in the presence of any compound within the plurality of compounds, relative to the binding of the compound in the absence of the plurality of compounds; and if so (c) separately determining the binding to the mammalian NPFF receptor of compounds included in the plurality of compounds, so as to thereby identify the compound which specifically binds to the mammalian NPFF receptor.

This invention provides a method of screening a plurality of chemical compounds not known to bind to a mammalian NPFF receptor to identify a compound which specifically binds to the mammalian NPFF receptor, which comprises (a) contacting a membrane preparation from cells transfected with and expressing the mammalian NPFF receptor with a compound known to bind specifically to the mammalian NPFF receptor; (b) contacting the preparation of step (a) with the plurality of compounds not known to bind specifically to the mammalian NPFF receptor, under conditions permitting binding of compounds known to bind the mammalian NPFF receptor; (c) determining whether the binding of the compound known to bind to the mammalian NPFF receptor is reduced in the presence of the compounds within the plurality of compounds, relative to the binding of the compound in the absence of the plurality of compounds; and if so (d) separately determining the binding to the mammalian NPFF receptor of compounds included in the plurality of compounds, so as to thereby identify the compound which specifically binds to the mammalian NPFF receptor.

In one embodiment of the above-described methods, the mammalian NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In another embodiment, the mammalian NPFF receptor is a NPFF2 receptor. In a further embodiment the NPFF2 receptor is a human NPFF2 receptor. In a further embodiment, the mammalian NPFF2 receptor is a rat NPFF2 receptor. In another embodiment, the cell is a mammalian cell. In a further embodiment, the mammalian cell is non-neuronal in origin. In another embodiment, the non-neuronal cell is a COS-7 cell, a 293 human embryonic kidney cell, a LM(tk–) cell, a CHO cell, a mouse Y1 cell, or an NIH-3T3 cell.

This invention also provides a method of detecting expression of a mammalian NPFF receptor by detecting the presence of mRNA coding for the mammalian NPFF receptor which comprises obtaining total mRNA from the cell and contacting the mRNA so obtained from a nucleic acid probe under hybridizing conditions, detecting the presence of mRNA hybridizing to the probe, and thereby detecting the expression of the mammalian NPFF receptor by the cell.

This invention further provides a method of detecting the presence of a mammalian NPFF receptor on the surface of a cell which comprises contacting the cell with an antibody under conditions permitting binding of the antibody to the receptor, detecting the presence of the antibody bound to the cell, and thereby detecting the presence of the mammalian NPFF receptor on the surface of the cell.

This invention provides a method of determining the physiological effects of varying levels of activity of mammalian NPFF receptors which comprises producing a transgenic, nonhuman mammal whose levels of mammalian NPFF receptor activity are varied by use of an inducible promoter which regulates mammalian NPFF receptor expression.

This invention also provides a method of determining the physiological effects of varying levels of activity of mammalian NPFF receptors which comprises producing a panel of transgenic, nonhuman mammals each expressing a different amount of mammalian NPFF receptor.

This invention provides a method for identifying an antagonist capable of alleviating an abnormality wherein the abnormality is alleviated by decreasing the activity of a mammalian NPFF receptor comprising administering a compound to a transgenic, nonhuman mammal, and determining whether the compound alleviates the physical and behavioral abnormalities displayed by the transgenic, nonhuman mammal as a result of overactivity of a mammalian NPFF receptor, the alleviation of the abnormality identifying the compound as an antagonist. This invention also provides an antagonist identified by the above-described method. This invention further provides a pharmaceutical composition comprising an antagonist identified by the above-described method and a pharmaceutically acceptable carrier. This invention provides a method of treating an abnormality in a subject wherein the abnormality is alleviated by decreasing the activity of a mammalian NPFF receptor which comprises administering to the subject an effective amount of this pharmaceutical composition, thereby treating the abnormality.

This invention provides a method for identifying an agonist capable of alleviating an abnormality in a subject wherein the abnormality is alleviated by increasing the activity of a mammalian NPFF receptor comprising administering a compound to transgenic, nonhuman mammal, and determining whether the compound alleviates the physical and behavioral abnormalities displayed by the transgenic, nonhuman mammal, the alleviation of the abnormality identifying the compound as an agonist. This invention also provides an agonist identified by the above-described method. This invention further provides a pharmaceutical composition comprising an agonist identified by the above-described method and a pharmaceutically acceptable carrier. This invention further provides a method of treating an abnormality in a subject wherein the abnormality is alleviated by increasing the activity of a mammalian NPFF receptor which comprises administering to the subject an effective amount of this pharmaceutical composition, thereby treating the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian NPFF receptor and labeled with a detectable marker; (e) detecting labeled bands which have hybridized to the DNA encoding a mammalian NPFF receptor labeled with a detectable marker to create a unique band pattern specific to the DNA of subjects suffering from the disorder; (f) preparing DNA obtained for diagnosis by steps (a)–(e); and (g) comparing the unique band pattern specific to the DNA of subjects suffering from the disorder from step (e) and the DNA obtained for diagnosis from step (f) to determine whether the patterns are the same or different and to diagnose thereby predisposition to the disorder if the patterns are the same. In one embodiment, a disorder associated with the activity of a specific mammalian allele is diagnosed.

This invention provides a method of preparing the purified mammalian NPFF receptor which comprises: (a) inducing cells to express the mammalian NPFF receptor; (b) recovering the mammalian NPFF receptor from the induced cells; and (c) purifying the mammalian NPFF receptor so recovered.

This invention provides a method of preparing the purified mammalian NPFF receptor which comprises: (a) inserting nucleic acid encoding the mammalian NPFF receptor in a suitable vector; (b) introducing the resulting vector in a suitable host cell; (c) placing the resulting cell in suitable condition permitting the production of the isolated mammalian NPFF receptor; (d) recovering the mammalian NPFF receptor produced by the resulting cell; and (e) purifying the mammalian NPFF receptor so recovered.

This invention provides a process for determining whether a chemical compound is a mammalian NPFF receptor agonist which comprises contacting cells transfected with and expressing DNA encoding the mammalian NPFF receptor with the compound under conditions permitting the activation of the mammalian NPFF receptor, and detecting an increase in mammalian NPFF receptor activity, so as to thereby determine whether the compound is a mammalian NPFF receptor agonist. This invention also provides a process for determining whether a chemical compound is a mammalian NPFF1 receptor antagonist which comprises contacting cells transfected with and expressing DNA encoding the mammalian NPFF receptor with the compound in the presence of a known mammalian NPFF receptor agonist, under conditions permitting the activation of the mammalian NPFF receptor, and detecting a decrease in mammalian NPFF receptor activity, so as to thereby determine whether the compound is a mammalian NPFF receptor antagonist. In one embodiment, the mammalian NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In one embodiment, the mammalian NPFF receptor is a NPFF2 receptor. In a further embodiment, the mammalian NPFF2 receptor is a human NPFF2 receptor. In a further embodiment, the mammalian NPFF2 receptor is a rat NPFF2 receptor.

This invention further provides a pharmaceutical composition which comprises an amount of a mammalian NPFF receptor agonist determined by the above-described process effective to increase activity of a mammalian NPFF receptor and a pharmaceutically acceptable carrier. In one embodiment, the mammalian NPFF receptor agonist is not previously known.

This invention provides a pharmaceutical composition which comprises an amount of a mammalian NPFF receptor antagonist determined by the above-described process effective to reduce activity of a mammalian NPFF receptor and a pharmaceutically acceptable carrier. In one embodiment, the mammalian NPFF receptor antagonist is not previously known.

This invention provides a process for determining whether a chemical compound specifically binds to and activates a mammalian NPFF receptor, which comprises contacting cells producing a second messenger response and expressing on their cell surface the mammalian NPFF receptor, wherein such cells do not normally express the mammalian NPFF receptor, with the chemical compound under conditions suitable for activation of the mammalian NPFF receptor, and measuring the second messenger response in the presence and in the absence of the chemical compound, a change in the second messenger response in the presence of the chemical compound indicating that the compound activates the mammalian NPFF receptor. In one embodiment, the second messenger response comprises chloride channel activation and the change in second messenger is an increase in the level of inward chloride current.

This invention also provides a process for determining whether a chemical compound specifically binds to and inhibits activation of a mammalian NPFF receptor, which comprises separately contacting cells producing a second messenger response and expressing on their cell surface the mammalian NPFF receptor, wherein such cells do not normally express the mammalian NPFF receptor, with both the chemical compound and a second chemical compound known to activate the mammalian NPFF receptor, and with only the second chemical compound, under conditions suitable for activation of the mammalian NPFF receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian NPFF receptor. In one embodiment, the second messenger response comprises chloride channel activation and the change in second messenger response is a smaller increase in the level of inward chloride current in the presence of both the chemical compound and the second chemical compound than in the presence of only the second chemical compound. This invention also provides the above-described processes performed with membrane preparations from cells producing a second messenger response and transfected with and expressing the mammalian NPFF receptor.

In one embodiment of the above-described processes, the mammalian NPFF receptor is a NPFF1 receptor. In a further embodiment, the mammalian NPFF1 receptor is a rat NPFF1 receptor. In another embodiment, the mammalian NPFF1 receptor is a human NPFF1 receptor. In another embodiment, the mammalian NPFF receptor is a NPFF2 receptor. In a further embodiment, the mammalian NPFF2 receptor is a human NPFF2 receptor. In a further embodiment, the mammalian NPFF2 receptor is a rat NPFF2 receptor. In another embodiment, the mammalian NPFF receptor has substantially the same amino acid sequence as encoded by the plasmid pEXJ-rNPFF1, pWE15-hNPFF1, pCDNA3.1-hNPFF2b, pcDNA3.1-hNPFF1 or pcDNA3.1-rNPFF2-f. In a further embodiment, the mammalian NPFF receptor has substantially the same amino acid sequence as that shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–B (SEQ ID NO: 44). In another embodiment, the mammalian NPFF receptor has an amino acid sequence identical to the amino acid sequence shown in FIG. 2 (SEQ ID NO: 2), FIG. 5 (SEQ ID NO: 4), FIG. 8 (SEQ ID NO: 6), FIG. 12 (SEQ ID NO: 8) or FIGS. 23A–B (SEQ ID NO: 44). In an embodiment, the cell is an insect cell. In a further embodiment, the cell is a mammalian cell. In a still further embodiment, the mammalian cell is nonneuronal in origin. In another embodiment, the nonneuronal cell is a COS-7 cell, CHO cell, 293 human embryonic kidney cell, NIH-3T3 cell or LM(tk–) cell. In an embodiment, the compound is not previously known to bind to a mammalian NPFF receptor. This invention also provides a compound determined by the above-described processes.

This invention also provides a pharmaceutical composition which comprises an amount of a mammalian NPFF receptor agonist determined by the above-described processes effective to increase activity of a mammalian NPFF receptor and a pharmaceutically acceptable carrier. In one embodiment, the mammalian NPFF receptor agonist is not previously known.

This invention further provides a pharmaceutical composition which comprises an amount of a mammalian NPFF receptor antagonist determined by the above-described processes effective to reduce activity of a mammalian NPFF receptor and a pharmaceutically acceptable carrier. In one embodiment, the mammalian NPFF receptor antagonist is not previously known.

This invention provides a method of screening a plurality of chemical compounds not known to activate a mammalian NPFF receptor to identify a compound which activates the mammalian NPFF receptor which comprises: (a) contacting cells transfected with and expressing the mammalian NPFF receptor with the plurality of compounds not known to activate the mammalian NPFF receptor, under conditions permitting activation of the mammalian NPFF receptor; (b) determining whether the activity of the mammalian NPFF receptor is increased in the presence of the compounds; and if so (c) separately determining whether the activation of the mammalian NPFF receptor is increased by each compound included in the plurality of compounds, so as to thereby identify the compound which activates the mammalian NPFF receptor. In one embodiment, the mammalian NPFF receptor is a human NPFF receptor. In a further embodiment the human NPFF receptor is a human NPFF1 receptor or a human NPFF2 receptor.

This invention provides a method of screening a plurality of chemical compounds not known to inhibit the activation of a mammalian NPFF receptor to identify a compound which inhibits the activation of the mammalian NPFF receptor, which comprises: (a) contacting cells transfected with and expressing the mammalian NPFF receptor with the plurality of compounds in the presence of a known mammalian NPFF receptor agonist, under conditions permitting activation of the mammalian NPFF receptor; (b) determining whether the activation of the mammalian NPFF receptor is reduced in the presence of the plurality of compounds, relative to the activation of the mammalian NPFF receptor in the absence of the plurality of compounds; and if so (c) separately determining the inhibition of activation of the mammalian NPFF receptor for each compound included in the plurality of compounds, so as to thereby identify the compound which inhibits the activation of the mammalian NPFF receptor. In one embodiment, the mammalian NPFF receptor is a NPFF1 receptor. In a further embodiment, the mammalian NPFF1 receptor is a rat NPFF1 receptor. In another embodiment, the NPFF1 receptor is a human NPFF1 receptor. In another embodiment, the mammalian NPFF receptor is a NPFF2 receptor. In a further embodiment, the NPFF2 receptor is a human NPFF2 receptor. In a further embodiment, the mammalian NPFF2 receptor is a rat NPFF2 receptor.

In one embodiment of the above-described methods, the cell is a mammalian cell. In another embodiment, the mammalian cell is non-neuronal in origin. In a further embodiment, the non-neuronal cell is a COS-7 cell, a 293 human embryonic kidney cell, a LM(tk−) cell or an NIH-3T3 cell.

This invention provides a pharmaceutical composition comprising a compound identified by the above-described methods effective to increase mammalian NPFF receptor activity and a pharmaceutically acceptable carrier.

This invention also provides a pharmaceutical composition comprising a compound identified by the above-described methods effective to decrease mammalian NPFF receptor activity and a pharmaceutically acceptable carrier.

This invention further provides a method of measuring polypeptide activation in an oocyte expression system such as a Xenopus oocyte expression system or melanophore. In an embodiment, polypeptide activation is determined by measurement of ion channel activity. In another embodiment, polypeptide activation is measured by aequerin luminescence.

Expression of genes in Xenopus oocytes is well known in the art (Coleman, A., 1984; Masu, Y.,et al., 1994) and is performed using microinjection of native mRNA or in vitro synthesized mRNA into frog oocytes. The preparation of in vitro synthesized mRNA can be performed by various standard techniques (Sambrook, et al. 1989) including using T7 polymerase with the mCAP RNA mapping kit (Stratagene).

This invention provides a method of treating an abnormality in a subject wherein the abnormality is alleviated by increasing the activity of a mammalian NPFF receptor which comprises administering to the subject an amount of a compound which is a mammalian NPFF receptor agonist effective to treat the abnormality. In separate embodiments, the abnormality is a lower urinary tract disorder such as interstitial cystitis or urinary incontinence such as urge incontinence or stress incontinence particularly stress incontinence, a regulation of a steroid hormone disorder, an epinephrine release disorder, a gastrointestinal disorder, irritable bowel syndrome, a cardiovascular disorder, an electrolyte balance disorder, diuresis, hypertension, hypotension, diabetes, hypoglycemia, a respiratory disorder, asthma, a reproductive function disorder, an immune disorder, an endocrine disorder, a musculoskeletal disorder, a neuroendocrine disorder, a cognitive disorder, a memory disorder, a sensory modulation and transmission disorder, a motor coordination disorder, a sensory integration disorder, a motor integration disorder, a dopaminergic function disorder, a serotonergic function disorder, an appetite disorder, obesity, a sensory transmission disorder, an olfaction disorder, a sympathetic innervation disorder, an affective disorder, pain, psychotic behavior, morphine tolerance, nicotine addiction, opiate addiction, or migraine.

This invention provides a method of treating an abnormality in a subject wherein the abnormality is alleviated by decreasing the activity of a mammalian NPFF receptor which comprises administering to the subject an amount of a compound which is a mammalian NPFF receptor antagonist effective to treat the abnormality. In separate embodiments, the abnormality is a lower urinary tract disorder such as interstitial cystitis or urinary incontinence such as urge incontinence or stress incontinence particularly stress incontinence, a regulation of a steroid hormone disorder, an epinephrine release disorder, a gastrointestinal disorder, irritable bowel syndrome, a cardiovascular disorder, an electrolyte balance disorder, diuresis, hypertension, hypotension, diabetes, hypoglycemia, a respiratory disorder, asthma, a reproductive function disorder, an immune disorder, an endocrine disorder, a musculoskeletal disorder, a neuroendocrine disorder, a cognitive disorder, a memory disorder, a sensory modulation and transmission disorder, a motor coordination disorder, a sensory integration disorder, a motor integration disorder, a dopaminergic function disorder, a serotonergic function disorder, an appetite disorder, obesity, a sensory transmission disorder, an olfaction disorder, a sympathetic innervation disorder, an affective disorder, pain, psychotic behavior, morphine tolerance, nicotine addiction, opiate addiction, or migraine.

This invention provides a method of treating urinary incontinence which comprises administering to a subject an amount of an antagonist of a human NPFF2 receptor effective to inhibit activation of the receptor and thereby treat incontinence, such as urge incontinence or stress incontinence.

This invention provides a method of treating urinary retention which comprises administering to a subject an amount of an agonist of a human NPFF2 receptor effective to activate the receptor and thereby treat retention.

This invention provides a method of treating hypertension which comprises administering to a subject an amount of an antagonist of a human NPFF1 receptor effective to inhibit activation of the receptor and thereby treat hypertension.

This invention provides a method of treating hypotension which comprises administering to a subject an amount of an agonist of a human NPFF1 receptor effective to activate the receptor and thereby treat hypotension.

This invention also provides the use of mammalian NPFF receptors for analgesia.

This invention provides a process for making a composition of matter which specifically binds to a mammalian NPFF receptor which comprises identifying a chemical compound using any of the processes described herein for identifying a compound which binds to and/or activates or inhibits activation of a mammalian NPFF receptor and then synthesizing the chemical compound or a novel structural and functional analog or homolog thereof. In one embodiment, the mammalian NPFF receptor is a human NPFF1 receptor. In another embodiment, the mammalian NPFF receptor is a human NPFF2 receptor.

This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of a mammalian NPFF receptor or a novel structural and functional analog or homolog thereof. In one embodiment, the mammalian NPFF receptor is a human NPFF1 receptor. In another embodiment, the mammalian NPFF receptor is a human NPFF2 receptor.

This invention provides for use of a human NPFF2 receptor antagonist for the preparation of a pharmaceutical composition for treating urinary incontinence, such as urge incontinence or stress incontinence. This invention provides for use of a human NPFF2 receptor agonist for the preparation of a pharmaceutical composition for treating urinary retention.

This invention provides for use of a human NPFF1 receptor antagonist for the preparation of a pharmaceutical composition for treating hypertension. This invention provides for use of a human NPFF1 receptor agonist for the preparation of a pharmaceutical composition for treating hypotension.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Cloning of Rat and Human NPFF1 Receptor
MOPAC (Mixed Oligonucleotide Primed Amplification of cDNA 100 ng of rat genomic DNA (Clonetech, Palo Alto, Calif.) was used for degenerate MOPAC PCR using Taq DNA polymerase (Boehringer-Mannheim, Indianapolis, Ind.) and the following degenerate oligonucleotides: JAB126, designed based on an alignment of the sixth transmembrane domain of more than 180 members of the rhodopsin superfamily of G protein-coupled receptors; and JAB108, designed based on an alignment of the seventh transmembrane domain of the same rhodopsin superfamily.

The conditions for the MOPAC PCR reaction were as follows: 3 minute hold at 94° C.; 10 cycles of 1 minute at 94° C., 1 minute 45 seconds at 44° C., 2 minutes at 72° C.; 30 cycles of 94° C. for 1 minute, 49° C. for 1 minute 45 seconds, 2 minutes at 72° C.; 4 minute hold at 72° C.; 4° C. until ready for agarose gel electrophoresis.

The products were run on a 1% agarose TAE gel and bands of the expected size (~150 bp) were cut from the gel, purified using the QIAQUICK gel extraction kit (QIAGEN, Chatsworth, Calif.), and subcloned into the TA cloning vector (Invitrogen, San Diego, Calif.). White (insert-containing) colonies were picked and subjected to PCR using pCR2.1 vector primers JAB1 and JAB2 using the Expand Long Template PCR System and the following protocol: 94° C. hold for 3 minutes; 35 cycles of 94° C. for 1 minute, 68° C. for 1 minute 15 seconds; 2 minute hold at 68° C., 4° C. hold until products were ready for purification. PCR products were purified by isopropanol precipitation (10 µl PCR product, 18 µl low TE, 10.5 µl 2M $NaClO_4$ and 21.5 µl isopropanol) and sequenced using the ABI Big Dye cycle sequencing protocol and ABI 377 sequencers (ABI, Foster City, Calif.). Nucleotide and amino acid sequence analyses were performed using the Wisconsin Package (GCG, Genetics Computer Group, Madison, Wis.). Two PCR products produced from rat genomic cDNA (MPR3-RGEN-31 and MPR3-RGEN-45) were determined to be identical clones of a novel G protein-coupled receptor-like sequence based on database searches and its homology to other known G protein-coupled receptors (~30–40% amino acid identity to dopamine D2, orexin, galanin, angiotensin 1 and $5-HT_{2b}$ receptors). This novel sequence was designated SNORF2.

Cloning of the Full-length Coding Sequence of SNORF2 (Rat NPFF1)

Pools of the rat hypothalamic cDNA library "I" were screened by PCR with SNORF2-specific primers JAB208 and JAB209 and the Expand Long Template PCR system (Boehringer-Mannheim, Indianapolis, Ind.) with the following PCR protocol: 94° C. hold for 3 minutes; 40 cycles of 94° C. for 1 minute, 68° C. for 2 minutes; 4 minute hold at 68° C.; 4° C. hold until the samples are run on a gel. This screen yielded a positive pool I36E and a positive sub-pool I36E-17. High stringency hybridization of isolated colonies from I36E-17 with the SNORF2-specific oligonucleotide probe JAB211 and subsequent PCR testing of positive colonies indicated that the isolated clone I36E-17-1B-1 contained at least a partial clone of SNORF2. Sequencing of I36E-17-1B-1 revealed that this insert contained the coding region from the TMIII–TMIV loop through the stop codon, including some 3' untranslated sequence. From this sequence, a new forward primer, JAB221, was designed in TMV. PCR screening of a second rat hypothalamic cDNA library "J" with primers JAB221 and JAB209, and subsequent colony hybridization with the JAB211 probe on a low complexity positive sub-pool resulted in the isolation of a SNORF2 clone J-13–16-A1. Full-length double-stranded sequence of SNORF2 was determined by sequencing both strands of the J-13–16-A1 plasmid using an ABI 377 sequencer as described above. This insert is about 2.8 kb in length with an approximately 200 bp 5' untranslated region, a 1296 bp coding region, and a 1.3 kb 3'untranslated region. The clone is also in the correct orientation for expression in the mammalian expression vector pEXJ.T7. This construct of SNORF2 in pEXJ.T7 was designated BN-6. The full length SNORF2 was determined to be most like the orexin 1 receptor (45% DNA identity, 35% amino acid identity), orexin 2 receptor (40% DNA identity, 32% amino acid identity) and NPY2 receptor (476 DNA identity, 29% amino acid identity), although several other G protein-coupled receptors also displayed significant homology. There were no sequences in the Genbank databases (genemb1, sts, est, gss, or swissprot) that were identical to SNORF2. SNORF2 also showed significant homology (85% nucleotide identity, 93% amino acid identity) to a partial G protein-coupled receptor fragment in the Synaptic Pharmaceutical Corporation in-house database, designated PLC29b. PLC29b, which includes part of the amino terminus through TMIII, was originally isolated from a human genomic library using oligonucleotide probes for NPY4. Subsequent screening of a human hippocampal cDNA library yielded an overlapping sequence extending into TMIV. Based on sequence similarity, this human sequence appears to be a partial clone of the human homolog of SNORF2.

The following is a list of primers and their associated sequences which were used in the cloning of these receptors:

JAB126: 5'-GYNTWYRYNNTNWSNTGGHTNCC-3' (SEQ ID NO: 9)

JAB108: 5'-AVNADNGBRWAVANNANNGGRTT-3' (SEQ ID NO: 10)

JAB1: 5'-TTATGCTTCCGGCTCGTATGTTGTG-3' (SEQ ID NO: 11)

JAB2: 5'-ATGTGCTGCAAGGCGATTAAGTTGGG-3' (SEQ ID NO: 12)

JAB208: 5'-GGTGCTGCTGCTGCTCATCGACTATG-3' (SEQ ID NO:13)

JAB209: 5'-TTGGCGCTGCTGTGGAAGAAGGCCAG-3' (SEQ ID NO: 14)

JAB221: 5'-CGGTGCTCTTCGCGCACATCTACC-3' (SEQ ID NO: 15)

JAB211: 5'-TGCCAAGGGGAAGGCGTAGACCGACAGCA GGTGCAGTTGCA GCTCGATCAGCTCCCCATA-3' (SEQ ID NO: 16)

Isolation of the Full-length Human SNORF2 Receptor Gene (Human NPFF1)

The full-length, intronless version of the human NPFF1 receptor gene may be isolated using standard molecular biology techniques and approaches such as those briefly described below:

Approach #1: To obtain a full-length human NPFF1 receptor, a human cosmid library was screened with a $^{32}$P-labeled oligonucleotide probe, BB609, corresponding to the ⅔ loop of the PLC29b clone. A positive clone was isolated and partially sequenced, revealing part of the amino terminus and TMs I and II.

The full-length sequence may be obtained by sequencing this cosmid clone with additional sequencing primers. Since at least two introns are present in this gene, one in the amino terminus and one just after the third transmembrane domain, the full-length intronless gene may be obtained from cDNA using standard molecular biology techniques. For example, a forward PCR primer designed in the 5'UT and a reverse PCR primer designed in the 3'UT may be used to amplify a full-length, intronless gene from cDNA. RT-PCR localization has identified several human tissues which could be used for this purpose, including cerebellum, spinal cord, hippocampus, lung and kidney. Standard molecular biology techniques could be used to subclone this gene into a mammalian expression vector.

Approach #2: Standard molecular biology techniques could be used to screen commercial human cDNA phage libraries by hybridization under high stringency with a $^{32}$P-labeled oligonucleotide probe, B9609, corresponding to the ⅔ loop of the PLC29b clone. One may isolate a full-length human NPFF1 by obtaining a plaque purified clone from the lambda libraries and then subjecting the clone to direct DNA sequencing using primers from the PLC29b sequence. Alternatively, standard molecular biology techniques could be used to screen in-house human cDNA plasmid libraries by PCR amplification of library pools using primers to the human NPFF1 sequence (BB629, forward primer in TMI, and A71, reverse primer in TMIV). A full-length clone could be isolated by Southern hybridization of colony lifts of positive pools with a $^{32}$P-labeled oligonucleotide probe, BB609, corresponding to the ⅔ loop of the PLC29b clone.

Approach #3: As yet another alternative method, one could utilize 3' and 5' RACE to generate PCR products from human cDNA expressing human NPFF1 (for example, cerebellum, spinal cord, hippocampus, lung and kidney), which contain the additional sequences of human NPFF1. For 5' RACE, a reverse primer derived from PLC29b between the amino terminus and TM IV could be used to amplify the additional amino terminus sequence for hNPFF1. For 3' RACE, a forward primer derived from PLC29b between the amino terminus and TM IV could be used to amplify the additional 3' sequence for hNPFF1, including TMs 5–7 and the COOH terminus. These RACE PCR product could then be sequenced to determine the missing sequence. This new sequence could then be used to design a forward PCR primer in the 5'UT and a reverse primer in the 3'UT. These primers could then be used to amplify a full-length hNPFF1 clone from human cDNA sources known to express NPFF1 (for example, cerebellum, spinal cord, hippocampus, lung and kidney).

BB609:
5'-CCACCCTTGTGGACAACCTCATCACTGGGT GGCCCTTCGACA ATGCCACATGC-3' (SEQ ID NO: 17)

BB629: 5'-CTGCTCTGCATGGTGGGCAACACC-3' (SEQ ID NO: 18)

A71: 5'-GACGGCGATGGTGACGAGCGC-3' (SEQ ID NO: 19)

Cloning of Human NPFF1 Receptor

The sequence of the human NPFF1 (hNPFF1) receptor from the initiating methionine to TMIV was determined to be present in a partial clone, plc29b, found in a Synaptic Pharmaceutical Corporation in-house database. In order to isolate the full-length hNPFF1 receptor cDNA, a human cosmid library (Stratagene) was screened with a $^{32}$P-labeled probe (BB609) corresponding to the II/III loop of plc29b. Partial DNA sequencing of one positive clone from this library, COS28a revealed similar sequence as had been previously shown for plc29b, with an intron downstream of TMIII. In order to obtain sequence in the 3' end of hNPFF1, COS28a was amplified with a vector primer and BB702, BB703 or BB704, forward primers in TMIV. DNA sequencing of these PCR products resulted in the identification of TMIV through the stop codon.

Next, an in-house human spinal cord library was screened by PCR using a forward primer in the region of the initiating methionine (BB729) and a reverse primer corresponding to TMIV (BB728). One positive pool, W4, was subdivided and a positive sub-pool was screened by colony hybridization with a $^{32}$P-labeled probe from TMII, BB676. Plasmid DNA was isolated for clone W4-18-4, renamed BO98, and DNA sequencing revealed that it was full-length but in the wrong orientation for expression in the expression vector pEXJ. To obtain a full-length hNPFF1 construct in the correct orientation, BO98 was amplified with BB757, a forward primer at the initiating methionine which contained an upstream BamHI site, and BB758, a reverse primer at the stop codon which contained a EcoRI site. The products from 3 independent PCR reactions were ligated into pcDNA3.1+ and transformed into DH5E cells. The sequence of one of these transformants, 3.3, was identical to the hNPFF1 sequence previously determined from the consensus of BO98, COS28a and plc29b. Clone 3.3 was renamed BO102.

The hNPFF1 clone contains an open reading frame with 1293 nucleotides and predicts a protein of 430 amino acids (FIGS. 11 and 12). Hydrophobicity analysis reveals seven hydrophobic domains which are presumed to be transmembrane domains (FIG. 13). The sequence of hNPFF1 was determined to be most similar to the rat NPFF1 (86% nucleotide identity, 87% amino acid identity) and human NPFF2 (56% nucleotide identity, 49% amino acid identity (FIG. 14)). The human NPFF1 receptor also shares homology with human orexin, (53% nucleotide identity, 35% amino acid identity), human orexin$_2$ (43% nucleotide identity, 33% amino acid identity), human NPY$_2$ (476 nucleotide identity, 31% amino acid identity), human CCK$_A$ (46% nucleotide identity, 32% amino acid identity), and human CCK$_B$ (46% nucleotide identity, 26% amino acid identity).

The following primers and probes were used in the cloning of hNPFF1:

BB676:
5'-GTCACCAACATGTTCATCCTCAACCTGGC TGTCAGTGACCTGCT GGTGGGCATCTTCTGCATGCC-3' (SEQ ID NO: 20)

BB702: 5'-GCGAGAAGCTGACCCTGCGGAAGG-3' (SEQ ID NO: 21)

BB703: 5'-TCGTCACCATCGCCGTCATCTGGG-3' (SEQ ID NO: 22)

BB704: 5'-CGTCATCTGGGCCGAGGGACACAG-3' (SEQ ID NO: 23)

BB728: 5'-TGACGGCGATGGTGACGAGCGCC-3' (SEQ ID NO: 24)

BB729: 5'-CAGCCTCCCAACAGCAGTTGGCC-3' (SEQ ID NO: 25)

BB757:
5'-TAGCAAGGATCCGCATATGGAGGGGGAGC CCTCCC-3' (SEQ ID NO: 26)

BB758:
5'-CTTCATGAATTCATCGCCTGCATGTATCTC GTGTCC-3' (SEQ ID NO: 27)

Cloning of Human NPFF2 Receptor
Discovery of an Expressed Sequence Tag (EST) AA449919 in GENEMBL Homologous to rNPFF1 (hNPFF2)

A FASTA search of GENEMBL with the full-length sequence of rat NPFF1 (rNPFF1) resulted in the identification of an EST (Accession number AA449919) with a high degree of homology to NPFF1 (57% identity at the DNA level). AA449919 is a 532 bp sequence annotated in Genbank as "Soares total fetus Nb2HF8 9 w Homo sapiens cDNA clone 788698 5' similar to SW:NYR_DROME P25931 NEUROPEPTIDE Y RECEPTOR," which when translated corresponds to the region between the first extracellular loop and the beginning of the sixth transmembrane domain of rNPFF1. GAP analysis of AA449919 with rNPFF1 indicated that there is 57% DNA identity and a 50% amino acid identity between the two receptor sequences over this region. AA449919 displays 60% DNA identity and 59% amino acid identity over the region that overlaps with the known sequence for hNPFF1 (first extracellular loop to TM4), while over the same range rNPFF1 is 62% and 61% identical to AA449919 at the DNA and amino acid levels, respectively. In comparison, hNPFF1 and rNPFF1 share 86% DNA identity and 92% amino acid identity over this region. Given the strong degree of identity between AA449919 and rNPFF1, AA449919 was given the name NPFF-like (hNPFF2).

Cloning the Full-Length Sequence of (NPFF-like) hNPFF2

To determine the full-length coding sequence of AA449919, 5'/3' Rapid Amplification of cDNA ends (RACE) was performed on Clontech Human Spleen Marathon-Ready cDNA (Clontech, Palo Alto, Calif.). For 5' RACE, 5 µl template (human spleen Marathon-Ready cDNA was amplified with oligonucleotide primers JAB256 and AP1, the Expand Long DNA Template PCR System (Boehringer-Mannheim, Indianapolis, IN) and the following PCR protocol were used: 94° C. hold for 3 minutes; 5 cycles of 94° C. for 30 seconds, 72° C. for 4 minutes; 5 cycles of 94° C. for 30 seconds, 70° C. for 4 minutes; 30 cycles of 94° C. for 30 seconds, 68° C. for 4 minutes; 68° C. hold for 4 minutes; 4° C. hold until products were ready to be loaded on a gel. 1 µl of this reaction was subjected to a second round of amplification with primers JAB260 and AP2 and the same PCR protocol. For 3' RACE, 5 µl human spleen Marathon-Ready cDNA was subjected to PCR with primers JAB257 and AP1 with the same PCR protocol that was used for 5' RACE. 1 µl of this reaction was subjected to another round of amplification using AP2 and JAB258 and the same PCR conditions.

The products were run on a it agarose TAE gel and bands greater than 500 bp were extracted from the gel using the QIAQUICK gel extraction kit (QIAGEN, Chatsworth, Calif.). 5 µl of each purified band from the 5' and 3' RACE reactions were directly sequenced with primers JAB261 (5' products) and JAB259 (3' products) using the ABI Big Dye cycle sequencing protocol and ABI377 sequencers (ABI, Foster City, Calif.). The Wisconsin Package (GCG, Genetics Computer Group, Madison, Wis.) and Sequencer 3.0 (Gene Codes Corporation, Ann Arbor, Mich.) were used to put together the full-length contiguous sequence of hNPFF2 from the AA449919 EST and the RACE products.

To attain the full-length hNPFF-like (hNPFF2) coding sequence for expression, human spinal cord cDNA was amplified in eight independent PCR reactions using the Expand Long Template PCR System with buffer I (four of the eight reactions) or buffer 3 (4 reactions) and two oligonucleotide primers with restriction sites incorporated into their 5' ends: BB675 is a forward primer upstream of the initiating methionine and contains a BamHI site, and BB663. The PCR conditions for this reaction were as follows: 94° C. hold for 5 minutes; 37 cycles of 94° C. for 30 seconds, 64° C. for 30 seconds, 68° C. for 2 minutes; a 7 minute hold at 68° C., and a 4° C. hold until products were ready to be loaded on a gel. The products were electrophoresed on a 1% agarose TAE gel, and a band of approximately 1.35 kb was cut and purified using the QIAQUICK gel extraction kit. The purified bands of seven of the eight reactions were cut with BamHI and EcoRI, gel purified again using the same method, and ligated into pcDNA3.1(+) (Invitrogen, Carlsbad, Calif.). Eighteen colonies from the subsequent transformations were picked and determined to be positive for NPFF-like by PCR. Eight of these 18 clones were fully sequenced, and one of these, BO89, was determined to be a full length clone with no point mutations. This construct was renamed pcDNA3.1-hNPFF2b.

For expression of NPFF-like in oocytes, one ul of each of these eight ligations of the BB675-BB663 PCR product into pcDNA3.1(+) was subjected to PCR with AN35, a pcDNA3.1 primer at the CMV promoter site, and the 3' NPFF-like primer BB663 using the Expand Long Template PCR System and the following PCR protocol: 94° C. hold for 3 minutes; 37 cycles of 94° C. for 30 seconds, 65° C. for 30 seconds, 68° C. for 2 minutes; a 7 minute hold at 68° C., and a 4° C. hold until products were ready for in vitro transcription. Of the seven PCR reactions, six yielded products of the expected size.

The following is a list of primers and their associated sequences which were used in the cloning of this receptor (hNPFF2):

AN35:
5'-CGTGTACGGTGGGAGGTCTATATAAGCAG AG-3' (SEQ ID NO: 28)

AP1: 5'-CCATCCTAATACGACTCACTATAGGGC-3' (SEQ ID NO: 29)

AP2: 5¹-ACTCACTATAGGGCTCGAGCGGC-3' (SEQ ID NO: 30)

JAB256: 5'-TGATAGTGAGCTTTGGTTTAAAAGGG-3' (SEQ ID NO: 31)

JAB257: 5'-GAAGATCTACACCACTGTGCTGTTTG-3' (SEQ ID NO: 32)

JAB258: 5'-AACATCTACCTGGCTCCCCTCTCCC-3' (SEQ ID NO: 33)

JAB259: 5'-TTGTCATCATGTATGGAAGGATTGG-3' (SEQ ID NO: 34)

JAB260: 5'-GACCACACACTGGAACCTATCTAC-3' (SEQ ID NO: 35)

JAB261: 5'-GCAATTGCAACTAACGTAAAGACTG-3' (SEQ ID NO: 36)

BB675:
5'-TAGCAAGGATCCGAGGTTCATCATGAATGA GAAATGG-3' (SEQ ID NO: 37)

BB663:
5'-CTTCATGAATTCGCGTAGTAGAGTTAGGAT TATCAC-31 (SEQ ID NO: 38)

For expression of NPFF2, mRNA transcripts were generated as described for NPFF1, using PCR products from ligation reactions or linearized DNA from BO89 as DNA templates. Oocytes were injected with 5–50 ng NPFF2 mRNA and incubated as previously described.

Isolation of the Rat Homologue of NPFF2

To obtain a fragment of the rat homologue of NPFF2, rat genomic DNA (Clontech, Palo Alto, Calif.), rat hypothalamic cDNA or rat spinal cord cDNA was amplified with a forward PCR primer corresponding to TMIV of human NPFF2 (JAB307) and a reverse primer corresponding to TMVI of human NPFF (JAB 306) PCR was performed with the Expand Long Template PCR System (Roche Molecular Biochemicals, Indianapolis, Ind.) under the following conditions: 1 minute at 94° C., 2 minutes at 50° C., 2 minutes at 68° C. for 40 cycles, with a pre- and post-incubation of 3 minutes at 94° C. and 4 minutes at 68° C. respectively. Bands of 368 bp from 3 independent PCR reactions were isolated from a TAE gel, purified using the QIAQUICK gel extraction kit (QIAGEN, Chatsworth, Calif.), and sequenced on both strands as described above. The sequences of these 3 PCR products were identical.

To obtain additional sequence for rat NPFF2, reduced stringency PCR was performed using primers designed against the human NPFF2 $NH_2$ and COOH termini along with PCR primers designed against the rat NPFF2 fragment. For the NH2 terminal sequence, PCR was performed on rat spinal cord cDNA with BB665, a sense primer just upstream of TMI in human NPFF2, and BB795, an antisense primer in the second extracellular loop of the rat NPFF2. For the COOH terminal sequence, PCR was performed on rat spinal cord cDNA with BB793, a sense primer from the third intracellular loop in rat NPFF2, and BB668, an antisense primer just downstream from TMVII in human NPFF2. PCR was performed using the Expand Long Template PCR System (Roche Biochemicals, Indianapolis, Ind.) with buffer 2 ($NH_2$ terminal) or buffer 1 (COOH terminal) and the following conditions: 30 seconds at 94° C., 30 seconds at 42° C. ($NH_2$ terminal) or 50° C. (COOH terminal), 1.5 minutes at 68° C. for 40 cycles, with a pre- and post-incubation of 3 minutes at 94° C. and 4 minutes at 68° C. respectively. A 500 bp band from the $NH_2$ terminal PCR and a 300 bp band from the COOH terminal PCR were isolated from a TAE gel, purified using the QIAQUICK gel extraction kit (QIAGEN, Chatsworth, Calif.), and sequenced on both strands as described above.

A rat liver genomic phage library (2.75 million recombinants, Stratagene, LaJolla, Calif.) was screened using a $^{32}$P-labeled oligonucleotide probe, BB712, corresponding to the second extracellular loop and TMV of the rat NPFF2 fragment above. Hybridization of nitrocellulose filter overlays of the plates was performed at high stringency: 42° C. in a solution containing 50% formamide, 5×SSC (1×SSC is 0.15M sodium chloride, 0.015M sodium citrate), 1×Denhardt's solution (0.026 polyvinylpyrrolindone, 0.02% Ficoll, 0.02% bovine serum albumin), 7 mM Tris and 25 µg/ml sonicated salmon sperm DNA. The filters were washed at 55° C. in 0.1×SSC containing 0.1% sodium dodecyl sulfate and exposed at −70° C. to Kodak BioMax MS film in the presence of an intensifying screen.

Three positive signals, rNPFF2–1, rNPFF2–4 and rNPFF2–6 were isolated on a tertiary plating. A 3.5 kb fragment, from a BglII/EcoRI digest of DNA isolated from rNPFF2–6, was identified by Southern blot analysis with BB712, subcloned into pcDNA3.1 (Invitrogen, San Diego, Calif.) and used to transform E. coli DH5α cells (Gibco BRL, Gaithersburg Md.). Plasmid DNA from one transformant was sequenced using an ABI 377 sequencer as described above. Sequencing with HK137, a sense primer from TMV of the rat NPFF2 fragment revealed the sequence for TMVII, the COOH terminus and some 3'UT. Sequencing with HK139, an antisense primer from TMII of rNPFF2, revealed the presence an intron upstream of TMII.

To determine if any of the three positive plaques contained sequence upstream of this intron, DNA from each of the clones were spotted onto nitrocellulose and hybridized with HK140, an oligonucleotide probe corresponding to TMI of the rat NPFF2 fragment. The rNPFF2–1 and rNPFF2–4 clones were positive. A 2.1 kb fragment, from a HindIII digest of DNA isolated from rNPFF2–4, was identified by Southern blot analysis with HK140, subcloned into pcDNA3.1 (Invitrogen, San Diego, Calif.) and used to transform E. coli DH5α cells (Gibco BRL, Gaithersburg Md.). Sequencing of this fragment with HK138, an antisense primer from TMI of rat NPFF2, revealed the $NH_2$ terminus and 5'UT of the rat NPFF2 receptor.

The full-length NPFF2 was amplified from rat spinal cord cDNA using a sense primer in the 5'UT (HK146, also incorporating a BamHI restriction site) and an antisense primer from the 3'UT (HK147, also incorporating a BstXI restriction site) and the Expand Long Template PCR System (Roche Molecular Biochemicals, Indianapolis, Ind.) using buffer 2 and the following PCR conditions: 30 seconds at 94° C., 2.5 minutes at 68° C. for 32 cycles, with a pre- and post-incubation of 5 minutes at 94° C. and 7 minutes at 68° C., respectively. Products from 5 independent PCR reactions were gel-purified. 1 µl of each reaction was used as a template to re-amplify the product using the same PCR conditions. The products were digested with BamnHI and BstXI and ligated into a modified pcDNA3.1 vector (Invitrogen, San Diego, Calif.). Products from each PCR reaction were sequenced as above. While a consensus amino acid sequence was determined among the PCR products, there was some ambiguity in the nucleotide sequence at 4 positions. To determine if this represented PCR-induced errors or allelic variations, the areas in question were amplified from several lots of genomic DNA. Sequencing of these genomic products revealed the same ambiguities, suggesting allelic variations at these residues. One construct, KO31, was renamed BO119 and later renamed pcDNA3.1-rNPFF2-f.

Oligonucleotide primers and probes used in the identification and isolation of the rat NPFF2:

JAB307: 5'-TTTGTCATTATTATGATCATCTGG-3' (SEQ ID NO: 47)

JAB306: 5'-AATAAAAAGCAGGGCCACAATCAG-3' (SEQ ID NO: 48)

BB665: 5'-TCATTATTTCCTACTTTCTGATC-3' (SEQ ID NO: 49)

BB795: 5'-CTCATTTCCTGGTTTGGCCAATCC-3' (SEQ ID NO: 50)

BB793: 5'-TCTTCAAGACCTCAGCACACAGC-3' (SEQ ID NO: 51)

BB668: 5'-GAGCTGGAAAGCTTCTTGGAAACC-3' (SEQ ID NO: 52)

BB712: 5'-CTGGTGTCGGGAGGATTGGCCAAACCAGG AAATGAGGAGGAT CTACACC-3' (SEQ ID NO: 53)

HK137: 5'-GCAGTGTCAACCCCATCATTTATGG-3' (SEQ ID NO: 54)

HK138: 5'-CAAAGCAAACGACAGTGTTTCCCACC-3' (SEQ ID NO: 55)

HK139: 5'-AGTGACCGTGTGCATGTACCTATTCC-3' (SEQ ID NO: 56)

HK140: 5'-GGTGGGAAACACTGTCGTTTGCTTTGTTGT AATAAGGAATA GGTACATGCACACGGTCAC-3' (SEQ ID NO: 57)

HK146: 5'-GTCACGGATCCAGCCTCTCCTTTGATAAGG TCCACC-3' (SEQ ID NO: 58)

HK147: 5'-GTCAGCCATCGAGTTGGCTTCGTATGCTAT ATAACA TTGGATAGC-3' (SEQ ID NO: 59)

Isolation of Other Species Homologs of NPFF1 or NPFF2 Receptor cDNA

A nucleic acid sequence encoding a NPFF1 or NPFF2 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P-labeled oligonucleotide probe corresponding to a fragment of the human or rat NPFF1 or NPFF2 receptors whose sequence is shown in FIGS. 1, 7, 11 and 22A–C to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1, 7, 11 and 22A–C. One may isolate a full-length NPFF1 or NPFF2 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-labeled oligonucleotide probe.

Approach #3: 3' and 5' RACE may be utilized to generate PCR products from cDNA derived from the species of interest expressing NPFF1 or NPFF2 which contain the additional sequence of NPFF1 or NPFF2. These RACE PCR products may then be sequenced to determine the additional sequence. This new sequence is then used to design a forward PCR primer in the 5'UT and a reverse primer in the 3'UT. These primers are then used to amplify a full-length NPFF1 or NPFF2 clone from cDNA.

Examples of other species include, but are not limited to, mouse, dog, monkey, hamster and guinea pig.

Cell Culture

COS-7 cells are grown on 150 mm plates in DMEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells are trypsinized and split 1:6 every 3–4 days.

Human embryonic kidney 293 cells (HEK-293 cells) are grown on 150 mm plates in DMEM with supplements (10% bovine calf serum, 4 mM glutamine, 100 units/ml penicillin/100 μg/ml streptomycin) at 37° C., 5% $CO_2$. Stock plates of 293 cells are trypsinized and split 1:6 every 3–4 days.

Mouse fibroblast LM(tk–) cells are grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of LM(tk–) cells are trypsinized and split 1:10 every 3–4 days.

Chinese hamster ovary (CHO) cells were grown on 150 mm plates in HAM's F-12 medium with supplements (10% bovine calf serum, 4 mM L-glutamine and 100 units/ml penicillin/100 μg/ml streptomycin) at 37° C., 5% $CO_2$. Stock plates of CHO cells are trypsinized and split 1:8 every 3–4 days.

Mouse embryonic fibroblast NIH-3T3 cells are grown on 150 mm plates in Dulbeccols Modified Eagle Medium (DMEM) with supplements (10% bovine calf serum, 4 mM glutamine, 100 units/ml penicillin/100 mg/ml streptomycin) at 37° C., 5% CO2. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ M medium supplemented with L-Glutamine, also at 27° C., no $CO_2$.

Transient Transfection

Receptors studied may be transiently transfected into COS-7 cells by the DEAE-dextran method using 1 μg of DNA/$10^6$ cells (Cullen, 1987). In addition, Schneider 2 Drosophila cells may be cotransfected with vectors containing the receptor gene under control of a promoter which is active in insect cells, and a selectable resistance gene, eg., the G418 resistant neomycin gene, for expression of the polypeptides disclosed herein.

Stable Transfection

DNA encoding the human receptor disclosed herein may be co-transfected with a G-418 resistant gene into the human embryonic kidney 293 cell line by a calcium phosphate transfection method (Cullen, 1987). Stably transfected cells are selected with G-418.

Membrane Preparations

LM(tk–) cells stably transfected with the DNA encoding the human receptor disclosed herein may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/ml in suspension media (10% bovine calf serum, 10% 10×Medium 199 (Gibco), 9 mM $NaHCO_3$, 25 mM glucose, 2 mM L-glutamine, 100 units/ml penicillin/100 μg/ml streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours.

Generation of Baculovirus

The coding region of DNA encoding the human receptors disclosed herein may be subcloned into pBlueBacIII into existing restriction sites or sites engineered into sequences 5' and 3' to the coding region of the polypeptides. To generate baculovirus, 0.5 μg of viral DNA (BaculoGold) and 3 μg of DNA construct encoding a polypeptide may be co-transfected into 2×$10^6$ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Radioligand Binding Assays

Cells may be screened for the presence of endogenous human receptor using radioligand binding or functional assays (described in detail in the following experimental description). Cells with either no or a low level of the endogenous human receptors disclosed herein present may be transfected with the human receptors.

Transfected cells from culture flasks are scraped into 5 ml of 20 mM Tris-HCl, 5mM EDTA, pH 7.5, and lysed by sonication. The cell lysates are centrifuged at 1000 rpm for 5 min. at 4° C., and the supernatant is centrifuged at 30,000×g for 20 min. at 4° C. The pellet is suspended in binding buffer (50 mM Tris-HCl, 60 mM NaCl, 1 mM MgCl, 33 $\mu$M EDTA, 33 $\mu$M EGTA at pH 7.4 supplemented with 0.2% BSA, 2 $\mu$g/ml aprotinin, and 20 $\mu$M bestatin). Optimal membrane suspension dilutions, defined as the protein concentration required to bind less than 10% of the added radioligand, are added to 96-well polpropylene microtiter plates containing $^3$H-labeled compound, unlabeled compounds, and binding buffer to a final volume of 250 $\mu$l. In equilibrium saturation binding assays membrane preparations are incubated in the presence of increasing concentrations of [$^3$H]-labeled compound. The binding affinities of the different compounds are determined in equilibrium competition binding assays, using [$^{125}$I]-labeled compound in the presence of ten to twelve different concentrations of the displacing ligands. Competition assay: 50 pM radioligand, 10–12 points. Binding reaction mixtures are incubated for 2 hr at 25° C., and the reaction stopped by filtration through a double layer of GF filters treated with 0.11 polyethyleneimine, using a cell harvester. Wash buffer: 50 mM Tris-HCl, 0.1% BSA. Radioactivity may be measured by scintillation counting and data are analyzed by a computerized non-linear regression program. Non-specific binding is defined as the amount of radioactivity remaining after incubation of membrane protein in the presence of 1 $\mu$M final concentration unlabeled. Protein concentration may be measured by the Bradford method using Bio-Rad Reagent, with bovine serum albumin as a standard.

Functional Assays

Cells may be screened for the presence of endogenous mammalian receptor using radioligand binding or functional assays (described in detail in the above or following experimental description, respectively) Cells with no or a low level of endogenous receptor present may be transfected with the mammalian receptor for use in the following functional assays.

A wide spectrum of assays can be employed to screen for the presence of receptor ligands. These range from traditional measurements of phosphatidyl inositol, cAMP, $Ca^{++}$, and $K^-$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Cyclic AMP (cAMP) Formation Assay

The receptor-mediated inhibition of cyclic AMP (cAMP) formation may be assayed in transfected cells expressing the mammalian receptors. Cells are plated in 96-well plates and incubated in Dulbecco's phosphate buffered saline (PBS) supplemented with 10 mM HEPES, 5 mM theopiylline, 2 $\mu$g/ml aprotinin, 0.5 mg/ml leupeptin, and 10 $\mu$g/ml phosphoramidon for 20 min at 37° C., in 5% $CO_2$. Test compounds are added and incubated for an additional 10 min at 37° C. The medium is then aspirated and the reaction stopped by the addition of 100 mM HCl. The plates are stored at 4° C. for 15 min, and the cAMP content in the stopping solution measured by radioimmunoassay. Radioactivity may be quantified using a gamma counter equipped with data reduction software.

Arachidonic Acid Release Assay

Cells stably transfected with the mammalian receptor are seeded into 96 well plates and grown for 3 days in HAM's F-12 with supplements. $^3$H-arachidonic acid (specific activity=0.75 $\mu$Ci/ml) is delivered as a 100 $\mu$L aliquot to each well and samples were incubated at 37° C., 5% $CO_2$ for 18 hours. The labeled cells are washed three times with 200 $\mu$L HAM's F-12. The wells are then filled with medium (200 $\mu$L) and the assay is initiated with the addition of peptides or buffer (22 $\mu$L). Cells are incubated for 30 min at 37° C., 5% $CO_2$. Supernatants are transferred to a microtiter plate and evaporated to dryness at 75° C. in a vacuum oven. Samples are then dissolved and resuspended in 25 $\mu$L distilled water. Scintillant (300 $\mu$L) is added to each well and samples are counted for $^3$-H in a Trilux plate reader. Data are analyzed using nonlinear regression and statistical techniques available in the GraphPAD Prism package (San Diego, Calif.).

Intracellular Calcium Mobilization Assay

The intracellular free calcium concentration may be measured by microspectroflourometry using the fluorescent indicator dye Fura-2/AM (Bush et al, 1991). Stably transfected cells are seeded onto a 35 mm culture dish containing a glass coverslip insert. Cells are washed with HBS and loaded with 100 $\mu$L of Fura-2/AM (10 $\mu$M) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Alternatively, cells expressing the mammalian receptor DNA are plated in 96-well plates and grown to confluence. Cells are incubated with a cell permeant fluorescent calcium indicator such as, but not restricted to, Fluo-3/AM. After washing with HBS to remove the Fluo-3/AM solution, cells are equilibrated for 20 min. The fluorescence emission due to intracellular calcium mobilization elicited by agonists of the expressed mammalian receptor, is determined with a fluorescence imaging plate reader (FLIPR, Molecular Devices Corporation, Sunnyvale, Calif.).

Phosphoinositide Metabolism Assay

Cells stably expressing the mammalian receptor cDNA are plated in 96-well plates and grown to confluence. The day before the assay the growth medium is changed to 100 $\mu$l of medium containing 1 serum and 0.5 $\mu$Ci [$^3$H]myo-inositol, and the plates are incubated overnight in a $CO_2$ incubator (5% $CO_2$ at 37° C.). Alternatively, arachidonic acid release may be measured if [$^3$H]arachidonic acid is substituted for the [$^3$H]myo-inositol. Immediately before the assay, the medium is removed and replaced by 200 $\mu$L of PBS containing 10 mM LiCl, and the cells are equilibrated with the new medium for 20 min. During this interval cells are also equilibrated with the antagonist, added as a 10 $\mu$L aliquot of a 20-fold concentrated solution in PBS. The [3H]inositol-phosphates accumulation from inositol phospholipid metabolism may be started by adding 10 $\mu$L of a solution containing the agonist. To the first well 10 μL may be added to measure basal accumulation, and 11 different concentrations of agonist are assayed in the following 11 wells of each plate row. All assays are performed in duplicate by repeating the same additions in two consecutive plate rows. The plates are incubated in a $CO_2$ incubator for 1 hr. The reaction may be terminated by adding 15 μL of 50% v/v trichloroacetic acid (TCA), followed by a 40 min. incubation at 4° C. After neutralizing TCA with 40 μL of 1 M Tris, the content of the wells may be transferred to a Multiscreen HV filter plate (Millipore) containing Dowex AG1-X8 (200–400 mesh, formate form). The filter plates are prepared adding 200 μL of Dowex AG1-X8 suspension (506 v/v, water: resin) to each well. The filter plates are placed on a vacuum manifold to wash or elute the resin bed. Each well is washed 2 times with 200 μL of water, followed by 2×200 μL of 5 mM sodium tetraborate/60 mM ammonium formate. The [$^3$H]IPs are eluted into empty 96-well plates with 200 μL of 1.2 M ammonium formate/0.1 formic acid. The content of the wells is added to 3 ml of scintillation cocktail, and the radioactivity is determined by liquid scintillation counting.

GTPγS Functional Assay

Membranes from cells transfected with the mammalian receptors are suspended in assay buffer (50 mM Tris, 100 mM NaCl, 5 mM $MgCl_2$, pH 7.4) supplemented with 0.1% BSA, 0.1% bacitracin and 10 μM GDP. Membranes are incubated on ice for 20 minutes, transferred to a 96-well Millipore microliter GF/C filter plate and mixed with GTPγ-LS (e.g., 250,000 cpm/sample, specific activity ~1000 Ci/mmol) plus or minus GTPγS (final concentration=100 μM). Final membrane protein concentration=90 μg/ml. Samples are incubated in the presence or absence of porcine galanin (final concentration=1 μM) for 30 min. at room temperature, then filtered on a Millipore vacuum manifold and washed three times with cold assay buffer. Samples collected in the filter plate are treated with scintillant and counted for $^{35}$S in a Trilux (Wallac) liquid scintillation counter. It is expected that optimal results are obtained when the mammalian receptor membrane preparation is derived from an appropriately engineered heterologous expression system, i.e., an expression system resulting in high levels of expression of the mammalian receptor and/or expressing G-proteins having high turnover rates (for the exchange of GDP for GTP). GTPYS assays are well-known in the art, and it is expected that variations on the method described above, such as are described by e.g., Tian et al. (1994) or Lazareno and Birdsall (1993), may be used by one of ordinary skill in the art.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (Gq and G11) produce diacylglycerol (DAG) as a consequence of phosphatidyl inositol hydrolysis. DAG activates protein kinase C which in turn phosphorylates MAP kinase. MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the mitogen and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the mitogen and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatrography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of a G protein coupled receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^3$H-thymidine at specific activities ranging from 1 to 10 uCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherant cells are fixed in MeOH or TCA, washed in water, and solubilized in 0.05% deoxycholate/0.1 N NaOH. The soluble extract is transferred to scintillation vials and counted for $^3$H by liquid scintillation counting.

Promiscuous Second Messenger Assays

It is possible to coax receptors of different functional classes to signal through a pre-selected pathway through the use of promiscuous $G_\alpha$ subunits. For example, by providing a cell based recetpor assay system with an endogenously supplied promiscuous $G_\alpha$ subunit such as $G_{\alpha16}$ or a chimeric $G_\alpha$ subunit such as $G_{\alpha zq}$, a GPCR, which might normally prefer to couple through a specific signaling pathway (e.g., $G_g$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha16}$ and/or $G_{\alpha qz}$ this would involve activation of the $G_q$ pathway and production of the second messenger phosphotidyl inositol.

Through the use of similar strategies and tools, it is possible to bias receptor signaling through pathways producing other second messengers such as $Ca^{++}$, cAMP, and $K^+$ currents, for example.

Microphysiometric Measurement of Receptor Mediated Extracellular Acidification Rates Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway.

General guidelines for transient receptor expression, cell preparation and microphysiometric recording are described elsewhere (Salon, J. A. and Owicki, J. A., 1996). Receptors and/or control vectors are transiently expressed in CHO-K1 cells, by liposome mediated transfection according to the manufacturers recommendations (LipofectAMINE, GibcoBRL, Gaithersburg, Md.), and maintained in Ham's F-12 complete (10' serum). A total of 10 $\mu$g of DNA is used to transfect each 75 $cm^2$ flask which had been split 24 hours prior to the transfection and judged to be 70–80% confluent at the time of transfection. 24 hours post transfection, the cells are harvested and $3 \times 10^5$ cells seeded into microphysiometet capsules. Cells are allowed to attach to the capsule membrane for an additional 24 hours; during the last 16 hours, the cells are switched to serum-free F-12 complete to minimize ill-defined metabolic stimulation caused by assorted serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 $\mu$l/min flow rate, with a 2 min total pump cycle which includes a 30 sec flow interrruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 $\mu$M final concentration. Follow up experiments to examine dose-dependency of active compounds is then done by sequentially challenging he cells with a drug concentration range that exceeds the amount needed to generate responses ranging from threshold to maximal levels. Peptides included in the microphysiometric screen included rat NPFF (FLFQPQRF-NH2) (SEQ ID NO: 45) and rat A-18-F-amide (AGEGLSSPFWSLAAPQRF-NH2) (SEQ ID NO: 46). Ligand samples are then washed out and the acidification rates reported are expressed as a percentage increase of the peak response over the baseline rate observed just prior to challenge.

Receptor/G protein Co-transfection Studies

A strategy for determining whether NPFF can couple preferentially to selected G proteins involves co-transfection of NPFF receptor cDNA into a host cell together with the cDNA for a G protein alpha sub-unit. Examples of G alpha sub-units include members of the $G\alpha i/G\alpha o$ class (including $G\alpha t2$ and $G\alpha z$), the $G\alpha q$ class, the $G\alpha s$ class, and the $G\alpha 12/13$ class. A typical procedure involves transient transfection into a host cell such as COS-7. Other host cells may be used. A key consideration is whether the cell has a downstream effector (a particular adenylate cyclase, phospholipase C, or channel isoform, for example) to support a functional response through the G protein under investigation. G protein beta gamma sub-units native to the cell are presumed to complete the G protein heterotrimer; otherwise specific beta and gamma sub-units may be co-transfected as well. Additionally, any individual or combination of alpha, beta, or gamma subunits may be co-transfected to optimize the functional signal mediated by the receptor.

The receptor/G alpha co-transfected cells are evaluated in a binding assay, in which case the radioligand binding may be enhanced by the presence of the optimal G protein coupling or in a functional assay designed to test the receptor/G protein hypothesis. In one example, the NPFF receptor may be hypothesized to inhibit cAMP accumulation through coupling with G alpha sub-units of the $G\alpha i/G\alpha o$ class. Host cells co-transfected with the NPFF receptor and appropriate G alpha sub-unit cDNA are stimulated with forskolin +/– NPFF agonist, as described above in cAMP methods. Intracellular cAMP is extracted for analysis by radioimmunoassay. Other assays may be substituted for cAMP inhibition, including $GTP\gamma^{35}S$ binding assays and inositol phosphate hydrolysis assays. Host cells transfected with NPFF minus G alpha or with G alpha minus NPFF would be tested simutaneously as negative controls. NPFF receptor expression in transfected cells may be confirmed in $^{125}I$-NPFF protein binding studies using membranes from transfected cells. G alpha expression in transfected cells may be confirmed by Western blot analysis of membranes from transfected cells, using antibodies specific for the G protein of interest.

The efficiency of the transient transfection procedure is a critical factor for signal to noise in an inhibitory assay, much more so than in a stimulatory assay. If a positive signal present in all cells (such as forskolin-stimulated cAMP accumulation) is inhibited only in the fraction of cells successfully transfected with receptor and G alpha, the signal to noise ratio will be poor. One method for improving the signal to noise ratio is to create a stably transfected cell line in which 100% of the cells express both the receptor and the G alpha subunit. Another method involves transient co-transfection with a third cDNA for a G protein-coupled receptor which positively regulates the signal which is to be inhibited. If the co-transfected cells simultaneously express the stimulatory receptor, the inhibitory receptor, and a requisite G protein for the inhibitory receptor, then a positive signal may be elevated selectively in transfected cells using a receptor-specific agonist. An example involves co-transfection of COS-7 cells with 5-HT4, NPFF1, and a G alpha sub-unit. Transfected cells are stimulated with a 5-HT4 agonist +/– NPFF1 protein. Cyclic AMP is expected to be elevated only in the cells also expressing NPFF1 and the G alpha subunit of interest, and a NPFF-dependent inhibition may be measured with an improved signal to noise ratio.

It is to be understood that the cell lines described herein are merely illustrative of the methods used to evaluate the binding and function of the mammalian receptors of the present invention, and that other suitable cells may be used in the assays described herein.

Electrophysiology

Methods for Recording Currents in Xenopus Oocytes

Oocytes were harvested from *Xenopus laevis* and injected with mRNA transcripts as previously described (Quick and Lester, 1994; Smith et al.,1997). NPFF receptors and $G\alpha_{q/z}$ chimera synthetic RNA transcripts were synthesized using the T7 polymerase ("Message Machine," Ambion) from linearized plasmids or PCR products containing the complete coding region of the genes. Oocytes were injected with 10 ng NPFF receptors synthetic RNA and incubated for 3–8 days at 17 degrees. Three to eight hours prior to recording, oocytes were injected with 500 pg $G\alpha_{q/z}$ mRNA in order to observe coupling to $Ca^{++}$ activated $Cl^-$ currents. Dual electrode voltage clamp (Axon Instruments Inc.) was performed using 3 M KCl-filled glass microelectrodes having resistances of 1–2 Mohm. Unless otherwise specified, oocytes were voltage clamped at a holding potential of –80 mV. During recordings, oocytes were bathed in continuously flowing (1–3 ml/min) medium containing 96 MM NaCl, 2 mM KCl, 1.8 mM $CaCl_2$, 1 mM $MgCl_2$, and 5 mM HEPES, pH 7.5 (ND96). Drugs were applied either by local perfusion from a 10 ml glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifiers (GIRK1 and GIRK4, U.S. Pat. Nos. 5,734,021 and 5,728,535). Genes encoding G-protein inwardly rectifying $K^+$ (GIRK) channels 1 and 4 (GIRK1 and GIRK4) may be obtained by PCR using the published sequences (Kubo et al., 1993; Dascal et al., 1993; Krapivinsky et al., 1995 and 1995b) to derive appropriate 5' and 3' primers. Human heart cDNA may be used as template together with appropriate primers.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying test compound in ND96 solution to oocytes previously injected with mRNA for the mammalian receptor and observing inward currents at a holding potential of –80 mV. The appearance of currents that reverse at –25 mV and display other properties of the $Ca^{++}$-activated $Cl^-$ (chloride) channel is indicative of mammalian receptor-activation of PLC and release of IP3 and intracellular $Ca^{++}$. Such activity is exhibited by GPCRs that couple to $G_q$.

Measurement of inwardly rectifying $K^+$ (potassium) channel (GIRK) activity may be monitored in oocytes that have been co-injected with mRNAs encoding the mammalian receptor, GIRK1, and GIRK4. The two GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the two GIRK subunits are tested for test compound responsivity by measuring $K^+$ currents in elevated $K^+$ solution containing 49 mM $K^-$. Activation of inwardly rectifying currents that are sensitive to 300 $\mu$M $Ba^{++}$ signifies the mammalian receptor coupling to a $G_i$ or $G_o$ pathway in the oocytes.

Localization of mRNA Coding for Rat NPFF1 Receptors

Development of probes for NPFF1: To facilitate the production of radiolabeled, antisense RNA probes a fragment of the gene encoding rat NPFF1 was subcloned into a plasmid vector containing RNA polymerase promotor sites. The full length cDNA encoding the rat NPFF1 was digested with Sph I (nucleotides 766–1111), and this 345 nucleotide fragment was cloned into the Sph I site of pGEM 3z, containing both sp6 and T7 RNA polymerase promotor sites. The construct was sequenced to confirm sequence identity and orientation. To synthesize antisense strands of RNA, this construct was linearized with Hind III and T7 RNA polymerase was used to incorporate radiolabeled nucleotide as described below.

A probe coding for the rat glyceraldehyde 3-phosphate dehydrogenase (GAPDH) gene, a constitutively expressed protein, was used concurrently. GAPDH is expressed at a relatively constant level in most tissue and its detection is used to compare expression levels of the rat NPFF1 receptors genes in different regions.

Synthesis of probes: NPFF1 and GAPDH cDNA sequences preceded by phage polymerase promoter sequences were used to synthesize radiolabeled riboprobes. Conditions for the synthesis of riboprobes were: 0.25–1.0 $\mu$g linearized DNA plasmid template, 1.5 $\mu$l of ATP, GTP, UTP (10 mM each), 3 $\mu$l dithiothreitol (0.1 M), 30 units RNAsin RNAse inhibitor, 0.5–1.0 $\mu$l (15–20 units/$\mu$l) RNA polymerase, 7.0 $\mu$l transcription buffer (Promega Corp.), and 12.5 $\mu$l $\alpha^{32}$P-CTP (specific activity 3,000 Ci/mmol). 0.1 mM CTP (0.02–1.0 $\mu$l) was added to the reactions, and the volumes were adjusted to 35 $\mu$l with DEPC-treated water. Labeling reactions were incubated at 37° C. for 60 minutes, after which 3 units of RQ1 RNAse-free DNAse (Promega Corp.) were added to digest the template. Riboprobes were separated from unincorporated nucleotides using Microspin S-300 columns (Pharmacia Biotech). TCA precipitation and liquid scintillation spectrometry were used to measure the amount of label incorporated into the probe. A fraction of all riboprobes synthesized was size-fractionated on 0.25 mm thick 7M urea, 4.5% acrylamide sequencing gels. These gels were apposed to screens and the autoradiograph scanned using a phosphorimager (Molecular Dynamics) to confirm that the probes synthesized were full-length and not degraded.

Solution hybridization/ribonuclease protection assay (RPA): For solution hybridization 2.0 $\mu$g of mRNA isolated from tissues were used. Negative controls consisted of 30 $\mu$g transfer RNA (tRNA) or no tissue blanks. All mRNA samples were placed in 1.5 ml microfuge tubes and vacuum dried. Hybridization buffer (40 $\mu$l of 400 mM NaCl, 20 mM Tris, pH 6.4, 2 mM EDTA, in 80% formamide) containing 0.25–2.0 $E^6$ counts of each probe were added to each tube. Samples were heated at 95° C. for 15 min, after which the temperature was lowered to 55° C. for hybridization.

After hybridization for 14–18 hr, the RNA/probe mixtures were digested with RNAse A (Sigma) and RNAse T1 (Life Technologies). A mixture of 2.0 pg RNAse A and 1000 units of RNAse T1 in a buffer containing 330 mM NACl, 10 mM Tris (pH 8.0) and 5 mM EDTA (400 $\mu$l) was added to each sample and incubated for 90 min at room temperature. After digestion with RNAses, 20 $\mu$l of 10% SDS and 50 $\mu$g proteinase K were added to each tube and incubated at 37° C. for 15 min. Samples were extracted with phenol/chloroform:isoamyl alcohol and precipitated in 2 volumes of ethanol for 1 hr at –70° C. Pellet Paint (Novagen) was added to each tube (2.0 $\mu$g) as a carrier to facilitate precipitation. Following precipitation, samples were centrifuged, washed with cold 70% ethanol, and vacuum dried. Samples were dissolved in formamide loading buffer and size-fractionated on a urea/acrylamide sequencing gel (7.0 M urea, 4.5% acrylamide in Tris-borate-EDTA). Gels were dried and apposed to storage phosphor screens and scanned using a phosphorimager (Molecular Dynamics, Sunnydale, Calif.).

RT-PCR

For the detection of of low levels of RNA encoding rat NPFF1, RT-PCR was carried out on mRNA extracted from rat tissue. Reverse transcription and PCR reactions were carried out in 50 $\mu$l volumes using EzrTth DNA polymerase (Perkin Elmer). Primers with the following sequences were used:

RA Rsnorf2/NPFF F1: CTCCTACTACCAACACTC-CTCTCC (SEQ ID NO: 39)

RA RSNORF2/NPFF1 B1: ACGGGTTACGAGCATC-CAG (SEQ ID NO: 40)

These primers will amplify 490 base pair fragment from nucleotide 574 to 1064.

Each reaction contained 0.2 μg mRNA and 0.3 μM of each primer. Concentrations of reagents in each reaction were: 300 μM each of dGTP, DATP, dCTP, dTTP; 2.5 mM Mn(OAc)$_2$; 50 mM Bicine; 115 mM K acetate, 8% glycerol and 5 units EzrTth DNA polymerase. All reagents for PCR (except mRNA and oligonucleotide primers) were obtained from Perkin Elmer. Reactions were carried out under the following conditions: 65° C., 60 min; 94° C., 2 min; (94° C., 1 min; 65° C., 1 min) 35 cycles, 72° C., 10 min. PCR reactions were size fractionated by agarose gel electrophoresis using 10% polyacrylamide. DNA was stained with SYBR Green I (Molecular Probes, Eugene, Oreg.) and scanned on a Molecular Dynamics (Sunnyvale, Calif.) Storm 860 in blue flourescence mode at 450 nM.

Positive controls for PCR reactions consisted of amplification of the target sequence from a plasmid construct, as well as reverse transcribing and amplifying a known sequence. Negative controls consisted of mRNA blanks as well as primer blanks. To confirm that the mRNA was not contaminated with genomic RNA, samples were digested with RNAses before reverse transcription. Integrity of RNA was assessed by amplification of mRNA coding for GAPDH.

Localization of mRNA Coding for NPFF-like Receptors (hNPFF2) using RT-PCR

For the detection of low levels of RNA encoding hNPFF2 RT-PCR was carried out on mRNA extracted from tissue. Reverse transcription and PCR reactions were carried out in 50 μl volumes using EzrTh DNA polymerase (Perkin Elmer). Primers with the following sequences were used:

JB 249: 5'-GATCAGTGGATTGGTCCAGGGAATATC-3' (SEQ ID NO: 41)

JB 250: 5'-CCAGGTAGATGTTGGCAAACAGCAC-3' (SEQ ID NO: 42)

These primers will amplify a 332 base pair fragment from TMIII to TMV.

Each reaction contained 0.1 ug mRNA and o.3 uM of each primer. Concentrations of reagents in each reaction were 300 uM each of dGTP, DATP, dCTP, dTTP, 2.5 mM Mn(OAc)2, 50 mM Bicine, 115 mM potassium acetate, 8% glycerol and 5 units EzrTth DNA polymerase. All reagents for PCR (except mRNA and oligonucleotide primers) were obtained from Perkin Elmer. Reactions were carried out under the following conditions: 65° C. 60 min., 94° C. 2 min, (94° C., 1 min, 65° C. 1 min) 35 cycles, 72° C. 10 min. PCR reactions were size fractionated by gel electrophoresis using 10% polyacrylamide. DNA was stained with SYBR Green I (Molecular Probes, Eugene Oreg.) and scanned on a Molecular Dynamics (Sunnyvale, Calif.) Strom 860 in blue fluorescence mode at 450 nm.

Positive controls for PCR reactions consisted of amplification of the target sequence from a plasmid construct, as well as reverse transcribing and amplifying a known sequence. Negative controls consisted of mRNA blanks and primer blanks. To confirm that the mRNA was not contaminated with genomic DNA, samples were digested with RNAses before reverse transcription. Integrity of RNA was assessed by amplification of mRNA coding for GAPDH.

Localization of mRNA Coding for Human and Rat NPFF Receptors

Materials and Methods

Quantitative RT-PCR using a fluorogenic probe with real time detection: Quantitative RT-PCR using fluorogenic probes and a panel of mRNA extracted from human and rat tissue was used to characterize the localization of NPFF rat and human RNA. This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein) and JOE (6 carboxy-4.5-dichloro-2,7-dimethoxyfluorescein) were the two reporters that were utilized and TAMRA (6-carboxy-4, 7,2,7'-tetramethylrhodamine) was the quencher. As amplification progresses, the labeled oligonucleotide probe hybridizes to the gene sequence between the two oligonucleotides used for amplification. The nuclease activity of Taq, or rTth thermostable DNA polymerases is utilized to cleave the labeled probe. This separates the quencher from the reporter and generates a fluorescent signal that is directly proportional to the amount of amplicon generated. This labeled probe confers a high degree of specificity. Non-specific amplification is not detected as the labeled probe does not hybridize. All experiments were conducted in a PE7700 Sequence Detection System (Perkin Elmer, Foster City Calif.).

Ouantitative RT-PCR: For the detection of RNA encoding NPFF receptors, quantitative RT-PCR was performed on mRNA extracted from tissue. Reverse transcription and PCR reactions were carried out in 50 ul volumes using rtth DNA polymerase (Perkin Elmer). Primers with the following sequences were used:

NPFF1 Human
Forward primer:
NPFF1h-913F 5'-CTGGTCACCGTCTACGCCTT-3' (SEQ ID NO: 60)
Reverse primer:
NPFF1h-1016R 5'-CCGCGGCGGAAGTTCT-3' (SEQ ID NO: 61)
Fluorogenic oligonucleotide probe:
NPFF1h-962T 5'(6-FAM)-ACAGCAGCGCCAACCCCATCAT-(TAMRA) 3' (SEQ ID NO: 62)

NPFF2 Human
Forward primer:
NPFF2h-828F 5'-CCTGATTGTGGCCCTGCT-3' (SEQ ID NO: 63)
Reverse primer:
NPFF2h-916R 5'-CATTTGGAGAAAGGTCAGCGTAG-3' (SEQ ID NO: 64)
Fluorogenic oligonucleotide probe:
NPFF2h-855T 5' (6-FAM)-CTCATGGCTGCCCCTGTGGACTCAAT-(TAMRA) 3' (SEQ ID NO: 65)

NPFF1 Rat
Forward primer:
NPFF1r-412F 5'-GCTGTGGAAAGGTTCCGCT-3' (SEQ ID NO: 66)
Reverse primer:
NPFF1r-474R 5'-CGCCTTCCGAAGGGTCA-3' (SEQ ID NO: 67)
Fluorogenic oligonucleotide probe:

NPFF1r-433T 5'-(6-FAM)-ATCGTGCACCCTTTCCGCGAGAA-(TAMRA)3' (SEQ ID NO: 68)

NPFF2 Rat

Forward primer:

NPFF2r deg-690F 5'-GAGGATCTACACCACCGTGCTATT-3' (SEQ ID NO: 69)

Reverse primer:

NPFF2r deg-776R 5'-GAAGCCCCAATCCTTGCATAC-3' (SEQ ID NO: 70)

Fluorogenic oligonucleotide probe:

NPFF2r-722T 5'-(6-FAM)-TCTACCTGGCTCCACTCTCCCTCATTGTT-(TAMRA)3, (SEQ ID NO: 71)

Using these primer pairs, amplicon length is 103 bp for human NPFF1, 88 bp for human NPFF2, 62 bp for rat NPFF1, and 86 bp for rat NPFF2. Each human RT-PCR reaction contained 50 ng mRNA and each rat RT-PCR reaction contained 100 ng total RNA. Oligonuceotide concentrations were: 500 nM of forward and reverse primers, and 200 nM of fluorogenic probe. Concentrations of reagents in each reaction were: 300 µM each of dGTP; DATP; dCTP; 600 µM UTP; 3.0 mM Mn(OAc)2; 50 mM Bicine; 115 mM potassium acetate, 8% glycerol, 5 units rTth DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotide primers) were obtained from Perkin Elmer (Foster City, Calif.). Reactions were carried using the following thermal cycler profile: 50° C. 2 min., 60° C. 30 min., 95° C. 5 min., followed by 40 cycles of: 94° C., 20 sec., 62° C. 1 min.

Positive controls for PCR reactions consisted of amplification of the target sequence from a plasmid construct when available. Standard curves for quantitation of human and rat NPFF1 and NPFF2 were constructed using RNA extracted from whole brain. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of RNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted a standard curve to obtain relative quantities of NPFF mRNA expression.

Receptor Autoradiographic Experiments Localizing NPFF Receptor Subtypes in the Rat CNS Animals Male Sprague-Dawley rats (Charles Rivers, Rochester, N.Y.) were euthanized using $CO_2$, decapitated, and their brains and peripheral tissues were immediately removed and rapidly frozen on crushed dry ice. Coronal sections of brain tissues were cut at 20 µm using a cryostat, thaw-mounted onto gelatin-coated slides then stored at −20° C. until binding assay.

Materials

[$^{125}$I] [D-Tyr$^1$-(NMe)Phe$^3$]NPFF (specific activity 2200 Ci/mmol was synthesized by iodination with chloramine-T from NEN (Boston, Mass.). BIBP 3226 was from RBI (Natick, Mass.). Frog pancreatic polypeptide (frog PP)(Rana Temporaria) was from Peninsula (Belmont, Calif.), and Neuropeptide FF (NPFF) was from (Bachem, King of Prussia, Pa.).

In Vitro Autoradiography

Tissue sections were allowed to equilibrate to room temperature for one hour. Sections were then incubated at 25° C. for 2 hours in 50 mM Tris-HCl buffer, pH 7.4, containing 1 mM NaCl, 1 mM $MgCl_2$, 0.1% Bovine Serum Albumin (Boehringer Mannheim, Indianapolis, Ind.) and 0.05 nM [$^{125}$I] [D-Tyr$^1$-(NMe) Phe$^3$]NPFF. Adjacent sections were incubated in the presence of 300 nM BIBP 3226 to selectively displace binding to NPFF1 or 300 nM frog PP to selectively displace binding to NPFF2. Nonspecific binding was determined by including 1 µM unlabeled NPFF in the incubation buffer. Sections were then washed four times, 5 minutes each, in 4° C,. 50 mM Tris-buffer pH 7.4 then rapidly dipped in ice-cold distilled water to remove salts. Tissues were then dried under a stream of cold air. The sections were subsequently apposed together with $^{125}$I-plastic standard scales, to Kodak BIOMAX MS Scientific Imaging Film (Eastman Kodak Company, Rochester, N.Y.) for three days at room temperature. Films were developed using a Kodak M35 µX-OMAT Processor (Eastman Kodak Company, Rochester, N.Y.). Specific [125I] [D-Tyr$^1$-(NMe) Phe$^3$]NPFF binding to NPFF1 and NPFF2 receptors was interpreted by observation of the remaining optical density on the autoradiogram in the various regions of rat brain in the presence of the appropriate displacers.

In Vivo Experiments

Effects of NPFF on Blood Pressure in Normotensive Rats

It has been demonstrated that the intravenous administration of NPFF produces an increase in mean arterial blood pressure (MAP)(71). The following experiments were designed to determine which subtype of NPFF receptor mediates this effect.

Experimental Methods

Rats were anesthetized with urethane and PE50 cannulae were placed in the femoral artery and vein for blood pressure monitoring and drug administration, respectively. After stabilization, rats were administered 200 µl saline vehicle; the agonists NPFF, frog pancreatic polypeptide (fPP), or the NPY-$Y_1$-selective agonist pLeu, Pro-NPY [(Leu$^{31}$, Pro$^{34}$)-neuropeptide Y (porcine)]; or the NPY-$Y_1$ receptor antagonist BIBP 3226.

Effects of NPFF on the Micturition Reflex in Anesthetized Rats

The effects of compounds on the micturition reflex were assessed in the "distension-induced rhythmic contraction" (DIRC) model in rats. This model of the micturition reflex has been described in previous publications (e.g. 72, 73).

DIRC Model

Female Sprague Dawley rats weighing approximately 300 g were anesthetized with subcutaneous urethane (1.2 g/kg). The trachea was cannulated with PE240 tubing to provide a clear airway throughout the experiment. A midline abdominal incision was made and the left and right ureters were isolated. The ureters were ligated distally (to prevent escape of fluids from the bladder) and cannulated proximally with PE10 tubing. The incision was closed using 4-0 silk sutures, leaving the PE10 lines routed to the exterior for the elimination of urine. The bladder was canulated via the transurethral route using PE50 tubing inserted 2.5 cm beyond the urethral opening. This cannula was secured to the tail using tape and connected to a pressure transducer. To prevent leakage from the bladder, the cannula was tied tightly to the exterior urethral opening using 4-0 silk.

To initiate the micturition reflex, the bladder was first emptied by applying pressure to the lower abdomen, and then filled with normal saline in 100 µl increments (maximum=2 ml) until spontaneous bladder contractions occurred (typically 20–40 mmHg at a rate of one contraction every 2 to 3 minutes. Once a regular rhythm was established, vehicle (saline) or test compounds were administered intravenously to examine their effects on bladder activity. The effect of a compound which inhibited the micturition reflex was expressed as its "disappearance time", defined as the time between successive bladder contractions in the presence of the test compound minus the time between contractions before compound administration.

Results and Discussion

Cloning and Sequencing
rNPFF1 and hNPFF1

100 ng genomic DNA was subjected to MOPAC PCR with two degenerate primers designed based on the sixth and seventh transmembrane domains of over 180 receptors from the rhodopsin superfamily of G protein-coupled receptors. Two products from this reaction, MPR3-RGEN-31 and MPR3-RGEN-45 were found to be identical clones of a novel DNA sequence not found in the Genbank databases (Genembl, STS, EST, GSS), which had 30–40% amino acid identity with the known receptors dopamine D2, orexin 1, GALR1, angiotensin 1B and 5HT-2b. This novel clone was given the name SNORF2.

The full-length SNORF2 sequence was acquired by screening rat hypothalamic cDNA libraries by PCR using specific SNORF2 oligonucleotide primers. Pools of the rat hypothalamic cDNA library "I" were screened by PCR with SNORF2-specific primers JAB208 and JAB209. This screen yielded a positive pool I36. Successive PCR screening of sub-pools of this pool followed by high stringency hybridization of isolated colonies from the positive sub-pool I36–17 with the SNORF2-specific oligonucleotide probe indicated that the isolated clone I36E-17-1B-1 contained at least a partial clone of SNORF2. Sequencing of I36E-17-1B-1 revealed that this insert contained the coding region from the TMIII-TMIV loop through the stop codon, including some 3' untranslated sequence. From this sequence, a new forward primer, JAB221, was designed in TMV. PCR screening of a second rat hypothalamic cDNA library "J" with primers JAB221 and JAB209, and subsequent colony hybridization with the JAB211 probe on a low complexity positive sub-pool resulted in the isolation of a SNORF2 clone J-13-16-A1. This clone contained the full-length coding sequence of SNORF2 (1296 bp) with approximately 200 bp 5'untranslated sequence and 1.3 kb 3' untranslated sequence. The nucleotide sequence of SNORF2 and its translated amino acid sequence are represented in FIGS. 1 and 2, respectively. As shown in FIG. 1, SNORF2 contains two potential initiating methionines upstream of TMI.

Figure 5:
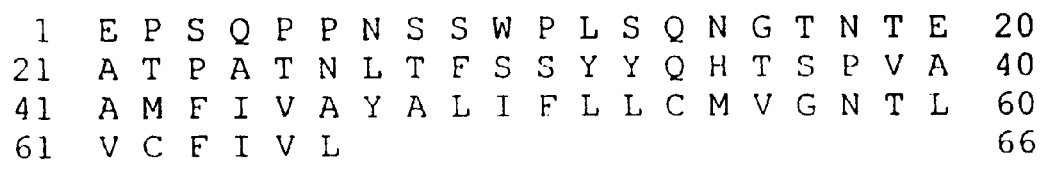

Hydophobicity (Kyte-Doolittle) analysis of the amino acid sequence of the full-length clone indicates the presence of seven hydrophobic regions, which is consistent with the seven transmembrane domains of a G protein-coupled receptor. The seven expected transmembrane domains are mapped out in FIG. 3. A comparison of nucleotide and peptide sequences of SNORF2 with sequences contained in the Genbank/EMBL/SwissProtplus databases reveals that the amino acid sequence of this clone is most related to the orexin 1 and 2 receptors (45% and 40% identity, respectively) as well as the neuropeptide Y receptors Y1, Y2 and Y4 (~30% identity). Further homology analysis of SNORF2 against the Synaptic Pharmaceutical Corporation in-house database revealed that SNORF2 has a very high degree of identity with a proprietary Synaptic Pharmaceutical Corporation human partial GPCR clone named PLC29b (85% nucleotide identity, 93% amino acid identity). PLC29b was originally isolated from a human genomic library using oligonucleotide probes for NPY4, and includes part of the amino terminus and TMs I to IV. Partial nucleotide and amino acid sequence of PLC29b (human SNORF2) is represented in FIGS. 4 and 5, respectively. Based on sequence similarity, PLC29b appears to be a partial clone of the human homologue of SNORF2. Therefore, this human homolog of SNORF2 has been named hNPFF1. A GAP alignment demonstrating the high homology between these species homologues is represented in FIG. 6. SNORF2 has several potential protein kinase C (PKC) phosphorylation motifs throughout its amino acid sequence: threonine 154 in the second intracellular loop, threonine 263 and serine 264 in the third intracellular loop, and serine 363 in the intracellular carboxy-terminal tail. It also has four potential N-linked glycosylation sites at asparagines 10 and 18 in the amino-terminal tail and at asparagines 113 and 195 in the first and second extracellular loops, respectively.

hNPFF2

In analyzing the sequence of rNPFF1 and its homology to other sequences in GenBank, a 532 bp EST with the accession number AA449919 was identified which had a high degree of identity to rNPFF1. The translation of this sequence indicated that it coded for the region between the first extracellular loop and the beginning of the sixth transmembrane domain of a G protein-coupled receptor (GPCR). Although AA449919 was documented as being similar to the *Drosophila melanogaster* NPY receptor (accession number P25931), it was found that the amino acid sequence encoded by this EST was much more similar to NPFF1. The predicted amino acid sequence of AA449919 and rNPFF1 are 50% identical, while the amino acid sequence of the Drosophila NPY receptor is only 31% identical to the translation of AA449919. Because of the high degree of identity between AA449919 and rNPFF1, AA449919 was given the name hNPFF2, representing a member of a novel family of NPFF receptors of which there is currently only one member, NPFF1.

The full length sequence of NPFF-like (hNPFF2) was acquired by 5'/3' RACE using human spleen cDNA as a template, as described above, demonstrating that the coding region of hNPFF-like (hNPFF2) is 1260 bp, coding for a protein of 420 amino acids. Sequencing of clones from several independent PCR reactions using spleen, heart, and spinal cord cDNA as templates and subsequent alignment of these clones with Sequencher 3.0 was used to confirm the sequence of hNPFF-like (hNPFF2). The full-length nucleotide sequence of human NPFF2 is shown in FIG. 7, and its translated amino acid sequence is shown in FIG. 8. The seven putative transmembrane domains of hNPFF-like (hNPFF2) are defined in FIG. 9.

Like the original EST AA449919, the amino acid sequence encoded by the full-length DNA sequence of hNPFF2 is most similar to rNPFF1 (48% identity), as shown in the GAP alignment between the two receptors in FIG. 10. The next-best matches in SWPLUS to full-length hNPFF2 are the Drosophila NPYR (accession number P25931, 34% identity) and TLR2 (accession number P30975, 32% identity), human orexin 1 and 2 receptors (043613, 31% and 043614, 29%, respectively) and human NPY1 and Y4 receptors (P25929, 31% and P50391, 32%, respectively). A Blast search of the EST database using the full-length nucleotide sequence of hNPFF2 revealed an EST (Accession number AA449920) that is identical to hNPFF2 from the end of TM7 through the stop codon. ESTs AA44919 and AA44920 are the same clone sequenced from 5' end or the 3' end, respectively. hNPFF2 contains several potential N-linked glycosylation sites. The first three sites, asparagines 8, 20, and 31 are in the N-terminal extracellular domain. Another potential N-linked glycosylation site, at position 198, is in the second extracellular loop. This receptor also contains one potential PKC phosphorylation site at threonine 156 in the second intracellular loop, and two potential PKC phosphorylation sites in the third intracellular loop at threonine 254 and serine 266.

hNPFF1

The sequence of hNPFF1 from the initiating methionine to TMIV was determined to be present in a partial clone, plc29b, found in a Synaptic Pharmaceutical Corporation in-house database. Additional sequence, including TMIV through the stop codon, was determined by sequencing a vector-anchored PCR product from a human cosmid library clone identified by hybridization with a $^{32}$P-labeled probe (BB609) corresponding to the II/III loop of plc29b. Next, a human spinal cord library was screened by PCR using primers designed against the partial hNPFF1 sequence, BB729 and BB728. One positive pool, W4, was subdivided and a positive sub-pool was screened by colony hybridization with a $^{32}$P-labeled probe from TMII of hNPFF1, BB676. Plasmid DNA was isolated for clone W4-18-4, renamed BO98, and DNA sequencing revealed that it was full-length but in the wrong orientation for expression in the expression vector pEXJ. To obtain a full-length hNPFF1 construct in the correct orientation, BO98 was amplified with BB757 and BB758, and the resulting product ligated into pcDNA3.1 and transformed into DH5α cells. The sequence of one of these transformants was identical to the hNPFF1 sequence previously determined from the consensus of BO98 and the two cosmid clones. This human NPFF1 construct in pcDNA3.1 in the correct orientation was renamed B0102.

The hNPFF1 clone contains an open reading frame with 1293 nucleotides and predicts a protein of 430 amino acids (FIGS. 11 and 12). Seven transmembrane domains predicted by hydrophobicity analysis are indicated in FIG. 13. The sequence of hNPFF1 was determined to be most similar to the rat NPFF1 (86% nucleotide identity, 87% amino acid identity) and human NPFF2 (56% nucleotide identity, 49% amino acid identity (FIG. 14)). The human NPFF1 receptor also shares homology with human orexin, (53% nucleotide identity, 35% amino acid identity), human orexin$_2$ (43% nucleotide identity, 33% amino acid identity), human NPY$_2$ (47% nucleotide identity, 31% amino acid identity), human CCK$_A$ (46% nucleotide identity, 32% amino acid identity), and human CCK$_B$ (46% nucleotide identity, 26% amino acid identity).

Isolation of the Rat NPFF2 Homologue

A fragment of the rat homologue of NPFF2, from TMIV to TMVI, was amplified from rat genomic DNA, rat hypothalamic cDNA and rat spinal cord cDNA by reduced stringency PCR using oligonucleotide primers designed against the human NPFF2. Additional sequence was obtained by amplifying rat spinal cord cDNA under reduced stringency using PCR primers designed against the rat NPFF2 fragment along with primers corresponding to the NH2- and COOH-termini of the human NPFF2 receptor. This resulted in the identification of a rat NPFF2 fragment from TMI to TMVII.

The remaining sequence of the rat NPFF2 receptor was acquired by screening a rat genomic phage library with an oligonucleotide probe corresponding to the second extracellular loop and TMV of rat NPFF2. Southern blot analysis of three isolated plaques with this same probe identified a 3.5 kb fragment which was subcloned and sequenced, revealing the COOH terminus and some 3'UT. A subsequent Southern blot analysis using an oligonucleotide probe corresponding to TMI of rat NPFF2 identified a 2.1 kb fragment which was subcloned and sequenced, revealing the NH$_2$ terminus and some 5'UT.

The full-length rat NPFF2 clone was amplified from rat spinal cord cDNA using a sense PCR primer corresponding to the 5'UT and an antisense primer corresponding to the 3'UT, and subcloned into pcDNA3.1. Sequencing of 5 independent PCR products revealed an open reading frame of 1251 bp that is predicted to encode a protein of 417 amino acids (FIGS. 22A–C and 23A–B, respectively). In addition, several potential allelic variations were identified and verified by sequencing additional genomic DNA PCR products. The allelic variations are at the following nucleotide positions (relative to FIGS. 22A–C): position 913 can be either G or A, position 949 can be either C or T, position 955 can be either C or T, and position 1151 can be either C or T. None of these variants alter the predicted amino acid sequence. One construct, whose nucleotide sequence is shown in FIGS. 22A–C was renamed pcDNA3.1-rNPFF2-f.

Hydophobicity (Kyte-Doolittle) analysis of the amino acid sequence of the full-length clone indicates the presence of seven hydrophobic regions, which is consistent with the seven transmembrane domains of a G protein-coupled receptor. The seven expected transmembrane domains are indicated in FIGS. 23A–B. A comparison of nucleotide and peptide sequences of rat rNPFF2 with sequences contained in the Genbank, EMBL and SwissProtPlus databases reveals that the nucleotide sequence of this clone is 81% identical to an orphan GPCR NPGPR (GenBank accession number AF119815), and the amino acid sequence of this clone is most related to orexin-1 and orexin-2 (34% amino acid identities), NPY2 (32% amino acid identity) and GIR (31 amino acid identity). There were no sequences in the Genbank databases (Genembl, STS, EST, GSS, or SwissProt) that were identical to rat NPFF2. The rat and human NPFF2 receptors share 81% nucleotide and 78% amino acid identities (FIG. 24). The rat NPFF2 and rat NPFF1 receptors share 556 nucleotide and 50% amino acid identities (FIG. 25).

Rat NPFF2 has five potential N-linked glycosylation sites, at asparagines 8, 20 and 31 in the amino-terminal tail, at asparagine 198 in the second extracellular loop and at asparagine 324 in the seventh transmembrane domain. It also has three potential protein kinase C (PKC) phosphorylation motifs at threonine 156 in the second intracellular loop, and at threonine 254 and serine 265 in the third intracellular loop. NPFF2 also has two potential casein kinase II phosphorylation sites at threonine 102 in the second transmembrane domain and at serine 403 in the carboxy-terminal tail.

Electrophysiology

NPFF1

Figure 15A:
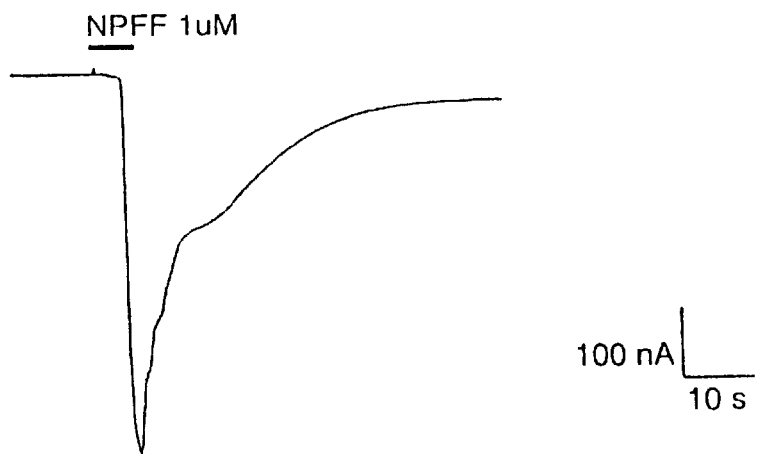
Figure 15B:
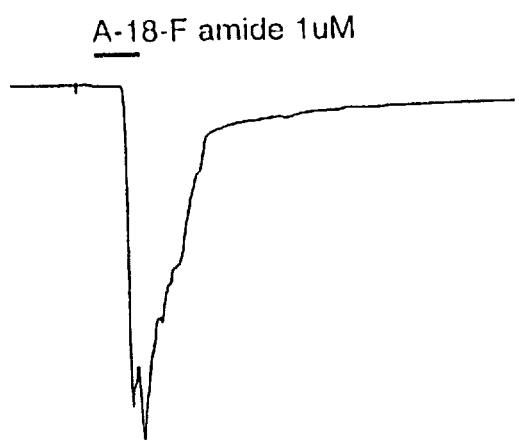
Figure 15C:
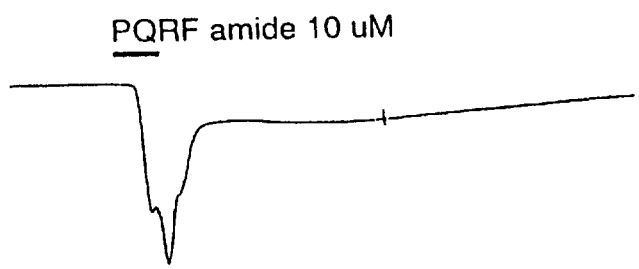

Oocytes injected with both SNORF2 and chimeric Ga$_{q/z}$ synthetic RNAs generated robust inward currents in response to NPFF and the related peptide A-18-F-amide at 1 μM (FIGS. 15A, B). Control oocytes receiving only G-protein synthetic RNA were unresponsive to these peptides. Responses to NPFF were concentration-dependent with a threshold for activation of inward current at 30 nM. The C-terminal tetrapeptide PQRF-amide also elicited responses at a concentration of 10 μM (FIG. 15C). Analogs of NPFF containing a tyrosine residue at the N-terminus or internally including Y-8-F-amide, [tyr$^9$]A-18-F-amide and Y-18-F-amide also displayed activity at 1 μM. Unrelated neuropeptides and other neurotransmitters including melanin concentrating hormone, orexin B, PYY, 5-HT, nociceptin, galanin and CCK failed to activate oocytes injected with the SNORF2 synthetic RNA. The functional responsiveness to NPFF and related peptides strongly suggests that SNORF2 encodes a receptor for neuropeptide FF (NPFF); therefore SNORF2 was renamed NPFF1. Similarly, SNORF2-like was renamed NPFF-like.

Oocytes injected with NPFF1 and not the chimeric G-protein synthetic RNA failed to generated responses to NPFF. This observation supports the hypothesis that NPFF1 couples to G-proteins of the $G\alpha_i/G\alpha_o/G\alpha_z$ class, and by virtue of the N-terminal portion of $G\alpha_{q/z}$, subsequently activates phospholipase C. In oocytes expressing both NPFF1 and $G\alpha_{q/z}$, Cl$^-$ currents were abolished by prior injection of 10 mM EGTA, demonstrating the Ca$^{++}$ dependence of these currents.

NPFF2

Oocytes injected with both the NPFF-like PCR product and chimeric $G\alpha_{q/z}$ synthetic RNAs generated large inward currents in response to 1 μM NPFF (FIG. 16A) A-18-F-amide and PQRF-amide also at 1 μM activated similar inward currents, although the magnitude of currents generated by PGRF-amide were smaller. No activity was observed using FMRF-amide at 1 μM. The unrelated neuropeptides orexin A, NPY, galanin, and neurokinin A at 1 μM also failed to activate responses in oocytes injected with NPFF-like mRNA (FIG. 16B). Oocytes injected with both the NPFF-like plasmid (BO89) and chimeric $G\alpha_{q/z}$ synthetic RNAs also produced robust currents in response to NPFF (FIG. 16C). Based on these results, NPFF-like was renamed NPFF2. Oocytes injected with NPFF2 and not chimeric G-protein mRNA failed to generate responses to NPFF. This observation supports the hypothesis that NPFF2 couples to G-proteins of the $G\alpha_i/G\alpha_o/G\alpha_z$, class, and by virtue of the N-terminal portion of $G\alpha_{q/z}$, subsequently activates phospholipase C.

Microrhysiometry

CHO cells transiently expressing either NPFF1 alone or NPFF1 accompanied by the chimeric protein Gq/Gz produced robust increases in metabolism when exposed to either NPFF or the related peptide A-18-F-amide as evidenced by increased rates of extracellular acidification when measured by the microphysiometric technique (FIGS. 17A and 17B). Whereas control cells, not expressing NPFF1, produced no increase in acidification rates to either NPFF or A-18-F-amide. In all cases the NPFF1 mediated responses were dose-dependent. CHO cells transfected with NPFF1 alone produced an EC50 value of 19.3 nM for NPFF while cells transfected NPFF1 and the chimeric Gz/Gq produced an EC50 of 27.7 nM for NPFF. Challenges with A-18-F-amide were conducted only on cells that had been transfected with NPFF1 alone. These cells produced an EC50 value of 150 nM for A-18-F-amide. The functional responsiveness to NPFF and A-18-F-amide supports the notion that NPFF1 encodes a receptor for neuropeptide FF (NPFF).

Radioligand Binding Assays

Cos-7 cells transiently expressing the gene encoding the novel rat NPFF1 receptor were used for pharmacological evaluation. Membranes harvested from transiently transfected Cos-7 cells exhibited high affinity, saturable [$^{125}$I]D-Tyr-NPFF ([D-Tyr$^1$(NMe)Phe$^3$]NPFF) binding. Nonlinear analysis of [$^{125}$I]D-Tyr-NPFF saturation data yielded an equilibrium dissociation constant ($K_d$) of 0.335±0.045 nM and a binding site density ($B_{max}$) of 180±11 fmol/mg protein. Specific [$^{125}$I]D-Tyr-NPFF binding was about 50% of total binding at a radioligand concentration equal to the $K_d$ value. Mock-transfected host cells did not display specific [$^{125}$I]D-Tyr-NPFF binding.

To further assess the pharmacological identity of the newly isolated NPFF1 receptor gene, detailed binding properties of cloned NPFF1 receptor were determined from nonlinear analysis of competition of high affinity [$^{125}$I]D-Tyr-NPFF binding. The rank order of affinity of compounds to displace specific [$^{125}$I]D-Tyr-NPFF binding is shown in Table 1.

The binding profile of rat NPFF1 was compared to that of rat spinal cord membranes. Interestingly some differences were observed in the pharmacological profile between the two preparations. (See * Table 2). Notably, fPP did not displace the binding on the NPFF1 receptor up to 1 uM whereas it displayed a high affinity at the rat spinal cord. Furthermore, several compounds displayed significantly different affinities between NPFF1 receptor and the spinal cord membranes. These compounds are highlighted in Table 1 and are ([$^{125}$I]D-Tyr-NPFF, A18Famide, Y8Famide, [Y$^9$] A18Famide, Dynorphin A 1–13, Neuropeptide F and Met-Enk-NH2. These data indicate the presence of additional NPFF receptor subtypes on the rat spinal cord.

Additional pharmacological evaluation was done using 293 human embryonic kidney cells (HEK$^-$ 293 cells) transiently expressing the genes encoding the human NPFF1, NPFF2, and rat NPFF1 receptors, as well as Cos-7 cells expressing the rat NPFF2 receptors. Nonlinear analysis of [$^{125}$I]D-Tyr-NPFF saturation binding data yielded equilibrium dissociation constants (Kd) of 0.46±0.10 and 0.17±0.04 nM for the human NPFF1 and NPFF2, and of 0.65±0.22 and 0.17±0.02 nM for the rat NPFF1 and NPFF2 receptors, respectively. The binding affinities (pKi) of various NPFF-related peptides were derived from competition binding assay using [$^{125}$I]D-Tyr-NPFF as a ligand. In agreement with the data shown in Table 1, fPP showed 31-and 77-fold greater affinity for the rat and human NPFF2 receptors, respectively, when compared to the NPFF1 receptors (see Table 3). The other peptides studied showed overall similar binding affinities for both the rat and human NPFF1 and NPFF2 receptors. NPFF receptors displayed high affinity for FMRF amide and lower binding affinity for the D-Met analog, suggesting the existence of stereoselectivity for this peptide.

The ability of NPFF1 receptors to functionally couple to PI was tested using intact Cos-7 cells transiently expressing NPFF1. Full dose-response curves were determined for NPFF-mediated total IP release (FIG. 18A). NPFF stimulated total IP release with an EC50 of 23 nM and an Emax of approximately 200% basal. This weak stimulation was most probably mediated by NPFF1 coupling to a Gi/Go G-protein via βγ-induced PI turnover, since the response was abolished by pretreatment with pertussis toxin but not cholera toxin. In contrast, a robust stimulation of total IP release was observed following NPFF in Cos-7 cells transfected with both the NPFF1 receptor and the Gq/Gz chimera (FIG. 18B). NPFF stimulated total IP release with an EC50 of 2.95 nM, and an Emax of approximately 1500% basal. As anticipated, neither PTX nor CTX attenuated this response. Similar to what was observed in oocytes, this suggests a coupling in Cos-7 cells to G-proteins of the Gαi/Gαo/Gαz class.

The coupling of human NPFF1 and NPFF2 receptors to the activation of intracellular second messenger pathways was studied further in COS-7 cells co-transfected with the Gq/Gz chimera. In such cells, NPFF elicited an increase in intracellular calcium when either the human NPFF1 or NPFF2 were transfected, and no response was observed in cells that were only transfected with the Gq/Gz chimera. As shown in Table 4, PQRF amide was a full agonist in cells expressing either the NPFF1 or NPFF2 receptors. However, only cells expressing the human NPFF2 responded with an intracellular calcium response to fPP, no response was observed in cells expressing the human NPFF1 receptor, suggesting that fPP is an NPFF2-selective agonist.

TABLE 1 pKi for cloned rat NPFF1 receptor binding in COS-7 cells

| COMPOUND | MEAN | SEM | n |
|---|---|---|---|
| NPFF (F-8-Fa) | 8.535 | 0.02 | 2 |
| (D-Tyr$^1$ - (NMe) Phe$^3$) NPFF | 8.549 | 0.13 | 4 |
| A18Fa | 7.495 | 0.11 | 2 |
| PQRFa | 8.182 | 0.03 | 2 |
| FMRFa | 8.481 | 0.05 | 2 |
| YFa | 8.382 | 0.22 | 2 |
| [Y$^9$] A18Fa | 7.558 | 0.12 | 2 |
| hPP | 5 | 0 | 2 |
| fPP | 5.5 | 0.35 | 2 |
| substance P | 5 | 0 | 2 |
| Dynorphin A1-13 | 6.838 | 0.29 | 2 |
| (3D) Y8Fa | 8.623 | 0.44 | 4 |
| (2D) Y8Fa | 8.33 | 0.15 | 4 |
| CCK8 | 5 | 0 | 2 |
| galanin | 5 | 0 | 2 |
| dopamine | 5 | 0 | 2 |
| naloxone | 5 | 0 | 2 |
| CGRP | 5 | 0 | 2 |
| AF-1 | 6.634 | 0.13 | 2 |
| AF-2 | 7.023 | 0.41 | 2 |
| SchistFLRF | 5.96 | 0.68 | 2 |
| Met5-Arg6-Phe7-Enk-NH2 | 7.35 | 0.22 | 4 |
| Met5-Arg6-Phe7-Enk-OH | 5 | 0 | 2 |
| Neuropeptide F | 6.11 | 0.06 | 4 |
| desamino-nor-Y8Ra | 7.27 | 0.1 | 3 |
| (2DME) Y8Fa | 9.2 | 0.01 | 3 |
| L-arginine | 5 | 0 | 1 |
| D-arginine | 5 | 0 | 1 |
| desipramine | 5 | 0 | 1 |
| fenfluramine | 5 | 0 | 1 |
| harmine | 5 | 0 | 1 |
| levocabastine | 5 | 0 | 1 |
| ibogaine | 5 | 0 | 1 |
| ritanserine | 5 | 0 | 1 |
| a-MSH | 5 | 0 | 1 |
| Tyr-MIF-1 | 5 | 0 | 1 |
| nociceptin | 5 | 0 | 1 |
| nocistatin | 5 | 0 | 1 |
| PMRFa | 8.55 | 0.06 | 2 |
| FTRF | 7.87 | 0.1 | 2 |
| FFRF | 8 | 0 | 2 |

TABLE 2 pKi for rat spinal cord membrane receptor binding

| COMPOUND | MEAN | SEM | n |
|---|---|---|---|
| NPFF (F-8-fa) | 9.055 | 0.08 | 2 |
| (D-Tyr$^1$ - (NMe) Phe$^3$) NPFF | *9.724 | 0.25 | 4 |
| A18Fa | *9.000 | 0.21 | 2 |

TABLE 2-continued pKi for rat spinal cord membrane receptor binding

| COMPOUND | MEAN | SEM | n |
|---|---|---|---|
| PQRFa | 8.541 | 0.07 | 2 |
| FMRFa | 8.493 | 0.23 | 2 |
| Y8Fa | *9.189 | 0.06 | 2 |
| [Y$^9$] A18Fa | *8.502 | 0.01 | 2 |
| hPP | 5 | 0 | 3 |
| fPP | *9.118 | 0.06 | 3 |
| substance P | 5 | 0 | 1 |
| Dynorphin A1-13 | *5.700 | 0.5 | 2 |
| (3D) Y8Fa | 9.123 | 0.12 | 4 |
| (2D) Y8Fa | *9.212 | 0.23 | 4 |
| CCK8 | 5 | 0 | 2 |
| galanin | 5 | 0 | 2 |
| dopamine | 5 | 0 | 2 |
| naloxone | 5 | 0 | 2 |
| CGRP | 5 | 0 | 2 |
| AF-1 | *7.563 | 0.47 | 2 |
| AF-2 | *7.965 | 0.24 | 2 |
| SchistFLRF | 6.39 | 0.23 | 2 |
| Met-Enk-NH2 | *8.400 | 0.08 | 4 |
| Met-Enk-OH | 5 | 0 | 2 |
| Neuropeptide F | *8.100 | 0.1 | 3 |
| desamino-nor-Y8Ra | 7.51 | 0.07 | 3 |
| (2DME) Y8Fa | 9.57 | 0.3 | 4 |
| L-arginine | 5 | 0 | 1 |
| D-arginine | 5 | 0 | 1 |
| desipramine | 5 | 0 | 1 |
| fenfluramine | 5 | 0 | 1 |
| harmine | 5 | 0 | 1 |
| levocabastine | 5 | 0 | 1 |
| ibogaine | 5 | 0 | 1 |
| ritanserine | 5 | 0 | 1 |
| α-MSH | 5 | 0 | 1 |
| Tyr-MIF-1 | 5 | 0 | 1 |
| nociceptin | 5 | 0 | 1 |
| nocistatin | 5 | 0 | 1 |
| PMRFa | 9.37 | 0.11 | 2 |
| FTRF | 8.16 | 0.16 | 2 |
| FFERF | 8.98 | 0.001 | 2 |

AF-1 = FMRF-like peptide
$H_2N$-Lys-Asn-Gln-Phe-Ile-Arg-Phe-$NH_2$
AF-2 H-Lys-His-Gln-Tyr-Leu-Arg-Phe-$NH_2$
Schisto (FLRFNH$_2$) = Pro-Asp-Val-Asp-His-Val-Phe-Leu-Arg-Phe-amide
Met$^5$, Arg$^6$, Phe$^7$-NH$_2$ = enhephalinamide
Met$^5$, Arg$^6$, Phe$^7$-OH = enhephalin

TABLE 3 pKi of NPFF-related peptides at cloned human and rat NPFF receptors in 293 human embryonic kidney cells (HEK-293 cells)

| | human | | rat | |
|---|---|---|---|---|
| | NPFF1 | NPFF2 | NPFF1 | NPFF2 |
| | | pKi ± SEM | | |
| (D-Tyr$^1$ - (NMe) Phe$^3$) NPFF | 8.1 ± 0.06 | 8.5 ± 0.08 | 8.8 ± 0.005 | 8.7 ± 0.16 |
| fPP | 5.9 ± 0.09 | 7.4 ± 0.13 | 5.4 ± 0.10 | 7.3 ± 0.02 |
| FMRF amide | 9.1 ± 0.19 | 8.4 ± 0.02 | 8.7 ± 0.01 | 8.0 ± 0.02 |
| D-Met-FMRF amide | 6.6 ± 0.24 | 6.4 ± 0.03 | 6.2 ± 0.09 | 6.2 ± 0.03 |
| A18Fa | 7.2 ± 0.11 | 8.9 ± 0.13 | 7.5 ± 0.14 | 8.2 ± 0.007 |
| PQRFa | 7.4 ± 0.45 | 7.6 ± 0.05 | 7.6 ± 0.05 | 7.6 ± 0.004 |
| BIBP 3226 | 6.9 ± 0.04 | 5.9 ± 0.04 | 7.6 ± 0.04 | 5.8 ± 0.02 |

TABLE 4

Activation of intracellular calcium mobilization by COS-7 cells expressing human NPFF receptors and Gq/Gz chimera.

| | NPFF1 | | NPFF2 | |
|---|---|---|---|---|
| Compound | pEC50 | % of NPPF Response | pEC50 | % of NPPF Response |
| NPFF | 7.8 ± 0.10 | 100 | 8.7 ± 0.02 | 100 |
| fPP | <5.0 | 0 | 6.7 ± 0.07 | 78 |
| PQRF amide | 6.7 ± 0.02 | 93 | 7.0 ± 0.04 | 94 |

Localization

Figure 19:
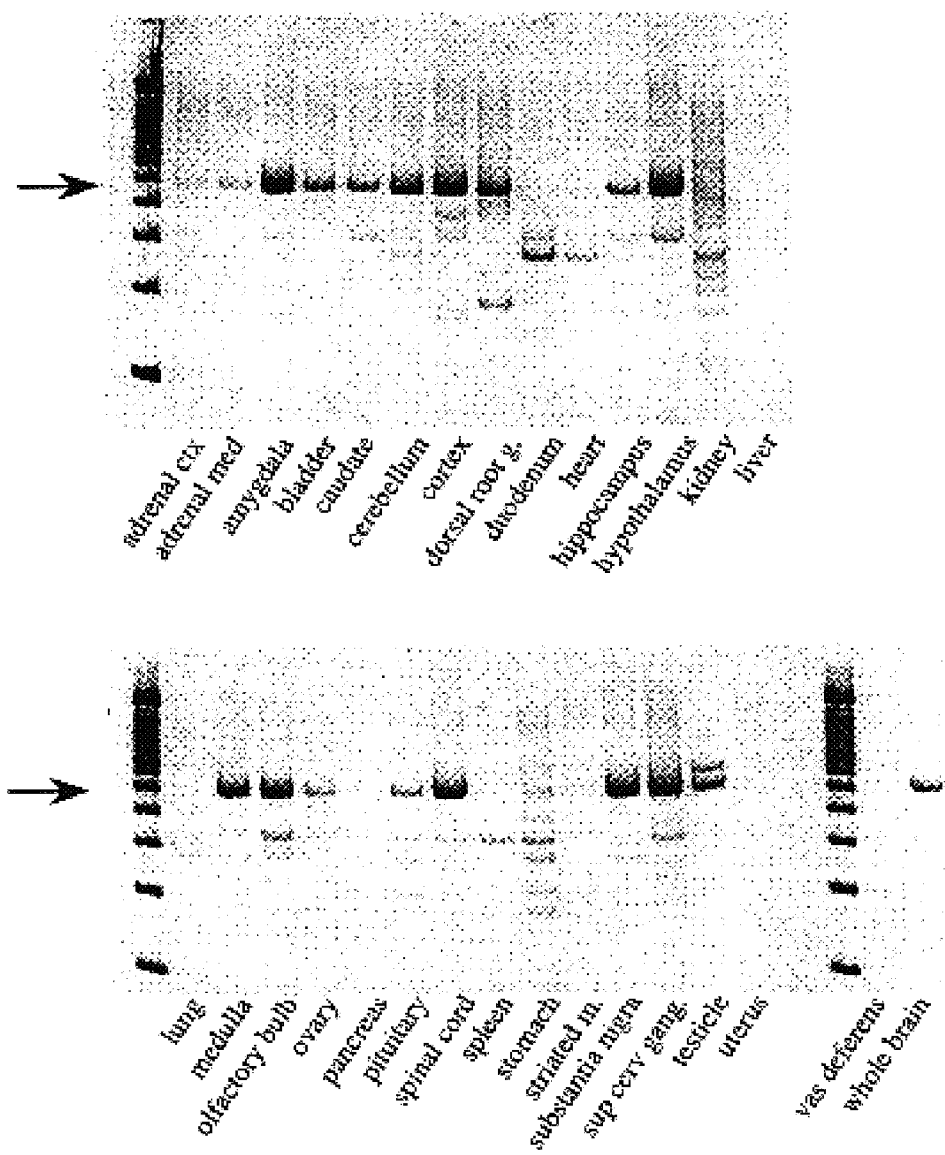
Figure 20:
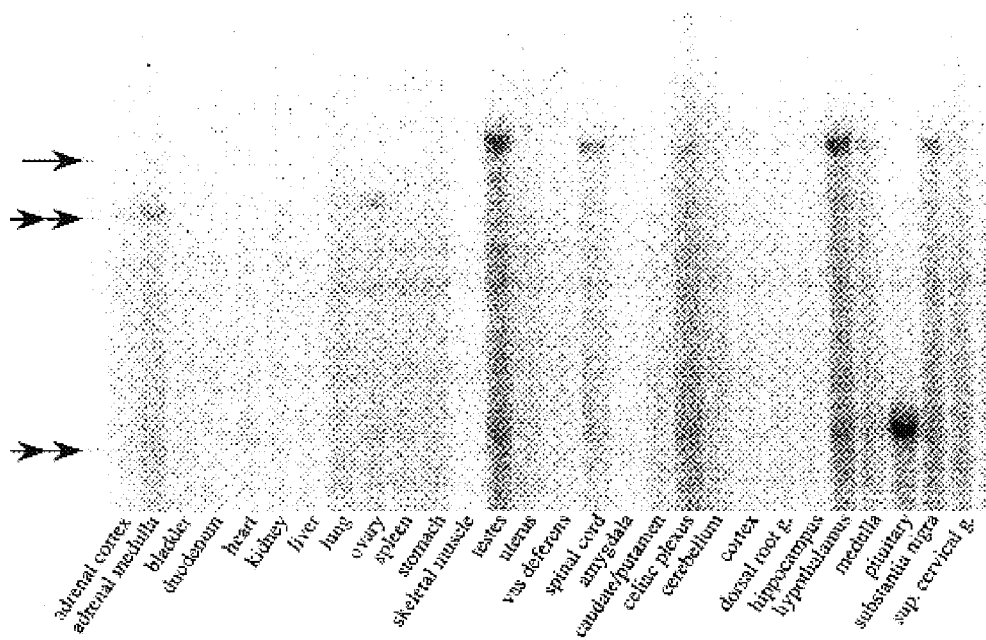

Detection of mRNA coding for rat NPFF1 receptors: mRNA was isolated from multiple tissues (Table 3) and assayed as described. The distribution of mRNA encoding rat NPFF1 receptors is widespread throughout the central nervous system, and structures associated with the nervous system (Table 3, FIGS. 19, 20). The highest levels of rNPFF1 mRNA are found in the hypothalamus and the pituitary gland. The protected segment seen with mRNA isolated from the pituitary, adrenal gland and ovary is considerably shorter than that seen in other tissue (FIG. 20) and indicates the possibility of splice variants of this receptor. Peripheral organs contain little or no mRNA encoding rNPFF1 with the exception of the testes, ovary, the adrenal medulla and the adrenal cortex. There is good correlation between the distribution determined by RT-PCR and RPA (Table 3, FIGS. 19, 20). RT-PCR detected rat NPFF1 in more areas than RPA as it is a more sensitive technique.

High levels of mRNA encoding NPFF receptors in the hypothalamus and pituitary, with relatively low expression in most of the other regions assayed implicates this receptor in neuroendocrine control, as well as the control of feeding and metabolic regulation. Its presence in other areas, including the spinal cord, medulla and dorsal root ganglia implicate NPFF receptors as a potential modulator of pain and/or sensory transmission. Low levels in the hippocampal formation indicate a possible role in learning and memory.

TABLE 5

Summary of distribution of mRNA coding for rat NPFF1 receptors

| Tissue | RT-PCR | Ribonuclease protection assay (RPA) | Potential applications |
|---|---|---|---|
| adrenal cortex | + | + | regulation of steroid hormones |
| adrenal medulla | + | ++ | regulation of epinephrine release |
| urinary bladder | − | | urinary incontinence |
| duodenum | +/− | − | gastrointestinal disorders |
| heart | +/− | − | cardiovascular indications |
| kidney | + | − | electrolyte balance, hypertension |
| liver | +/− | − | diabetes |
| lung | +/− | − | respiratory disorders, asthma |
| ovary | + | + | reproductive function |
| pancreas | +/− | NA | diabetes, endocrine disorders |
| spleen | +/− | − | immune disorders |
| stomach | +/− | − | gastrointestinal disorders |
| striated muscle | +/− | − | musculoskeletal disorders |
| testicle | +/− | + | reproductive function |
| uterus | +/− | − | reproductive function |
| vas deferens | − | − | reproductive function |
| whole brain | +++ | | |
| spinal cord | ++ | ++ | analgesia, sensory modulation and transmission |
| amygdala | +++ | +/− | |
| caudate/putamen | ++ | − | modulation of dopaminergic function |
| cerebellum | +++ | + | motor coordination |
| cerebral cortex | ++ | + | Sensory and motor integration, cognition |
| DRG | + | + | sensory transmission |
| hippocampus | +++ | + | cognition/memory |
| hypothalamus | +++ | +++ | appetite/obesity, neuroendocrine regulation |
| medulla | ++ | ++ | analgesia, motor coordination |
| olfactory bulb | ++ | NA | olfaction |
| pituitary | +++ | +++ | Endocrine/neuro-endocrine regulation |
| substantia nigra | +++ | ++ | Modulation of dopaminergic function |
| superior cervical ganglion | + | − | modulation of sympathetic innervation |

NA = not assayed

Localization of mRNA Coding for hNPFF2 Receptors Using RT-PCR

Figure 21:
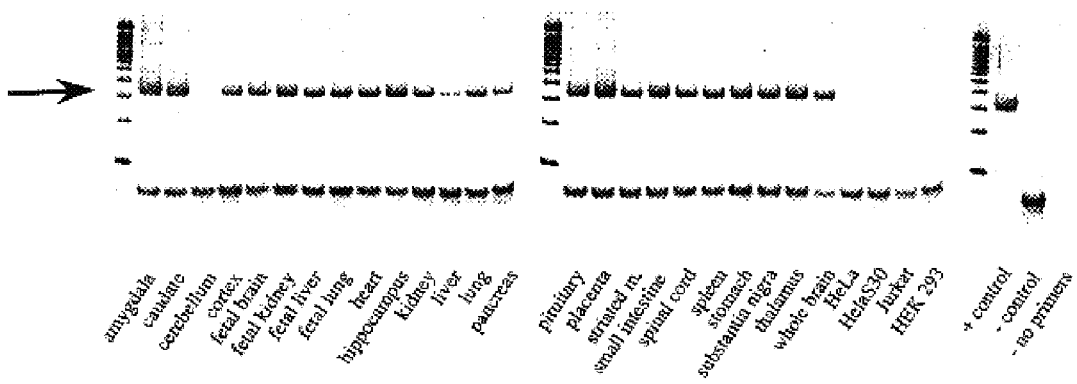

Detection of mRNA Coding for hNPFF2 Receptors mRNA was isolated from multiple tissues (Table 4) and assayed as described. The distribution of mRNA encoding hNPFF2 receptors is widespread throughout all regions assayed. (Table 4, FIG. 21).

TABLE 6

Distribution of mRNA coding for hNPFF2 receptors

| Region | hNPFF2 | Potential Implications |
|---|---|---|
| liver | ++ | Diabetes |
| kidney | ++ | Hypertension, electrolyte balance |
| Lung | ++ | Respiratory disorders, asthma |
| heart | ++ | Cardiovascular indications |
| stomach | ++ | Gastrointestinal disorders |
| small intestine | ++ | Gastrointestinal disorders |

TABLE 6-continued

Distribution of mRNA coding for hNPFF2 receptors

| Region | hNPFF2 | Potential Implications |
| --- | --- | --- |
| spleen | ++ | Immune function |
| pancreas | ++ | Diabetes, endocrine disorders |
| striated muscle | ++ | Musculoskeletal disorders |
| pituitary | ++ | Endocrine/neuroendocrine regulation |
| whole brain | ++ | |
| amygdala | ++ | Depression, anxiety, mood disorders |
| hippocampus | ++ | Cognition/memory |
| spinal cord | ++ | Analgesia, sensory modulation and transmission |
| cerebellum | ++ | Motor coordination |
| thalamus | ++ | sensory integration |
| substantia nigra | ++ | Modulation of dopaminergic function and motor coordination |
| caudate | ++ | Modulation of dopaminergic function |
| fetal brain | ++ | Developmental disorders |
| fetal lung | ++ | Developmental disorders |
| fetal kidney | ++ | Developmental disorders |
| fetal liver | ++ | Developmental disorders |
| HEK-293 cells | + | |
| HeLa cells | − | |
| Jurkat cells | − | |

Localization of mRNA Coding for Human and Rat NPFF

Results mRNA was isolated from multiple tissues (listed in Table 7) and assayed as described.

Human NPFF1

Quantitative RT-PCR using a fluorgenic probe demonstrated mRNA encoding human NPFF1 RNA to be localized in highest abundance in CNS tissue. All CNS tissues assayed demonstrate moderate levels of NPFF1 RNA. The broad distribution of NPFF1 mRNA implies a modulatory role in multiple systems within the CNS. Highest levels are found in the spinal cord, hippocampus, amygdala, thalamus and hypothalamus. High levels in the spinal cord and thalamus imply an important role in sensory transmission or modulation (including nociception). The hippocampal formation and amygdala also contain high levels of NPFF1 mRNA. Localization to these structures support the hypothesis that NPFF is involved in the modulation of learning and memory as well as having a role in the regulation of fear, mood, and may provide a target for the treatment of depression, anxiety, phobias and mood disorders.

NPFF1 mRNA is also expressed in the hypothalamus in moderate amounts. This suggests a role in neuroendocrine regulation, regulation of circadian rhythms, regulation of appetite/feeding behavior and other functions that are modulated by the hypothalamus.

NPFF1 mRNA is also expressed, although at somewhat lower levels, in the basal ganglia. The caudate-putamen, and substantia nigra both express moderate levels of NPFF1 mRNA. Localization to these regions implies a role in regulation of dopaminergic systems, and may provide a therapeutic target for treatment of movement disorders such as Parkinsons disease or tardive dyskinesia. The cerebellum also contains substantial amounts of NPFF1 mRNA indicating a role in the control of movement.

Fetal brain, although expressing NPFF1 mRNA, does so in much lower levels than that found in the adult. There is a five-fold difference in mRNA levels between fetal and adult brain. It is not known at this time if the developmental regulation is global within the CNS or restricted to selected regions. The time course of this increase has not been examined and would be important in understanding the function of this receptor.

In peripheral tissue, all tissues assayed expressed measurable NPFF1 mRNA levels. However, levels in peripheral tissue are much lower than those found in the CNS. The peripheral tissues expressing the highest levels of NPFF1 mRNA are spleen, lung and fetal lung. Levels in these tissues are more than 10 fold lower than that detected in the highest CNS regions. Others tissues assayed contain low levels of NPFF1 mRNA as indicated in Table 7.

In summary, the distribution of human NPFF1 mRNA implies broad regulatory function in the CNS, most notably in sensory transmission, modulation of the limbic system, modulation of feeding/circadian rhythms, and modulation of extrapyramidal motor systems. Its presence, albeit at low levels in peripheral tissues implies of broad regulatory role in multiple organ systems.

Human NPFF2

Unlike the distribution of human NPFF1 mRNA, which is expressed primarily in the CNS, the highest levels of NPFF2 RNA are found in the placenta. Expression in the placenta is four-fold higher than any other tissue assayed (Table 7). Presence of high levels NPFF2 receptor mRNA in the placenta indicates a role in gestational regulation and possible gestational abnormalities. It is not known at this time, whether NPFF2 mRNA is present at all stages of development, or which cells in the placenta express these receptors. Other tissues expressing NPFF2 mRNA include the small intestine, pituitary and spleen. RNA levels in the placenta are 20 fold higher than in these organs.

Within the CNS, highest levels of NPFF2 mRNA expression are found in the amygdala, caudate-putamen, and the hippocampal formation. These regions also express high levels of NPFF1 mRNA. As with NPFF1, localization to limbic structures supports the hypothesis that NPFF is involved in the modulation of learning and memory as well as having a role in the regulation of fear, mood, and may provide a target for the treatment of depression, anxiety, phobias and mood disorders. Localization to the caudate/putamen implies regulation of dopaminergic systems and a role in the regulation of extrapyramidal motor systems. Other areas assayed are listed in Table 7.

In summary, human NPFF2 mRNA is broadly distributed in both CNS and peripheral tissue. This implies broad regulatory functions in multiple organ systems. High levels in the placenta indicate a significant role in gestational physiology. Within the CNS, its implied function is modulation of the limbic system and extrapyramidal motor systems. Its presence, albeit at low levels in multiple tissues implies a broad modulatory role involving multiple physiological modalities.

Rat NPFF1

As with the human NPFF1 receptor mRNA, highest levels of rat NPFF1 RNA are found in central nervous system structures. Highest levels are found in the hypothalamus, amygdala, and the substanta nigra. All CNS structures assayed express rNPFF1 RNA (Table 8).

The high levels of NPFF1 mRNA expressed in the hypothalamus indicate a role in neuroendocrine regulation, regulation of circadian rhythms, regulation of appetite and other functions that are modulated by the hypothalamus. High levels in the amygdala and other limbic (or limbic related) structures suggest a role in modulation of mood, fear, phobia, anxiety and may provide a therapeutic target for the treatment of depression and other neuropsychiatric disorders.

The presence of lower levels of NPFF1 RNA in other areas such as the hippocampal formation, spinal cord, medulla, caudate-putamen, cerebral cortex, cerebellum and other areas suggests diverse functions as suggested in Table 8.

The tissue showing the highest levels of NPFF1 mRNA outside the CNS is the testes. Levels in the testes are more than approximately half of the levels found in the hypothalamus, and containing approximately the same levels as those found in the amygdala, substantia nigra, and olfactory bulb (see Table 8). This strongly suggests a role in endocrine regulation or reproductive function. Other peripheral tissues showing moderate amounts of NPFF1 mRNA are listed in Table 8.

Rat NPFF2

As with rat NPFF1, high levels of rat NPFF2 mRNA are found in CNS structures. Highest levels are found in the spinal cord and medulla. Localization to these structures as well as moderate levels in the dorsal root and trigeminal ganglia, strongly suggest a role in sensory transmission (or modulation) including nociceptive stimuli. In addition to the above, there are also moderate levels of NPFF2 RNA localized to the retina. This suggests a role in modulation of visual stimuli or circadian rhythms.

Other CNS regions expressing high levels of NPFF2 RNA include the hypothalamus, substantia nigra and amygdala. The high levels of NPFF2 mRNA expressed in the hypothalamus indicate a role in neuroendocrine regulation, regulation of circadian rhythms, regulation of appetite and other functions that are modulated by the hypothalamus. High levels in the amygdala suggests a role in modulation of mood, fear, phobia, anxiety and may provide a therapeutic target for the treatment of depression and other neuropsychiatric disorders.

The tissue expressing the highest levels of NPFF2 mRNA outside the CNS is the heart. NPFF2 RNA levels in the heart are comparable to those found in many CNS structures. The heart expresses similar levels of NPFF2 RNA as the spinal cord, medulla, hypothalamus, or substantia nigra. Another tissue expressing moderate levels of NPFF2 mRNA is the aorta. This distribution strongly implies regulation of cardiovascular function, perhaps by innervation from brain stem autonomic centers. It is not known if the NPFF2 mRNA is localized to myocytes within the heart or if they are localized on the conductance fibers, smooth muscle, or endothelial cells.

Lower levels of NPFF2 mRNA are localized in multiple tissues though the body as listed in Table 8. The localization of NPFF2 mRNA to every tissue assayed indicated that this receptor may have broad regulatory roles in multiple systems.

In summary: The distribution of rat NPFF1 implies a role in limbic function as described, and the distribution of NPFF2 implies a role in sensory transmission or modulation. The broad distribution of both of these receptors in the central nervous system as well as in peripheral organs, implies a broad regulatory role in multiple physiological systems.

TABLE 7

Distribution of mRNA coding for human NPFF receptors using qRT-PCR (mRNA encoding NPFF is expressed as % of highest expressing tissue: spinal cord for NPFF 1 and placenta for NPFF2 + SEM)

| Region | h-NPFF1 | h-NPFF2 | Potential applications |
|---|---|---|---|
| heart | 0.21 + 0.03 | 0.39 + 0.21 | Cardiovascular indications |
| kidney | 0.67 + 0.11 | 0.83 + 0.13 | Hypertension, electrolyte balance |
| liver | 0.35 + 0.07 | 0.21 + 0.04 | Diabetes |
| lung | 6.96 + 0.56 | 0.71 + 0.09 | Respiratory disorders, asthma |
| pancreas | 0.23 + 0.06 | 0.53 + 0.09 | Diabetes, endocrine disorders |
| pituitary | 2.46 + 0.32 | 4.65 + 0.47 | Endocrine/ neuroendocrine regulation |
| placenta | 0.23 + 0.03 | 100 + 13.20 | Gestational abnormalities |
| small intestine | 2.74 + 0.10 | 4.39 + 0.17 | Gastrointestinal disorders |
| spleen | 8.08 + 0.55 | 3.81 + 0.28 | Immune disorders |
| stomach | 0.55 + 0.06 | .095 + 0.14 | Gastrointestinal disorders |
| striated muscle | 1.22 + 0.16 | 0.78 + 0.12 | Musculoskeletal disorders |
| amygdala | 43.52 + 4.35 | 27.24 + 1.78 | Depression, phobias, anxiety, mood disorders |
| caudate-putamen | 19.04 + 0.75 | 9.30 + 1.12 | Modulation of dopaminergic function |
| cerebellum | 20.48 + 2.14 | trace | Motor coordination |
| hippocampus | 44.56 + 5.55 | 7.39 + 0.75 | Cognition/memory |
| hypothalamus | 20.65 + 0.97 | 1.58 + 0.02 | appetite/obesity, neuroendocrine regulation |
| spinal cord | 100 + 4.97 | 1.32 + 0.07 | Analgesia, sensory modulation and transmission |
| substantia nigra | 13.36 + 0.81 | 0.57 + 0.06 | Modulation of dopaminergic function. Modulation of motor coordination. |
| thalamus | 29.84 + 3.75 | 2.24 + 0.27 | sensory integration disorders |
| whole brain | 21.28 + 1.00 | 7.89 + 1.12 | |
| fetal brain | 4.24 + 0.33 | 0.69 + 0.08 | Developmental disorders |
| fetal lung | 6.01 + 0.89 | 0.37 + 0.08 | Developmental disorders |
| fetal kidney | 1.89 0.23 | 2.86 + 0.31 | Developmental disorders |
| fetal liver | trace | 0.54 + 0.06 | Developmental disorders |

TABLE 8

Summary of distribution of mRNA coding for rat NPFF receptors (mRNA encoding NPFF is expressed as % of highest expressing tissue: hypothalamus for NPFF 1 and placenta for NPFF2 + SEM)

| Tissue | rNPFF1 | rNPFF2 | Potential applications |
|---|---|---|---|
| adipose | 2.56 + 0.24 | 11.72 + 3.17 | metabolic disorders |
| adrenal cortex | 2.98 + 0.35 | 4.70 + 0.44 | regulation of steroid hormones |
| adrenal | 16.84 + 1.23 | trace | regulation of |

TABLE 8-continued

Summary of distribution of mRNA coding for rat NPFF receptors
(mRNA encoding NPFF is expressed as % of highest expressing tissue:
hypothalamus for NPFF 1 and placenta for NPFF2 + SEM)

| Tissue | rNPFF1 | rNPFF2 | Potential applications |
|---|---|---|---|
| medulla | | | epinephrine release |
| amygdala | 57.09 + 10.25 | 41.65 + 5.31 | depression, phobias, anxiety, mood disorders |
| aorta | 1.23 + 0.24 | 23.83 + 3.70 | cardiovascular indications |
| celiac plexus | 3.60 + 0.14 | 12.15 + 1.25 | modulation of autonomic function |
| cerebellum | 17.33 + 1.69 | 10.41 + 1.51 | motor coordination |
| cerebral cortex | 21.72 + 0.78 | 10.99 + 2.29 | Sensory and motor integration, cognition |
| choroid plexus | 24.82 + 1.10 | 29.54 + 6.92 | regulation of cerebrospinal fluid |
| colon | trace | 8.38 + 2.72 | gastrointestinal disorders |
| dorsal root ganglia | 2.77 + 0.46 | 38.26 + 3.47 | sensory transmission |
| duodenum | trace | 5.28 + 0.37 | gastrointestinal disorders |
| heart | 3.19 + 0.30 | 82.32 + 7.97 | cardiovascular indications |
| hippocampus | 20.27 + 1.63 | 8.28 + 2.41 | cognition/memory |
| hypo-thalamus | 100 + 6.15 | 84.26 + 11.01 | appetite/obesity, neuroendocrine regulation |
| kidney | 1.03 + 0.23 | 20.44 + 1.36 | electrolyte balance, hypertension |
| liver | 1.82 + 0.31 | 3.20 + 0.42 | diabetes |
| lung | 3.72 + 0.29 | 15.88 + 4.35 | respiratory disorders, asthma |
| medulla | 22.44 + 2.21 | 92.01 + 6.49 | analgesia, motor coordination |
| nucleus accumbens | 34.75 + 0.78 | 10.85 + 1.60 | regulation of dopaminergic function, drug addiction, neuropsychiatric disorders |
| olfactory bulb | 40.96 + 4.01 | 9.83 + 4.53 | olfaction |
| ovary | 13.74 + 1.85 | 12.35 + 2.59 | reproductive function |
| pancreas | trace | trace | diabetes, endocrine disorders |
| pineal | trace | 4.12 + 0.95 | regulation of melatonin release |
| pituitary | 23.58 + 1.81 | 33.90 + 1.94 | endocrine/neuroendocrine regulation |
| retina | 14.15 + 0.97 | 40.19 + 2.48 | visual disorders |
| salivary gland | trace | 32.93 + 7.48 | |
| spinal cord | 24.00 + 1.41 | 100 + 5.91 | analgesia, sensory modulation and transmission |
| spleen | trace | trace | immune disorders |
| stomach | trace | 13.90 + 0.69 | gastrointestinal disorders |
| striated muscle | trace | trace | musculoskeletal disorders |
| striatum | 17.33 + 1.69 | 16.37 + 4.59 | modulation of dopaminergic function, motor disorders |
| substantia nigra | 48.82 + 5.54 | 66.83 + 8.45 | modulation of dopaminergic function, modulation of motor coordination |
| testes | 42.61 + 4.71 | 4.31 + 0.68 | reproductive function |
| thalamus | 3.14 + 0.25 | 14.92 + 1.92 | sensory integration disorders |
| thymus | trace | 11.53 + 2.92 | immune disorders |
| trigeminal ganglia | 16.09 + 0.14 | 56.82 + 2.33 | sensory transmission |
| urinary bladder | trace | 15.79 + 1.39 | urinary incontinence |
| uterus | trace | trace | reproductive disorders |
| vas deferens | trace | trace | reproductive function |
| whole brain | 21.49 + 1.88 | 23.83 + 2.97 | |

Localization of NPFF Receptor Subtypes in the Rat CNS

Telencephalon

The cerebral cortex and the amygdala displayed [$^{125}$I] [D-Tyr$^1$-(NMe)Phe$^3$]NPFF binding just above background for both the NPFF1 and NPFF2 receptors.

In the basal ganglia the globus pallidus was devoid of any specific binding. [$^{125}$I] [D-Tyr$^1$-(NMe)Phe$^3$]NPFF binding related to the NPFF2 receptor was discretely located in the dorsolateral caudate-putamen and was completely displaced by frog PP. NPFF1 binding sites were evident above background in the accumbens nucleus. Within the septum there was a rostrocaudal gradient in binding sites related to NPFF1. The greatest density of binding was observed in the more caudal laterodorsal and the intermediate lateral septal nuclei, while rostrally a moderate density was observed. Additionally, moderate NPFF1 binding was detected in the medial septum. See Table 9.

Diencephalon

In the thalamus the majority of [$^{125}$I] [D-Tyr$^1$-(NMe)Phe$^3$]NPFF binding was related to the NPFF2 receptor subtype. NPFF2 receptors were detected in the paraventricular and paratenial nuclei, as well as in the reticular, laterodorsal, anterior pretectal, and parafascicular thalamic nuclei. A significant density of NPFF1 binding sites were detected in the anterodorsal thalamic nucleus with lower expression in the paraventricular, central medial and ventral nuclei. In the epithalamus, NPFF2 receptors were present in the lateral habenula. See Table 9.

In the hypothalamus, a rostrocaudal gradient of [$^{125}$I] [D-Tyr$^1$-(NMe)Phe$^3$]NPFF binding to the NPFF2 receptor was observed in the lateral hypothalamus with the highest density of binding rostrally. The medial mammillary nucleus also contained considerable NPFF2 receptor binding while moderate binding was seen in the lateral anterior hypothalamus. A lower expression of NPFF2 binding sites was observed in the lateroanterior hypothalamus. NPFF1 binding sites were difficult to determine in the hypothalamus due to high background levels and the possible underestimation of NPFF1 binding densities (see Discussion), however, NPFF1 receptor binding sites were detectable in the tuber cinereum. See Table 9.

The hippocampal formation did not exhibit any specific [$^{125}$I][D-Tyr$^1$-(NMe)Phe$^3$]NPFF binding in Ammon's horn, although, a moderate number of NPFF1 binding sites were observed in the ventral dentate gyrus. In other related limbic structures, NPFF1 receptor binding sites were detected in the bed nucleus of the stria terminalis and the pre/parasubiculum appeared to contain both NPFF1 and NPFF2 receptors. See Table 9.

Mesencephalon

[$^{125}$I] [D-Tyr$^1$-(NMe)Phe$^3$]NPFF binding to NPFF2 receptors was identified in the anterior pretectal nucleus and displayed a dorsal to ventral gradient with the highest density dorsally. NPFF2-receptor binding was also observed in the medial pretectal nucleus, posterior intralaminar thalamic nucleus, interstitial nucleus of mlf, substantia nigra, compact part, interpeduncular nucleus, rostral and caudal linear nuclei of raphe, dorsal and median raphe nuclei, retrorubral filed, B9 5-hydroxytryptamine cells, medial and lateral parabrachial nuclei, and the microcellular tegmental nucleus. Moderate [$^{125}$I] [D-Tyr$^1$-(NMe)Phe$^3$]NPFF binding to the NPFF2 receptor was visible in the dorsal and ventral periaqueductal gray and there was a very weak signal in the ventral periaqueductal gray related to the NPFF1 receptor. The superior colliculus, pontine nuclei, and the caudal linear raphe nucleus contained NPFF1 receptor binding sites, while the parabrachial nucleus exhibited NPFF1 binding sites just above background. See Table 9.

Rhombencephalon (Pons/Medulla)

NPFF2 receptor binding sites were evident in the medial vestibular, spinal trigeminal, gigantocelular reticular, Barrington's and ventral cochlear nuclei, in addition to the nucleus of the solitary tract. The highest density of NPFF2 binding sites in the rhombencephalon was seen in the region of the facial nerve in the vicinity of the A5 noradrenaline cells. Throughout the pons and medulla there was a low homogeneous ligand binding just above background which appeared to be related to the NPFF2 receptor. NPFF1 binding sites were detectable in Barrington's nucleus, the nucleus of the solitary tract, principal trigeminal nucleus and throughout the reticular formation. See Table 9.

Spinal Cord

The dorsal horn displayed the greatest number of [$^{125}$I] [D-Tyr-(NMe)Phe$^3$]NPFF binding sites in the spinal cord. Ligand binding in the substantia gelatinosa and lamina X was attributed to the NPFF2 receptor. NPFF1 binding sites were evident in the spinal cord ventral horn. See Table 9.

TABLE 9

Distribution of NPFF1 and NPFF2 receptors in the rat CNS

| Region | rNPFF1 | rNPFF2 | Potential Application |
|---|---|---|---|
| Telencephalon | | | |
| cerebral cortex | + | + | Cognition, sensory and motor integration |
| amygdala | + | + | Emotion and memory, social behaviors, modulation of autonomic and neuroendocrine systems |
| vertical diagonal band | + | − | Memory, modulation of cholinergic transmission |
| horizontal diagonal band | + | − | Memory, modulation of cholinergic transmission |
| globus pallidus | − | − | |
| caudate-putamen | − | + | Sensory/motor integration |
| accumbens n. | + | − | Modulation of dopaminergic function |
| lateral septal n., dorsal | + | + | Modulation of higher cognitive functions, emotions, and autonomic regulation |
| medial septal n. | + | − | Cognitive enhancement via cholinergic system |
| Diencephalon | | | |
| para-ventricular thal. n. | + | + | |
| central medial thalamic n. | + | + | |
| paratenial thalamic n. | − | + | Modulation of information to the medial prefrontal cortex |
| anterodorsal thalamic n. | + | + | Modulation of motor information to the cerebral cortex/Eye movement |
| reticular thalamic n. | − | + | Alertness/sedation |
| laterodorsal thalamic n. | − | + | Emotional expression |
| para-fascicular thal. n. | − | + | Motor and behavioral responses to pain |
| latero-anterior hypothal. | − | + | |
| lateral hypothalamus | − | + | Ingestive behavior, modulation of pain |
| tuber cinereum | + | + | |
| supra-chiasmatic n. | − | + | Circadian rhythm |
| medial mammillary n. | − | + | Integration of autonomic or limbic-related functions with movement |
| lateral habenular n. | − | + | |
| Hippocampal formation | | | |
| Ammon's horn | − | + | |
| ventral dentate gyrus | + | − | Cognition/Memory |
| bed n. stria terminalis | + | + | Central autonomic system |
| pre/para-subiculum | + | + | Modulation of memory aquisition |
| Mesencephalon | | | |
| anterior pretectal n. | − | + | Mediate visual reflexes/nociception |
| medial pretectal n. | − | + | |
| post. intra-laminar n. | − | + | |
| interstitial n. of mlf | − | + | |
| superior colliculus | + | − | Modulation of visual information/spatial localization |
| peri-aqueductal gray | + | + | Analgesia |
| substantia nigra, compact part | − | + | Modulation of DA function/Motor coordination |
| substantia nigra, reticular part | − | − | |
| inter-peduncular n. | + | + | Analgesia |
| rostral linear n. | − | + | |
| caudal linear n. raphe | + | + | |
| red n. | − | − | |
| microcellular tegmental n. | − | + | |
| dorsal raphe n. | − | + | Analgesia |
| median raphe n. | − | + | |
| locus coeruleus | − | − | |
| Barrington's n. | + | + | Pontine micturition center-urinary bladder function |
| A5 noradrenergic cell group | − | + | Control of autonomic functions, modulating the perception of pain; blood pressure |
| Rhomben-cephalon | | | |

TABLE 9-continued

Distribution of NPFF1 and NPFF2 receptors in the rat CNS

| Region | rNPFF1 | rNPFF2 | Potential Application |
|---|---|---|---|
| (Pons/Medulla) | | | |
| medial vestibular n. | − | + | Maintenance of balance and equilibrium, Modulating auditory information |
| n. of solitary tract | + | + | Modulation of gustatory and somatosensory information |
| parabrachial n. | + | + | Modulation of visceral sensory information |
| spinal trigeminal n. | − | + | Nociception |
| cerebellum | − | − | |
| giganto-cellular reticular n. | + | + | Nociception/Analgesia |
| ventral cochlear n. | − | + | Modulation of auditory information |
| Spinal cord | | | |
| dorsal horn | − | + | Nociception/Analgesia |
| ventral horn | + | − | |
| lamina X | − | + | Nociception, sensory-visceral reflex arc |

Discussion

The anatomical distribution of the NPFF1 and NPFF2 receptors in the rat CNS was determined by receptor autoradiography using [$^{125}$I] [D-Tyr$^1$-(NMe)Phe$^3$]NPFF at 0.05 nM and making use of subtype selective displacers to directly visualize the individual receptors, NPFF1 and NPFF2. The radioligand exhibits a somewhat higher affinity for the rat NPFF2 subtype ($K_d$=0.22 nM) relative to the rat NPFF1 subtype ($K_d$=0.65 nM). Thus the data may reflect an approximately threefold underestimate of the NPFF1 receptor density relative to that for the NPFF2 subtype. [$^{125}$I] [D-Tyr$^1$-(NMe)Phe$^3$]NPFF binding to the NPFF1 receptor was defined as the frog PP-insensitive binding, as this compound is highly selective for NPFF2 [$pK_i$=7.3±0.02 at rat NPFF2 and 5.4±0.010 at rat NPFF1 (Table 3). Binding to the NPFF2 receptor was defined as the BIBP 3226-insensitive binding, as BIBP 3226 is highly selective for the NPFF1 receptor [$pK_i$=7.6±0.04 at rat NPFF1 and 5.8±0.02 at rat NPFF2] (Table 3). The results suggest that while both NPFF1 and NPFF2 receptors are present in the rat CNS, the NPFF2 receptor appears to be the predominantly expressed receptor. NPFF1 and NPFF2 receptors are discretely localized inma number of brain nuclei.

NPFF1 receptors were observed to be in cholinergic forebrain regions, namely the nucleus of the diagonal band, the medial and lateral septal nuclei, and the ventral dentate gyrus. NPFF1 binding sites were also detected in the superior colliculus and the spinal cord ventral horn. NPFF2 receptors were found to be present in numerous nuclei in the diencephalon, namely the reticular and laterodorsal thalamic nuclei, the suprachiasmatic, lateroanterior, lateral, and medial mammillary hypothalmic nuclei. Caudally, NPFF2 receptors were found in the compact part of the substantia nigra, periaqueductal gray and various raphe nuclei. In all levels of the spinal cord, the dorsal horn and lamina X contained NPFF2 receptor binding sites.

NPFF-like immunoreactivity (NPFF-LI) has been described in the rat brain (74, 21). The distribution of NPFF-LI in the rat CNS is very limited, the highest levels of immunoreactivity were observed in the hypothalamus and the spinal cord. NPFF-LI neurons were identified in the medial hypothalamus and nucleus of the solitary tract, while immunoreactive fibers were evident in the lateral septal nucleus, amygdala, the lateral hypothalamus, median eminence, bed nucleus of the stria terminalis, nucleus of the diagonal band, nucleus of the solitary tract, the ventral medulla and the trigeminal complex. NPFF-LI cells and terminals, as well as the mRNA for both NPFF1 and NPFF2 (Table 8), have been reported to be present in the substantia gelatinosa and lamina X at all levels of the spinal cord of rats (75, 21). The distribution of the NPFF1 and NPFF2 receptor binding sites correlates well with the distribution of the NPFF-LI neurons and terminals. Additionally, the distribution of the NPFF1 and NPFF2 receptors is concordant with previous reports of the anatomical distribution of NPFF binding sites obtained using [$^{125}$I] [D-Tyr$^1$-(NMe)Phe] NPFF (35) and [$^{125}$I]Y8Fa (76).

Potential Application

NPFF-like peptides have been associated with pain mechanisms, opioid tolerance, autonomic functions, memory and neuroendocrine regulation.

The anatomical distribution of NPFF-LI, NPFF2 mRNA and NPFF2 receptor binding sites supports the idea of a role for the NPFF2 receptor in the regulation of pain and analgesia, perhaps by modulating the effects of the endogenous opioid peptides. NPFF has been shown to attenuate the analgesic effects of morphine after intrathecal and intraventricular injection (77) and the localization suggests that this effect be mediated by the NPFF2 receptor. NPFF-LI in the spinal cord is thought to be mostly of intrinsic origin and NPFF-LI cells in rostral regions of the brain do not send descending fibers to the spinal cord (75). Additionally, no NPFF-LI is found in the dorsal root ganglia, and dorsal rhizotomy does not affect NPFF-LI in the dorsal spinal cord (27, 21). NPFF2 mRNA has been identified in DRGs, and this localization might imply that NPFF2 receptors are located on the primary afferent terminals, possibly mediating neurotransmitter release. NPFF-LI is concentrated in lamina I/II, the projection site for primary afferent terminals, a region that contains the highest density of NPFF2 binding sites. In the substantia gelatinosa primary afferents also make contact with large NPFF-LI nociceptive neurons which in turn project rostrally to the mesencephalon and thalamus, possibly playing a role in the autonomic and affective responses to pain. NPFF2 mRNA has been identified in the spinal cord supporting a role for this receptor in the ascending pain pathway. In lamina X there are NPFF-LI fibers possibly related to descending projections from cells originating around the central canal. Thus, the NPFF2 receptor may also be involved in sensory-visceral reflex arcs.

To further strengthen the concept that the NPFF2 receptor may be involved in nociceptive processing, NPFF2 binding sites were localized in a variety of brain regions known to be involved in nociception and pain modulation, namely the spinal trigeminal nucleus, parabrachial nucleus, gigantocellular reticular nucleus, A5 noradrenergic cell group, dorsal raphe nucleus, periaqueductal gray, lateral hypothalamus, and the parafascicular thalamic nucleus. Injection of an anterograde trace (PHA-L) into the intermediomedial hypothalamus, a site of NPFF-ir cell bodies, supports the concordance between the NPFF2 binding site distribution and NPFF-ir terminals in many of these regions (80). Furthermore, NPFF2 mRNA has been identified in the hypothalamus and medulla. NPFF2 mRNA was also detected in the trigeminal ganglion which is most likely one of the sources of NPFF2 receptors found in the spinal trigeminal nucleus (Table 8).

There is some discordance between the localization of NPFF1 mRNA and NPFF1 binding sites in the spinal cord. While there is no autoradiographic evidence for NPFF1 binding sites in the dorsal horn, NPFF1 mRNA has been identified in the spinal cord and DRG (Table 8). This discrepancy might be explained by the expression of the NPFF1 receptor on the peripheral terminal projections of the DRG cells or on the projections of spinal cord neurons to the ventral horn or more rostrally in the brainstem and thalamus. The localization of NPFF1 mRNA in both spinal cord and DRG and with NPFF1 receptor binding sites in the ventral horn is consistent with a potential role for the NPFF1 receptor in the processing of nociceptive information.

NPFF-LI fibers are present in several limbic system-related structures, namely the hippocampus, lateral septal nucleus, accumbens nucleus, nucleus of the diagonal band, and bed nucleus of the stria terminalis. The NPFF1 receptor is expressed in these regions. Furthermore, NPFF1 mRNA has been detected in the accumbens nucleus, amygdala, and hippocampal formation. On the basis of this localization, a role for the NPFF1 receptor may be to regulate learning and memory and the emotional states of fear and anxiety (78). Kavaliers and Colwell (79) have shown that mice receiving icv injections of IgG from NPFF antiserum acquire spatial tasks more slowly and perform more poorly, while icv NPFF resulted in better acquision of memory. The effect may be associated with the hypothalamo-limbic connections containing NPFF (80).

A role for NPFF receptors in regulating sensory information might be indicated by their presence in the relay nuclei of several sensory pathways. It appears that both of the receptors may participate in the modulation of the visual system. NPFF1 receptor binding sites were observed in the superior colliculus while NPFF2 receptor binding sites were detected in the suprachiasmatic nucleus. Both of these regions receive afferents from the retina that contains mRNA for NPFF1 and NPFF2. The possibility that the NPFF2 receptor might play a modulatory role in circadian rhythms is supported by the localization of NPFF2 binding sites in the suprachiasmatic nucleus. The suprachiasmatic nucleus receives direct input from the retina and is thought to be responsible for the maintenance of circadian rhythms. In the auditory system the NPFF2 receptor appears to be a possible modulator. The NPFF2 receptor is present in the cochlear and medial vestibular nuclei.

The identification of NPFF receptor binding sites and mRNA for NPFF1 and NPFF2 in various components of the basal ganglia, namely, the accumbens nucleus, the substantia nigra, compact part, and the caudate-putamen, suggests that NPFF receptors may be involved in regulation of the dopaminergic system, although they are not found on dopaminergic neurons (81). Ibotenic acid lesion studies have shown that NPFF receptors in the substantia nigra, compact part are on afferent fibers, and thus may indirectly influence the mesocorticolimbic system. NPFF2 receptors were identified in the dorsolateral caudate-putamen, an region which represents the target area for the somatosensory cortex and may be involved in sensorimotor integration.

Some of the highest NPFF-LI in the brain was observed in the hypothalamus, one of the main loci for NPFF-LI cell bodies (74). The lateral hypothalamus is involved in catecholaminergic and serotonergic feeding systems and plays a role in circadian feeding and spontaneous activity. The localization of NPFF2 receptor binding sites and mRNA in this region suggests that the NPFF2 receptor may be involved in the regulation of ingestive behavior. Some of the NPFF2 receptor binding sites in the hypothalamus may be located presynaptically on projections from the amygdala since NPFF2 mRNA has been detected in the amygdala (Table 8). In addition, NPFF1 mRNA was detected in the amygdala and hypothalamus (Table 8), suggesting that NPFF1 receptors may also be involved in the regulation of ingestive behaviors. While NPFF1 binding sites were not evident in the hypothalamus, there was a low density of NPFF1 binding sites seen in the amygdala. The lateral parabrachial and nucleus of the solitary tract are two other brain regions involved in the regulation of feeding that contain NPFF1 and NPFF2 receptor binding sites. The origin of dense immunoreactive terminals in these regions is thought to be from the hypothalamus where NPFF1 and NPFF2 mRNA have been found, further supporting a potential role for both receptors in ingestive behaviors.

Effects of NPFF on Blood Pressure in Normotensive Rats

Results

NPFF (1.0 mg/kg) produced a transient increase in MAP. A similar increase in blood pressure was evoked by fPP (0.1 mg/kg).

To test whether the response to fPP was mediated by an action at NPFF receptors or NPY-$Y_1$ receptors, we first determined a dose of BIBP 3226 (NPY-$Y_1$ antagonist which has relatively high affinity for the rat NPFF1 receptor; see Table 9) which was just sufficient to block the pressor response to pLeu, Pro-NPY. We then tested this same dose of BIBP 3226 against fPP and NPFF. When administered 1 minute before the agonists, the NPY-$Y_1$ receptor antagonist BIBP 3226 (0.3 mg/kg) completely blocked the pressor responses to pLeu, Pro-NPY and fPP, and reduced the response to NPFF by ca 50%.

Discussion

The pharmacological differentiation of NPFF, receptor versus the NPFF2 receptor may be accomplished by evaluating the effects of NPFF (non-selective NPFF1/NPFF2 receptor agonist) and fPP (agonist at NPFF-2; inactive at NPFF1). When using fPP as such a tool, however, it must be borne in mind that it also activates NPY receptors. In these experiments, the pressor effect of fPP was blocked completely by the NPY-$Y_1$ receptor antagonist BIBP 3226, at a dose of BIBP 3226 which was just sufficient to completely block the response to pLeu,Pro-NPY. Since the only receptor which is both (1) activated by fPP and (2) blocked by BIBP 3226 is the NPY-$Y_1$ receptor, we conclude that fPP elevates blood pressure via activation of NPY-$Y_1$ receptors, not NPFF receptors. In addition, the pressor response to NPFF was also diminished by ca 50% by BIBP 3226, reflecting the higher affinity of BIBP 3226 for the NPFF1 receptor relative to the NPFF2 subtype.

Thus, the receptor subtype which mediates the pressor response to intravenously administered NPFF exhibits the following characteristics: (1) insensitive to activation by fPP, and (2) sensitive to blockade by BIBP 3226. This indicates that the pressor response to intravenously administered NPFF is predominately via activation of the NPFF1 subtype.

Effects of NPFF on the Micturition Reflex in Anesthetized Rats

Results

Figure 27:
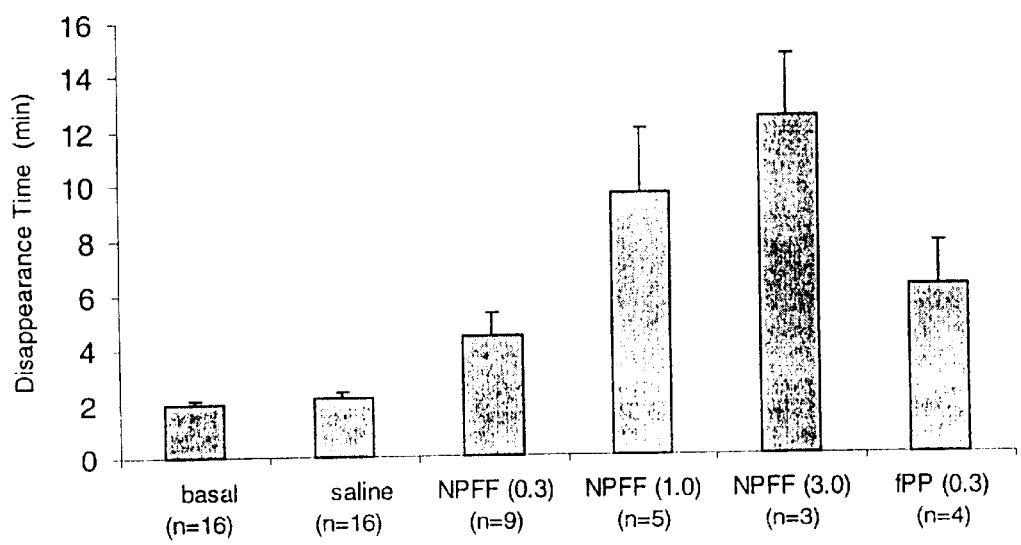
Figure 28:
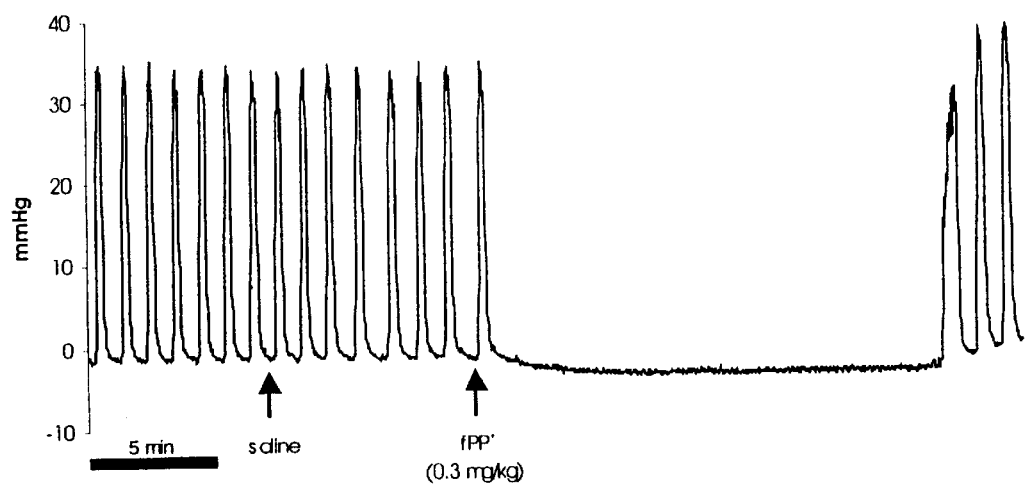

We found, unexpectedly, that distension-induced rhythmic contractions of the rat bladder were inhibited by NPFF (FIG. 26). The disappearance time was dose-dependently increased between 0.3 to 3.0 mg/kg, i.v. (FIG. 27). Contractions were also inhibited by fPP (0.1 mg/kg; FIG. 28). To test whether the response to fPP was via an action at NPFF receptors or NPY-$Y_1$ receptors, fPP was re-tested in the presence of BIBP 3226 (0.3 mg/kg, iv.). In the presence of a concentration of BIBP 3226 sufficient to block fPP's pressor effect (see above), the inhibitory effect of fPP on micturition was not blocked. Furthermore, BIBP 3226 did not block the inhibitory response to NPFF.

Discussion

These results represent the first description of the inhibitory effect of NPFF on the micturition reflex. The effect was dose-dependent, consistent with an interaction between agonist and receptor. Micturition was also inhibited by fPP, which has been shown to be an agonist at the NPFF2 receptor, but devoid of agonist activity at the NPFF1 subtype (see Table 9). The failure of BIBP 3226 to block the effect of fPP on micturition, in contrast to its actions on blood pressure (see above), indicates that fPP inhibits micturition via activation of NPFF receptors and not NPY-$Y_1$ receptors. Therefore, the receptor which mediates inhibition of the of the micturition reflex by intravenously administered NPFF is one which is activated by both NPFF and fPP, indicating that it is the NPFF2 subtype.

The cloning of the gene encoding NPFF receptors has provided the means to explore their physiological roles by pharmacological characterization, and by Northern and in situ mapping of its mRNA distribution. Further, the availability of the DNA encoding the NPFF receptors will facilitate the development of antibodies and antisense technologies useful in defining the functions of the gene products in vivo. Antisense oligonucleotides which target mRNA molecules to selectively block translation of the gene products in vivo have been used successfully to relate the expression of a single gene with its functional sequelae. Thus, the cloning of these receptor genes provides the means to explore their physiological roles in the nervous system and elsewhere, and may thereby help to elucidate structure/function relationships within the GPCR superfamily.

REFERENCES

1. Yang, H. Y., Fratta, W., Majane, E. A., and Costa, E. Isolation, sequencing, synthesis, and pharmacological characterization of two brain neuropeptides that modulate the action of morphine. *Proc.Natl.Acad.Sci.U.S.A.* 82(22):7757–7761, 1985.
2. Vilim, E. S., Ziff, E. Cloning of the neuropeptide NPFF and NPAF precursor form bovine, rat, mouse, and human. Soc. Neurosci. 21:760 (1995).
3. Panula, P., Aarnisalo, A. A., and Wasowicz, K. Neuropeptide FF, a mammalian neuropeptide with multiple functions [published erratum appears in Prog. Neurobiol. 1996 June; 49(3):285]. *Prog. Neurobiol.* 48(4–5):461–487, 1996.
4. Roumy, M. and Zajac, J. M. Neuropeptide FF, pain and analgesia. *Eur. J. Pharmacol.* 345(1):1–11, 1998.
5. Payza, K., Akar, C. A., and Yang, H. Y. Neuropeptide FF receptors: structure-activity relationship and effect of morphine. *J.Pharmacol.Exp.Ther.* 267(1):88–94, 1993.
6. Raffa, R. B., Kim, A., Rice, K. C., de Costa, B. R., Codd, E. E., and Rothman, R. B. Low affinity of FMRFamide and four FaRPs (FMRFamide-related peptides), including the mammalian-derived FaRPs F-8-Famide (NPFF) and A-18-Famide, for opioid mu, delta, kappa 1, kappa 2a, or kappa 2b receptors. *Peptides* 15(3):401–404, 1994.
7. Malin, D. H., Lake, J. R., Arcangeli, K. R., Deshotel, K. D., Hausam, D. D., Witherspoon, W. E., Carter, V. A., Yang, H. Y., Pal, B., and Burgess, K. Subcutaneous injection of an analog of neuropeptide FF precipitates morphine abstinence syndrome. *Life Sci.* 53(17): PL261–6, 1993.
8. Malin, D. H., Lake, J. R., Fowler, D. E., Hammond, M. V., Brown, S. L., Leyva, J. E., Prasco, P. E., and Dougherty, T. M. FMRF-NH2-like mammalian peptide precipitates opiate-withdrawal syndrome in the rat. *Peptides* 11(2):277–280, 1990.
9. Malin, D. H., Lake, J. R., Leyva, J. E., Hammond, M. V., Rogillio, R. B., Arcangeli, K. R., Ludgate, K., Moore, G. M., and Payza, K. Analog of neuropeptide FF attenuates morphine abstinence syndrome. *Peptides* 12(5):1011–1014, 1991.
10. Lake, J. R., Hebert, K. M., Payza, K., Deshotel, K. D., Hausam, D. D., Witherspoon, W. E., Arcangeli, K. A., and Malin, D. H. Analog of neuropeptide FF attenuates morphine tolerance. *Neurosci.Lett.* 146(2):203–206, 1992.
11. Lake, J. R., Hammond, M. V., Shaddox, R. C., Hunsicker, L. M., Yang, H. Y., and Malin, D. H. IgG from neuropeptide FF antiserum reverses morphine tolerance in the rat. *Neurosci. Lett.* 132(1):29–32, 1991.
12. Malin, D. H., Lake, J. R., Smith, D. A., Jones, J. A., Morel, J., Claunch, A. E., Stevens, P. A., Payza, K., Ho, K. K., and Liu, J. Subcutaneous injection of an analog of neuropeptide FF prevents naloxone-precipitated morphine abstinence syndrome. *Drug Alcohol Depend.* 40(1):37–42, 1995.
13. Altier, N. and Stewart, J. Neuropeptide FF in the VTA blocks the analgesic effects of both intra-VTA morphine and exposure to stress. *Brain Res.* 758(1–2):250–254, 1997.
14. Oberling, P., Stinus, L., Le Moal, M., and Simonnet, G. Biphasic effect on nociception and antiopiate activity of the neuropeptide FF (FLFQPQRFamide) in the rat. *Peptides* 14(5):919–924, 1993.
15. Kavaliers, M. Inhibitory influences of mammalian FMR-Famide (Phe-Met-Arg-Phe-amide)-related peptides on nociception and morphine- and stress-induced analgesia in mice. *Neurosci. Lett.* 115(2–3):307–312, 1990.
16. Kavaliers, M. and Yang, H. Y. IgG from antiserum against endogenous mammalian FMRF-NH2-related peptides augments morphine- and stress-induced analgesia in mice. *Peptides* 10(4):741–745, 1989.
17. Kavaliers, M. Innes, D. Sex differences in the effects of neuropeptide FF and IgG from neuropeptide FF on morphine- and stress-induced analgesia. *Peptides* 13(3):603–607, 1992.
18. Gicquel, S., Mazarguil, H., Allard, M., Simonnet, G., and Zajac, J. M. Analogues of F8Famide resistant to degradation, with high affinity and in vivo effects. *Eur. J. Pharmacol.* 222(1):61–67, 1992.
19. Gouarderes, C., Sutak, M., Zajac, J. M., and Jhamandas, K. Antinociceptive effects of intrathecally administered F8Famide and FMRFamide in the rat. *Eur. J. Pharmacol.* 237(1):73–81, 1993.
20. Gouarderes, C., Jhamandas, K., Sutak, M., and Zajac, J. M. Role of opioid receptors in the spinal antinociceptive effects of neuropeptide FF analogues. *Br. J. Pharmacol.* 117(3):493–501, 1996.
21. Lee, C. H., Wasowicz, K., Brown, R., Majane, E. A., Yang, H. T., and Panula, P. Distribution and characterization of neuropeptide FF-like immunoreactivity in the rat nervous system with a monoclonal antibody. *Eur. J. Neurosci.* 5(10):1339–1348, 1993.

22. Kivipelto, L. Ultrastructural localization of neuropeptide FF, a new neuropeptide in the brain and pituitary of rats. *Regul. Pept.* 34(3):211–224, 1991.
23. Kivipelto, L. and Panula, P. Central neuronal pathways containing FLFQPQRFamide-like (morphine-modulating) peptides in the rat brain. *Neuroscience* 41(1): 137–148, 1991.
24. Allard, M., Labrouche, S., Nosjean, A., and Laguzzi, R. Mechanisms underlying the cardiovascular responses to peripheral administration of NPFF in the rat. *J. Pharmacol. Exp. Ther.* 274(1):577–583, 1995.
25. Laguzzi, R., Nosjean, A., Mazarguil, H., and Allard, M. Cardiovascular effects induced by the stimulation of neuropeptide FF receptors in the dorsal vagal complex: An autoradiographic and pharmacological study in the rat. *Brain Res.* 711(1–2):193–202, 1996.
26. Kivipelto, L., Aarnisalo, A., and Panula, P. Neuropeptide FF is colocalized with catecholamine-synthesizing enzymes in neurons of the nucleus of the solitary tract. *Neurosci. Lett.* 143(1–2):190–194, 1992.
27. Panula, P., Kivipelto, L., Nieminen, O., Majane, E. A., and Yang, H. Y. Neuroanatomy of morphine-modulating peptides. *Med.Biol.* 65(2–3):127–135, 1987.
28. Allard, M., Geoffre, S., Legendre, P., Vincent, J. D., and Simonnet, G. Characterization of rat spinal cord receptors to FLFQPQRFamide, a mammalian morphine modulating peptide: a binding study. *Brain Res.* 500(1–2):169–176, 1989.
29. Allard, M., Zajac, J. M., and Simonnet, G. Autoradiographic distribution of receptors to FLFQPQRFamide, a morphine-modulating peptide, in rat central nervous system. *Neuroscience* 49(1):101–116, 1992.
30. Gouarderes, C., Tafani, J. A. M., and Zajac, J. M. Affinity of neuropeptide FF analogs to opioid receptors in the rat spinal cord. *Peptides* 19(4):727–730, 1998.
31. Payza, K. and Yang, H. Y. Modulation of neuropeptide FF receptors by guanine nucleotides and cations in membranes of rat brain and spinal cord. *J.Neurochem.* 60(5):1894–1899, 1993.
32. Devillers, J. P., Mazarguil, H., Allard, M., Dickenson, A. H., Zajac, J. M., and Simonnet, G. Characterization of a potent agonist for NPFF receptors: binding study on rat spinal cord membranes. *Neuropharmacology* 33(5):661–669, 1994.
33. Gicquel, S., Mazarguil, H., Desprat, C., Allard, M., Devillers, J. P., Simonnet, G., and Zajac, J. M. Structure-activity study of neuropeptide FF: contribution of N-terminal regions to affinity and activity. *J.Med.Chem.* 37(21):3477–3481, 1994.
34. Dupouy, V. and Zajac, J. M. Neuropeptide FF receptors in rat brain: A quantitative light-microscopic autoradiographic study using [125I] [D. Tyr1, (NMe)Phe3]NPFF. *Synapse* 24(3):282–296, 1996.
35. Gouarderes, C., Tafani, J. A. M., Mazarguil, H., and Zajac, J. M. Autoradiographic characterization of rat spinal neuropeptide FF receptors by using [125I] [D. Tyr1, (NMe)Phe3]NPFF. *Brain Res. Bull.* 42(3):231–238, 1997.
36. Gherardi, N. and Zajac, J. M. Neuropeptide FF receptors of mouse olfactory bulb: Binding properties and stimulation of adenylate cyclase activity. *Peptides* 18(4):577–583, 1997.
37. Kontinen, V. K., Aarnisalo, A. A., Idaenpaeaen-Heikkilae, J. J., Panula, P., and Kalso, E. Neuropeptide FF in the rat spinal cord during carrageenan inflammation. *Peptides* 18(2):287–292, 1997.
38. Wei, H., Panula, P., and Pertovaara, A. A differential modulation of allodynia, hyperalgesia and nociception by neuropeptide FF in the periaqueductal gray of neuropathic rats: Interactions with morphine and naloxone. *Neuroscience* 86(1):311–319, 1998.
39. Robert, J. J., Orosco, M., Rouch, C., Jacquot, C., and Cohen, Y. Unexpected responses of the obese "cafeteria" rat to the peptide FMRF-amide. *Pharmacol.Biochem.Behav.* 34(2):341–344, 1989.
40. Murase, T., Arima, H., Kondo, K., and Oiso, Y. Neuropeptide FF reduces food intake in rats. *Peptides* 17(2):353–354, 1996.
41. Kavaliers, M., Hirst, M., and Mathers, A. Inhibitory influences of FMRFamide on morphine- and deprivation-induced feeding. *Neuroendocrinology*. 40(6):533–535, 1985.
42. Muthal, A. V., Mandhane, S. N., and Chopde, C. T. Central administration of FMRFamide produces antipsychotic-like effects in rodents. *Neuropeptides* 31(4):319–322, 1997.
43. Malin, D. H., Lake, J. R., Short, P. E., Blossman, J. B., Lawless, B. A., Schopen, C. K., Sailer, E. E., Burgess, K., and Wilson, O. B. Nicotine abstinence syndrome precipitated by an analog of neuropeptide FF. *Pharmacol.Biochem.Behav.* 54(3):581–585, 1996.
44. U.S. Pat. No. 5,602,024 (Gerald et al. Feb. 11, 1997).
45. Coleman, A. (1984) Transcription and Translation: A Practical Approach (B. D. Hanes, S. J. Higgins, eds., pp 271–302, IRL Press, Oxford, 1984)
46. Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A., Davidson, N. (1993) *Proc. Natl. Acad. Sci. USA* 90:10235–10239.
47. Fargin, A.; Raymond, J. R.; Lohse, M. J.; Kobilka, B. K.; Caron, M. G.; Lefkowitz, R. J. *Nature* 335:358–360 (1988).
48. Fong, T. M.; Huang, R. C.; Yu, H.; Swain, C. J.; Underwood, D.; Cascieri, M. A.; Strader, C. D. *Can. J. Physiol. Pharmacol.* 73(7):860–865 (July 1995).
49. Graziano, M. P.; Hey, P. J.; Strader, C. D. *Receptors Channels* 4(1):9–17 (1996).
50. Guam, X. M.; Amend, A.; Strader, C. D.; *Mol. Pharmacol.* 48(3):492–498 (Sep 1995).
51. Krapivinsky, G., Gordon, E. A., Wickman B., Velimirovic, B., Krapivinsky, L., Clapham, D. E. (1995) *Nature* 374:135–141.
52. Krapivinsky, G., Krapivinsky, L., Velimirovic, B., Wickman, K., Navarro, B., Clapham, D. E., (1995b) *J. Biol. Chem.* 270:28777–28779.
53. Kubo, Y., Reuveny, E., Slesinger, P. A., Jan, Y. N., Jan, L. Y. (1993). *Nature* 364:802–806.
54. Masu, Y. et al. (1994) *Nature* 329:21583–21586.
55. Miller, J., Germain, R. N., Efficient cell surface expression of class II MHC molecules in the absence of associated invariant chain. *J. Exp. Med.* 164:1478–1489 (1986).
56. Sambrook, J., Fritsch, E. F., and Maniatis, T., In: Molecular Cloning: A Laboratory Manual, 2nd Edition (Cold Spring Harbor Laboratory, Cold Spring Harbor, N.Y.), 1989.
57. Sanger, F., Nicklen, S. and Coulsen, A. R. *Proc. Natl. Acad. Sci. USA* 74:5463–5467 (1977).
58. Southern, E. M. Detection of specific sequences among DNA fragments separated by gel electrophoresis. *J. Mol. Biol.* 98:503–517 (1975).
59. Spurney, R. F.; Coffman, T. M. *J. Pharmacol. Exp. Ther.* 283(1):207–215 (October 1997).
60. Weinshank, R. L.; Zgombick, J. M.; Macchi, M. J.; Branchek, T. A.; Hartig, P. R. *Proc. Natl. Acad. Sci. U.S.A.* 89(8):3630–3634 (1992).

61. Quick, M. W., Lester, H. A. Methods for expression of excitability proteins in Xenopus oocytes. Meth. Neurosci. 19:261–279 (1994).
62. Smith, K. E., Forray, C., Walker, M. W., Jones, K. A., Tamm, J. A., Bard, J., Branchek, T. A., Linemeyer, D. L., Gerald, C. Expression cloning of a rat hypothalamic galanin receptor coupled to phosphoinositide turnover. J. Biol. Chem. 272:24612–24616 (1997).
63. Salon, J. A. and Owicki, J. A. Real-time measurements of receptor activity: Application of microphysiometric techniques to receptor biology. Methods in Neuroscience 25. Receptor Molecular Biology Ed. S. C. Sealfon, Academic Press, pp. 201–224 (1996).
64. Berridge, M. J., Downes, C. P., Hanley, M. R., Lithium amplifies agonist-dependent phosphatidylinositol responses in brain and salivary glands. Biochem. J. 206: 587–595 (1982).
65. Cullen, B., "Use of eukaryotic expression technology in the functional analysis of cloned genes", *Methods Enzymol.* 152: 685–704 (1987).
66. Bush, et al., "Nerve growth factor potentiates bradykinin-induced calcium influx and release in PC12 cells", *J. Neurochem.* 57: 562–574 (1991).
67. Gundersen, C. B., et al., "Serotonin receptors induced by exogenous messenger RNA in Xenopus oocytes" *Proc. R. Soc. Lond. B. Biol. Sci.* 219(1214): 103–109 (1983).
68. Lazareno, S. and Birdsall, N. J. M., "Pharmacological characterization of acetylcholine stimulated [35S]-GTPgS binding mediated by human muscarinic m1–m4 receptors: antagonist studies", *Br. J. Pharmacology* 109: 1120–1127 (1993).
69. Takahashi, T., et al., "Rat brain serotonin receptors in Xenopus oocytes are coupled by intracellular calcium to endogenous channels." *Proc. Natl. Acad. Sci. USA* 84(14): 5063–5067 (1987).
70. Tian, W., et al., "Determinants of alpha-Adrenergic Receptor Activation of G protein: Evidence for a Pre-coupled Receptor/G protein State." *Molecular Pharmacology* 45: 524–553 (1994).
71. Allard, M, Labrouche, S, Nosjean, A and Laguzzi, R. Machanisms underlying the cardiovascular responses to peripheral administration of NPFF in the rat. *J Pharmacol Exp Ther* 274: 577–583, 1995.
72. Maggi, C A, Furio, M, Santicioli, P, Conte, B and Meli, A. Spinal and supraspinal components of GABAergic inhibition of the micturition reflex in rats. *J Pharmacol Exp Ther* 240: 998–1005, 1987.
73. Morikawa, K, Hashimoto, S, Yamauchi, T, Kato, H, Ito and Y,Gomi, Y. Inhibitory effect of inaperisone hydrochloride (inaperisone), a new centrally acting muscle relaxant, on the micturition reflex. *Eur J Pharmacol* 213: 409–415, 1992.
74. Kivipelto, L., and Panula, P. Immunohistochemical distribution and partial characterization of FLFQPQRFamidelike peptides in the central nervous system of rats. J. Comp. Neurol. 28:269–287, 1989.
75. Kivipelto, L., and Panula, P. Origin and distribution of Neuropeptide-FF-like immunoreactivity in the spinal cord of rats. J. Comp. Neurol. 307:107–119, 1991.
76. Allard, M., Zajac, J. -M., Simonnet, G. Autoradiographic distribution of receptors to FLFQPQRFamide, a morphine-modulating peptide, in rat central nervous system. Neurosci. 49(1):101–116, 1992.
77. Tang, J., Yang, H. -Y., Costa, E. Inhibition of spontaneous and opiate-modified nociception by an endogenous neuropeptine with phe-met-arg-phe-NH$_2$-like immunoreactivity. Proc. Natl. Acad. Sci. USA. 81:5002–5005, 1984.
78. Herman, J. P., Cullinan, W. E. Neurocircuitry of stress: central control of the hypothalamo-pituitary-adrenocortical axis. Trends in Neurosci. 78:3351–3358, 1997.
79. Kavaliers, M., Colwell, D. D. Neuropeptide FF (FLFQPQRFamide) and IgG from neuropeptide FF antiserum affect spatial learning in mice. Neurosci. Lett. 157:75–78, 1993.
80. Aarnisalo, A. A. and Panula, P. Neuropeptide FF-containing efferent projections from the medial hypothalamus of rat: a Phaseolus vulgaris leucoagglutinin study. Neuroscience 5:175–192, 1995.
81. Marco, N. , Stinus, L., Allard, M. , Le Moal, M. , Simonnet, G. Neuropeptide FLFQPQRFamide receptors within the ventral mesencephalon and dopaminergic terminal areas: localization and functional antiopioid involvement. Neuroscience 4(4): 1035–1044, 1995.
82. Burns, C. M., et al. (1996) Neuroscience Abstracts 385.9.
83. Chu, H. , et al. (1996) Neuroscience Abstracts 385.10.
84. Underwood, D. J., et al. (1994) "Structural Model of Antagonist and Agonist Binding To The Angiotensin II, AT1 Subtype, G protein Coupled Receptor", *Chem. Biol.* 1(4): 211–21.
85. Muthal, A. V. and Chopde, C. T. Anxiolytic effect of neuropeptide FMRFamide in rats. Neuropeptides. 27: 105–108, 1994.
86. Arima, H., Takashi, M., Kondo, K., Iwasaki, Y. and Oiso, Y. Centrally administered neuropeptide FF inhibits arginine vasopressin release in conscious rats. *Endocrinology*. 137 (5): 1523–1529, 1996.
87. Labrouche, S., Laulin, J. -P., LeMoal, M., Tranu, G. and Simonnet, G. Neuropeptide FF in the rat adrenal gland: presence, distribution and pharmacological effects. J. Neuroendocrinology. 10: 559–565, 1998.
88. Fehmann, H. C., McGreggor, G., Weber, V., Eissele, R., Goke, R., Doke, B. and Arnold, R. The effects of two FMRFamide related peptides (A-18-F-amide and F-8-F-amide; morphine modulating peptides') on the endocrine and exocrine rat pancreas. Neuropeptides. 17: 87–92, 1990.
89. Gicquel, S., Fioramonti, J., Bueno, L. and Zajac, J. -M. Effects of F8Famide analogs on intestinal transit in mice. Peptides. 14: 749–753, 1993.
90. Demichel, P., Rodrigues, J. C., Roquebert, J. and Simonnet, G. NPFF, a FMRF-NH2-like peptide, blocks opiate effects on ileum contractions. Peptides. 14: 1005–1009, 1993.
91. Raffa, R. B. and Jacoby, H. I. FMRFamide enhances acetylcholine-induced contractions of guinea pig ileum. Peptides. 10: 693–695, 1989.

What is claimed is:

1. A process involving competitive binding for identifying a chemical compound which specifically binds to a human NPFF2 receptor which comprises separately contacting cells expressing on their cell surface the human NPFF2 receptor, wherein such cells do not normally express the human NPFF2 receptor, with both the chemical compound and a second chemical compound known to bind to the receptor, and with only the second chemical compound, under conditions suitable for binding of both compounds, and detecting specific binding of the chemical compound to the human NPFF2 receptor, a decrease in the binding of the second chemical compound to the human NPFF2 receptor in the presence of the chemical compound indicating that the chemical compound binds to the human NPFF2 receptor, wherein the human NPFF2 receptor has an amino acid sequence identical to the amino acid sequence shown in FIG. 8 (SEQ ID NO: 6) or that encoded by plasmid pCDNA3.1-hNPFF2b (ATCC Accession No. 203255).

2. A process involving competitive binding for identifying a chemical compound which specifically binds to a human NPFF2 receptor which comprises separately contacting a membrane preparation from cells expressing on their cell surface the human NPFF2 receptor, wherein such cells do not normally express the human NPFF2 receptor, with both the chemical compound and a second chemical compound known to bind to the receptor, and with only the second chemical compound, under conditions suitable for binding of both compounds, and detecting specific binding of the chemical compound to the human NPFF2 receptor, a decrease in the binding of the second chemical compound to the human NPFF2 receptor in the presence of the chemical compound indicating that the chemical compound binds to the human NPFF2 receptor, wherein the human NPFF2 receptor has an amino acid sequence identical to the amino acid sequence shown in FIG. 8 (SEO ID NO: 6) or that encoded by plasmid pCDNA3.1-hNPFF2b (ATCC Accession No. 203255).

3. The process of claim 1 or 2, wherein the cell is an insect cell.

4. The process of claim 1 or 2, wherein the cell is a mammalian cell.

5. The process of claim 4, wherein the cell is nonneuronal in origin.

6. The process of claim 5, wherein the nonneuronal cell is a COS-7 cell, 293 human embryonic kidney cell, a CHO cell, a NIH-3T3 cell, a mouse Y1 cell, or a LM(tk−) cell.

7. The process of claim 6, wherein the compound is not previously known to bind to a human NPFF2 receptor.

8. A method of screening a plurality of chemical compounds not known to bind to a human NPFF2 receptor to identify a compound which specifically binds to the human NPFF2 receptor, which comprises (a) contacting cells transfected with and expressing DNA encoding the human NPFF2 receptor with a compound known to bind specifically to the human NPFF2 receptor;

(b) contacting the cells of step (a) with the plurality of compounds not known to bind specifically to the human NPFF2 receptor, under conditions permitting binding of compounds known to bind to the human NPFF2 receptor;

(c) determining whether the binding of the compound known to bind to the human NPFF2 receptor is reduced in the presence of any compound within the plurality of compounds, relative to the binding of the compound in the absence of the plurality of compounds; and if so (d) separately determining the binding to the human NPFF2 receptor of compounds included in the plurality of compounds, so as to thereby identify the compound which specifically binds to the human NPFF2 receptor; wherein the human NPFF2 receptor has an amino acid sequence identical to the amino acid sequence shown in FIG. 8 (SEO ID NO: 6) or that encoded by plasmid pCDNA3.1-hNPFF2b (ATCC Accession No. 203255).

9. A method of screening a plurality of chemical compounds not known to bind to a human NPFF2 receptor to identify a compound which specifically binds to the human NPFF2 receptor, which comprises (a) contacting a membrane preparation from cells transfected with and expressing DNA encoding the human NPFF2 receptor with the plurality of compounds not known to bind specifically to the human NPFF2 receptor under conditions permitting binding of compounds known to bind to the human NPFF2 receptor;

(b) determining whether the binding of a compound known to bind to the human NPFF2 receptor is reduced in the presence of any compound within the plurality of compounds, relative to the binding of the compound in the absence of the plurality of compounds; and if so (c) separately determining the binding to the human NPFF2 receptor of compounds included in the plurality of compounds, so as to thereby identify the compound which specifically binds to the human NPFF2 receptor;

wherein the human NPFF2 receptor has an amino acid sequence identical to the amino acid sequence shown in FIG. 8 (SEQ ID NO: 6) or that encoded by plasmid QCDNA3.1-hNPFF2b (ATCC Accession No. 203255).

10. A method of claim 8 or 9, wherein the cell is a mammalian cell.

11. A method of claim 10, wherein the mammalian cell is non-neuronal in origin.

12. The method of claim 11, wherein the non-neuronal cell is a COS-7 cell, a 293 human embryonic kidney cell, a LM(tk−) cell, a CHO cell, a mouse Y1 cell, or an NIH-3T3 cell.

13. A process for determining whether a chemical compound specifically binds to and inhibits activation of a human NPFF2 receptor, which comprises separately contacting cells producing a second messenger response and expressing on their cell surface the human NPFF2 receptor, wherein such cells do not normally express the human NPFF2 receptor, with both the chemical compound and a second chemical compound known to activate the human NPFF2 receptor, and with only the second chemical compound, under conditions suitable for activation of the human NPFF2 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the human NPFF2 receptor, wherein the human NPFF2 receptor has an amino acid sequence identical to the amino acid sequence shown in FIG. 8 (SEQ ID NO: 6) or that encoded by plasmid pCDNA3.1-hNPFF2b (ATCC Accession No. 203255).

14. The process of claim 13, wherein the second messenger response comprises chloride channel activation and the change in second messenger response is a smaller increase in the level of inward chloride current in the presence of both the chemical compound and the second chemical compound than in the presence of only the second chemical compound.

15. The process of claim 13 or 14, wherein the cell is an insect cell.

16. The process of claim 13 or 14, wherein the cell is a mammalian cell.

17. The process of claim 16, wherein the mammalian cell is nonneuronal in origin.

18. The process of claim 17, wherein the nonneuronal cell is a COS-7 cell, CHO cell, 293 human embryonic kidney cell, NIH-3T3 cell or LM(tk−) cell.

19. The process of claim 13 or 14, wherein the compound is not previously known to bind to a human NPFF2 receptor.

20. A method of screening a plurality of chemical compounds not known to inhibit the activation of a human NPFF2 receptor to identify a compound which inhibits the activation of the human NPFF2 receptor, which comprises:

(a) contacting cells transfected with and expressing the human NPFF2 receptor with the plurality of compounds in the presence of a known human NPFF2 receptor agonist, under conditions permitting activation of the human NPFF2 receptor;

(b) determining whether the activation of the human NPFF2 receptor is reduced in the presence of the plurality of compounds, relative to the activation of the human NPFF2 receptor in the absence of the plurality of compounds; and if so (c) separately determining the inhibition of activation of the human NPFF2 receptor for each compound included in the plurality of compounds, so as to thereby identify the compound which inhibits the activation of the human NPFF2 receptor;

wherein the human NPFF2 receptor has an amino acid sequence identical to the amino acid sequence shown in FIG. 8 (SEQ ID NO: 6) or that encoded by plasmid pCDNA3.1-hNPFF2b (ATCC Accession No. 203255).

21. A method of claim 20, wherein the cell is a mammalian cell.

22. A method of claim 21, wherein the mammalian cell is non-neuronal in origin.

23. The method of claim 22, wherein the non-neuronal cell is a COS-7 cell, a 293 human embryonic kidney cell, a LM(tk−) cell or an NIH-3T3 cell.

* * * * *

SEQUENCE LISTING

<160> NUMBER OF SEQ ID NOS: 71

<210> SEQ ID NO 1
<211> LENGTH: 1410
<212> TYPE: DNA
<213> ORGANISM: Rattus norvegicus

<400> SEQUENCE: 1

| | | | | | |
|---|---|---|---|---|---|
| acccttcctg | ggccccagtc | tacccgcttg | aaggtgcccg | cctcctttgg | agagtgtccc | 60 |
| ggagcagaca | gtatggaggc | ggagccctcc | cagcctccca | acggcagctg | gcccctgggt | 120 |
| cagaacggga | gtgatgtgga | gaccagcatg | gcaaccagcc | tcaccttctc | ctcctactac | 180 |
| caacactcct | ctccggtggc | agccatgttc | atcgcggcct | acgtgctcat | cttcctcctc | 240 |
| tgcatggtgg | gcaacaccct | ggtctgcttc | attgtgctca | gaaccggca | catgcgcact | 300 |
| gtcaccaaca | tgtttatcct | caacctggcc | gtcagcgacc | tgctggtggg | catcttctgc | 360 |
| atgcccacaa | cccttgtgga | caaccttatc | actggttggc | cttttgacaa | cgccacatgc | 420 |
| aagatgagcg | gcttggtgca | gggcatgtcc | gtgtctgcat | cggttttcac | actggtggcc | 480 |
| atcgctgtgg | aaaggttccg | ctgcatcgtg | caccctttcc | gcgagaagct | gacccttcgg | 540 |
| aaggcgctgt | tcaccatcgc | ggtgatctgg | gctctggcgc | tgctcatcat | gtgtccctcg | 600 |
| gcggtcactc | tgacagtcac | ccgagaggag | catcacttca | tgctggatgc | tcgtaaccgc | 660 |
| tcctacccgc | tctactcgtg | ctgggaggcc | tggcccgaga | agggcatgcg | caaggtctac | 720 |
| accgcggtgc | tcttcgcgca | catctacctg | gtgccgctgg | cgctcatcgt | agtgatgtac | 780 |
| gtgcgcatcg | cgcgcaagct | atgccaggcc | cccggtcctg | cgcgcgacac | ggaggaggcg | 840 |
| gtggccgagg | gtggccgcac | ttcgcgccgt | agggcccgcg | tggtgcacat | gctggtcatg | 900 |
| gtgcgctct | tcttcacgtt | gtcctggctg | ccactctggg | tgctgctgct | gctcatcgac | 960 |
| tatgggagc | tgagcgagct | gcaactgcac | ctgctgtcgg | tctacgcctt | ccccttggca | 1020 |
| cactggctgg | ccttcttcca | cagcagcgcc | aaccccatca | tctacggcta | cttcaacgag | 1080 |
| aacttccgcc | gcggcttcca | ggctgccttc | cgtgcacagc | tctgctggcc | tccctgggcc | 1140 |
| gcccacaagc | aagcctactc | ggagcggcc | aaccgcctcc | tgcgcaggcg | ggtggtggtg | 1200 |
| gacgtgcaac | ccagcgactc | cggcctgcca | tcagagtctg | gccccagcag | cggggtccca | 1260 |
| gggcctggcc | ggctgccact | cgcaatggg | cgtgtggccc | atcaggatgg | cccgggggaa | 1320 |
| gggccaggct | gcaaccacat | gcccctcacc | atcccggcct | ggaacatttg | aggtggtcca | 1380 |
| gagaagggag | ggccagtagt | cctgtggccc | | | 1410 |

<210> SEQ ID NO 2
<211> LENGTH: 432
<212> TYPE: PRT
<213> ORGANISM: Rattus norvegicus

<400> SEQUENCE: 2

Met Glu Ala Glu Pro Ser Gln Pro Pro Asn Gly Ser Trp Pro Leu Gly
 1               5                  10                  15

Gln Asn Gly Ser Asp Val Glu Thr Ser Met Ala Thr Ser Leu Thr Phe
            20                  25                  30

Ser Ser Tyr Tyr Gln His Ser Ser Pro Val Ala Ala Met Phe Ile Ala
        35                  40                  45

Ala Tyr Val Leu Ile Phe Leu Leu Cys Met Val Gly Asn Thr Leu Val
    50                  55                  60

```
Cys Phe Ile Val Leu Lys Asn Arg His Met Arg Thr Val Thr Asn Met
 65                  70                  75                  80

Phe Ile Leu Asn Leu Ala Val Ser Asp Leu Val Gly Ile Phe Cys
             85                  90                  95

Met Pro Thr Thr Leu Val Asp Asn Leu Ile Thr Gly Trp Pro Phe Asp
            100                 105                 110

Asn Ala Thr Cys Lys Met Ser Gly Leu Val Gln Gly Met Ser Val Ser
            115                 120                 125

Ala Ser Val Phe Thr Leu Val Ala Ile Ala Val Glu Arg Phe Arg Cys
    130                 135                 140

Ile Val His Pro Phe Arg Glu Lys Leu Thr Leu Arg Lys Ala Leu Phe
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His His Phe Met Leu Asp
            180                 185                 190

Ala Arg Asn Arg Ser Tyr Pro Leu Tyr Ser Cys Trp Glu Ala Trp Pro
        195                 200                 205

Glu Lys Gly Met Arg Lys Val Tyr Thr Ala Val Leu Phe Ala His Ile
    210                 215                 220

Tyr Leu Val Pro Leu Ala Leu Ile Val Val Met Tyr Val Arg Ile Ala
225                 230                 235                 240

Arg Lys Leu Cys Gln Ala Pro Gly Pro Ala Arg Asp Thr Glu Glu Ala
                245                 250                 255

Val Ala Glu Gly Gly Arg Thr Ser Arg Arg Ala Arg Val Val His
            260                 265                 270

Met Leu Val Met Val Ala Leu Phe Phe Thr Leu Ser Trp Leu Pro Leu
            275                 280                 285

Trp Val Leu Leu Leu Ile Asp Tyr Gly Glu Leu Ser Glu Leu Gln
    290                 295                 300

Leu His Leu Leu Ser Val Tyr Ala Phe Pro Leu Ala His Trp Leu Ala
305                 310                 315                 320

Phe Phe His Ser Ser Ala Asn Pro Ile Ile Tyr Gly Tyr Phe Asn Glu
                325                 330                 335

Asn Phe Arg Arg Gly Phe Gln Ala Ala Phe Arg Ala Gln Leu Cys Trp
            340                 345                 350

Pro Pro Trp Ala Ala His Lys Gln Ala Tyr Ser Glu Arg Pro Asn Arg
        355                 360                 365

Leu Leu Arg Arg Arg Val Val Val Asp Val Gln Pro Ser Asp Ser Gly
    370                 375                 380

Leu Pro Ser Glu Ser Gly Pro Ser Ser Gly Val Pro Gly Pro Gly Arg
385                 390                 395                 400

Leu Pro Leu Arg Asn Gly Arg Val Ala His Gln Asp Gly Pro Gly Glu
                405                 410                 415

Gly Pro Gly Cys Asn His Met Pro Leu Thr Ile Pro Ala Trp Asn Ile
            420                 425                 430

<210> SEQ ID NO 3
<211> LENGTH: 200
<212> TYPE: DNA
<213> ORGANISM: Homo sapiens

<400> SEQUENCE: 3
gagccctccc agcctcccaa cagcagttgg ccccctaagtc agaatgggac taacactgag      60
```

```
gccaccccgg ctacaaacct caccttctcc tcctactatc agcacacctc ccctgtggcg    120
gccatgttca ttgtggccta tgcgctcatc ttcctgctct gcatggtggg caacaccctg    180
gtctgtttca tcgtgctcaa                                                 200
```

<210> SEQ ID NO 4
<211> LENGTH: 66
<212> TYPE: PRT
<213> ORGANISM: Homo sapiens

<400> SEQUENCE: 4

```
Glu Pro Ser Gln Pro Pro Asn Ser Ser Trp Pro Leu Ser Gln Asn Gly
  1               5                  10                  15

Thr Asn Thr Glu Ala Thr Pro Ala Thr Asn Leu Thr Phe Ser Ser Tyr
                 20                  25                  30

Tyr Gln His Thr Ser Pro Val Ala Ala Met Phe Ile Val Ala Tyr Ala
             35                  40                  45

Leu Ile Phe Leu Leu Cys Met Val Gly Asn Thr Leu Val Cys Phe Ile
         50                  55                  60

Val Leu
 65
```

<210> SEQ ID NO 5
<211> LENGTH: 1302
<212> TYPE: DNA
<213> ORGANISM: Homo sapiens

<400> SEQUENCE: 5

```
gccgacaggg ctcgccggga gaggttcatc atgaatgaga atgggacaca aaactcttca     60
gaaaactggc atcccatctg gaatgtcaat gacacaaagc atcatctgta ctcagatatt    120
aatattacct atgtgaacta ctatcttcac cagcctcaag tggcagcaat cttcattatt    180
tcctactttc tgatcttctt tttgtgcatg atgggaaata ctgtggtttg ctttattgta    240
atgaggaaca aacatatgca cacagtcact aatctcttca tcttaaacct ggccataagt    300
gatttactag ttggcatatt ctgcatgcct ataacactgc tggacaatat tatagcagga    360
tggccatttg gaaacacgat gtgcaagatc agtggattgg tccagggaat atctgtcgca    420
gcttcagtct ttacgttagt tgcaattgct gtagataggt tccagtgtgt ggtctaccct    480
tttaaaccaa agctcactat caagacagcg tttgtcatta ttatgatcat ctgggtccta    540
gccatcacca ttatgtctcc atctgcagta atgttacatg tgcaagaaga aaaatattac    600
cgagtgagac tcaactccca gaataaaacc agtccagtct actggtgccg ggaagactgg    660
ccaaatcagg aaatgaggaa gatctacacc actgtgctgt tgccaacat ctacctggct    720 cccctctccc tcattgtcat catgtatgga aggattggaa tttcactctt cagggctgca    780
gttcctcaca caggcaggaa gaaccaggag cagtggcacg tggtgtccag gaagaagcag    840
aagatcatta agatgctcct gattgtggcc ctgctttta ttctctcatg gctgcccctg    900
tggactctaa tgatgctctc agactacgct gacctttctc caaatgaact gcagatcatc    960
aacatctaca tctacccttt tgcacactgg ctggcattcg gcaacagcag tgtcaatccc   1020
atcatttatg gtttcttcaa cgagaatttc cgccgtggtt tccaagaagc tttccagctc   1080
cagctctgcc aaaaagagc aaagcctatg aagcttatg cctaaaagc taaaagccat   1140 gtgctcataa acacatctaa tcagcttgtc caggaatcta catttcaaaa ccctcatggg   1200
gaaaccttgc tttataggaa aagtgctgaa aaccccaac aggaattagt gatggaagaa   1260
```
ttaaaagaaa ctactaacag cagtgagatt taaaaagagc ta                    1302

<210> SEQ ID NO 6
<211> LENGTH: 420
<212> TYPE: PRT
<213> ORGANISM: Homo sapiens

<400> SEQUENCE: 6

Met Asn Glu Lys Trp Asp Thr Asn Ser Ser Glu Asn Trp His Pro Ile
1               5                   10                  15

Trp Asn Val Asn Asp Thr Lys His His Leu Tyr Ser Asp Ile Asn Ile
                20                  25                  30

Thr Tyr Val Asn Tyr Tyr Leu His Gln Pro Gln Val Ala Ala Ile Phe
            35                  40                  45

Ile Ile Ser Tyr Phe Leu Ile Phe Phe Leu Cys Met Met Gly Asn Thr
        50                  55                  60

Val Val Cys Phe Ile Val Met Arg Asn Lys His Met His Thr Val Thr
65                  70                  75                  80

Asn Leu Phe Ile Leu Asn Leu Ala Ile Ser Asp Leu Leu Val Gly Ile
                85                  90                  95

Phe Cys Met Pro Ile Thr Leu Leu Asp Asn Ile Ile Ala Gly Trp Pro
            100                 105                 110

Phe Gly Asn Thr Met Cys Lys Ile Ser Gly Leu Val Gln Gly Ile Ser
        115                 120                 125

Val Ala Ala Ser Val Phe Thr Leu Val Ala Ile Ala Val Asp Arg Phe
130                 135                 140

Gln Cys Val Val Tyr Pro Phe Lys Pro Lys Leu Thr Ile Lys Thr Ala
145                 150                 155                 160

Phe Val Ile Ile Met Ile Ile Trp Val Leu Ala Ile Thr Ile Met Ser
                165                 170                 175

Pro Ser Ala Val Met Leu His Val Gln Glu Glu Lys Tyr Tyr Arg Val
            180                 185                 190

Arg Leu Asn Ser Gln Asn Lys Thr Ser Pro Val Tyr Trp Cys Arg Glu
        195                 200                 205

Asp Trp Pro Asn Gln Glu Met Arg Lys Ile Tyr Thr Thr Val Leu Phe
210                 215                 220

Ala Asn Ile Tyr Leu Ala Pro Leu Ser Leu Ile Val Ile Met Tyr Gly
225                 230                 235                 240

Arg Ile Gly Ile Ser Leu Phe Arg Ala Ala Val Pro His Thr Gly Arg
                245                 250                 255

Lys Asn Gln Glu Gln Trp His Val Val Ser Arg Lys Lys Gln Lys Ile
            260                 265                 270

Ile Lys Met Leu Leu Ile Val Ala Leu Leu Phe Ile Leu Ser Trp Leu
        275                 280                 285

Pro Leu Trp Thr Leu Met Met Leu Ser Asp Tyr Ala Asp Leu Ser Pro
290                 295                 300

Asn Glu Leu Gln Ile Ile Asn Ile Tyr Ile Tyr Pro Phe Ala His Trp
305                 310                 315                 320

Leu Ala Phe Gly Asn Ser Ser Val Asn Pro Ile Ile Tyr Gly Phe Phe
                325                 330                 335

Asn Glu Asn Phe Arg Arg Gly Phe Gln Glu Ala Phe Gln Leu Gln Leu
            340                 345                 350

Cys Gln Lys Arg Ala Lys Pro Met Glu Ala Tyr Ala Leu Lys Ala Lys
        355                 360                 365

Ser His Val Leu Ile Asn Thr Ser Asn Gln Leu Val Gln Glu Ser Thr
    370                 375                 380

Phe Gln Asn Pro His Gly Glu Thr Leu Leu Tyr Arg Lys Ser Ala Glu
385                 390                 395                 400

Lys Pro Gln Gln Glu Leu Val Met Glu Glu Leu Lys Glu Thr Thr Asn
                405                 410                 415

Ser Ser Glu Ile
        420

<210> SEQ ID NO 7
<211> LENGTH: 1293
<212> TYPE: DNA
<213> ORGANISM: Homo sapiens

<400> SEQUENCE: 7

| | |
|---|---|
| atggagggg agccctccca gcctcccaac agcagttggc ccctaagtca gaatgggact | 60 |
| aacactgagg ccaccccggc tacaaacctc accttctcct cctactatca gcacacctcc | 120 |
| cctgtggcgg ccatgttcat tgtggcctat gcgctcatct tcctgctctg catggtgggc | 180 |
| aacaccctgg tctgtttcat cgtgctcaag aaccggcaca tgcatactgt caccaacatg | 240 |
| ttcatcctca acctggctgt cagtgacctg ctggtgggca tcttctgcat gcccaccacc | 300 |
| cttgtggaca acctcatcac tgggtggccc ttcgacaatg ccacatgcaa gatgagcggc | 360 |
| ttggtgcagg gcatgtctgt gtcggcttcc gttttcacac tggtggccat tgctgtggaa | 420 |
| aggttccgct gcatcgtgca cccttttcgc gagaagctga ccctgcggaa ggcgctcgtc | 480 |
| accatcgccg tcatctgggc cctggcgctg ctcatcatgt gtccctcggc cgtcacgctg | 540 |
| accgtcaccc gtgaggagca ccacttcatg gtggacgccc gcaaccgctc ctaccctctc | 600 |
| tactcctgct gggaggcctg gcccgagaag ggcatgcgca gggtctacac cactgtgctc | 660 |
| ttctcgcaca tctacctggc gccgctggcg ctcatcgtgg tcatgtacgc ccgcatcgcg | 720 |
| cgcaagctct gccaggcccc gggcccggcc ccgggggcg aggaggctgc ggacccgcga | 780 |
| gcatcgcggc gcagagcgcg cgtggtgcac atgctggtca tggtggcgct gttcttcacg | 840 |
| ctgtcctggc tgccgctctg ggcgctgctg ctgctcatcg actacgggca gctcagcgcg | 900 |
| ccgcagctgc acctggtcac cgtctacgcc ttccccttcg cgcactggct ggccttcttc | 960 |
| aacagcagcg ccaaccccat catctacggc tacttcaacg agaacttccg ccgcggcttc | 1020 |
| caggccgcct tccgcgcccg cctctgcccg cgccgtcgg ggagccacaa ggaggcctac | 1080 |
| tccgagcggc ccggcgggct tctgcacagg cgggtcttcg tggtggtgcg gcccagcgac | 1140 |
| tccgggctgc cctctgagtc gggccctagc agtgggcc ccaggccggg ccgcctcccg | 1200 |
| ctgcggaatg ggcgggtggc tcaccacggc ttgcccaggg aagggcctgg ctgctcccac | 1260 |
| ctgccctca ccattccagc ctgggatatc tga | 1293 |

<210> SEQ ID NO 8
<211> LENGTH: 430
<212> TYPE: PRT
<213> ORGANISM: Homo sapiens

<400> SEQUENCE: 8

Met Glu Gly Glu Pro Ser Gln Pro Pro Asn Ser Ser Trp Pro Leu Ser
1               5                   10                  15

Gln Asn Gly Thr Asn Thr Glu Ala Thr Pro Ala Thr Asn Leu Thr Phe
            20                  25                  30

```
Ser Ser Tyr Tyr Gln His Thr Ser Pro Val Ala Ala Met Phe Ile Val
            35                  40                  45

Ala Tyr Ala Leu Ile Phe Leu Leu Cys Met Val Gly Asn Thr Leu Val
    50                  55                  60

Cys Phe Ile Val Leu Lys Asn Arg His Met His Thr Val Thr Asn Met
65                  70                  75                  80

Phe Ile Leu Asn Leu Ala Val Ser Asp Leu Leu Val Gly Ile Phe Cys
                85                  90                  95

Met Pro Thr Thr Leu Val Asp Asn Leu Ile Thr Gly Trp Pro Phe Asp
            100                 105                 110

Asn Ala Thr Cys Lys Met Ser Gly Leu Val Gln Gly Met Ser Val Ser
            115                 120                 125

Ala Ser Val Phe Thr Leu Val Ala Ile Ala Val Glu Arg Phe Arg Cys
            130                 135                 140

Ile Val His Pro Phe Arg Glu Lys Leu Thr Leu Arg Lys Ala Leu Val
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His His Phe Met Val Asp
            180                 185                 190

Ala Arg Asn Arg Ser Tyr Pro Leu Tyr Ser Cys Trp Glu Ala Trp Pro
            195                 200                 205

Glu Lys Gly Met Arg Arg Val Tyr Thr Thr Val Leu Phe Ser His Ile
            210                 215                 220

Tyr Leu Ala Pro Leu Ala Leu Ile Val Val Met Tyr Ala Arg Ile Ala
225                 230                 235                 240

Arg Lys Leu Cys Gln Ala Pro Gly Pro Ala Pro Gly Gly Glu Glu Ala
                245                 250                 255

Ala Asp Pro Arg Ala Ser Arg Arg Ala Arg Val Val His Met Leu
            260                 265                 270

Val Met Val Ala Leu Phe Phe Thr Leu Ser Trp Leu Pro Leu Trp Ala
            275                 280                 285

Leu Leu Leu Leu Ile Asp Tyr Gly Gln Leu Ser Ala Pro Gln Leu His
290                 295                 300

Leu Val Thr Val Tyr Ala Phe Pro Phe Ala His Trp Leu Ala Phe Phe
305                 310                 315                 320

Asn Ser Ser Ala Asn Pro Ile Ile Tyr Gly Tyr Phe Asn Glu Asn Phe
            325                 330                 335

Arg Arg Gly Phe Gln Ala Ala Phe Arg Ala Arg Leu Cys Pro Arg Pro
            340                 345                 350

Ser Gly Ser His Lys Glu Ala Tyr Ser Glu Arg Pro Gly Gly Leu Leu
            355                 360                 365

His Arg Arg Val Phe Val Val Arg Pro Ser Asp Ser Gly Leu Pro
    370                 375                 380

Ser Glu Ser Gly Pro Ser Ser Gly Ala Pro Arg Pro Gly Arg Leu Pro
385                 390                 395                 400

Leu Arg Asn Gly Arg Val Ala His His Gly Leu Pro Arg Glu Gly Pro
                405                 410                 415

Gly Cys Ser His Leu Pro Leu Thr Ile Pro Ala Trp Asp Ile
            420                 425                 430

<210> SEQ ID NO 9
<211> LENGTH: 23
<212> TYPE: DNA
```

```
<213> ORGANISM: Artificial Sequence
<220> FEATURE:
<223> OTHER INFORMATION: Description of Artificial Sequence:
      primer/probe

<400> SEQUENCE: 9
gyntwyrynn tnwsntgght ncc                                        23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 10
avnadngbrw avannanngg rtt                                        23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
ttatgcttcc ggctcgtatg ttgtg                                      25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 12
atgtgctgca aggcgattaa gttggg                                     26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 13
ggtgctgctg ctgctcatcg actatg                                     26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 14
ttggcgctgc tgtggaagaa ggccag                                     26

<210> SEQ ID NO 15
<211> LENGTH: 24
<212> TYPE: DNA
<213> ORGANISM: Artificial Sequence
```

```
<220> FEATURE:
<223> OTHER INFORMATION: Description of Artificial Sequence:
      primer/probe

<400> SEQUENCE: 15
cggtgctctt cgcgcacatc tacc                                              24

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence:
      primer/probe

<400> SEQUENCE: 16
tgccaagggg aaggcgtaga ccgacagcag gtgcagttgc agctcgatca gctccccata       60

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence:
      primer/probe

<400> SEQUENCE: 17
ccacccttgt ggacaacctc atcactgggt ggccttcga caatgccaca tgc               53

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 18
ctgctctgca tggtgggcaa cacc                                              24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      primer/probe

<400> SEQUENCE: 19
gacggcgatg gtgacgagcg c                                                 21

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence:
      primer/probe

<400> SEQUENCE: 20
gtcaccaaca tgttcatcct caacctggct gtcagtgacc tgctggtggg catcttctgc       60
atgcc                                                                   65

<210> SEQ ID NO 21
<211> LENGTH: 24
<212> TYPE: DNA
```

```
<213> ORGANISM: Artificial Sequence
<220> FEATURE:
<223> OTHER INFORMATION: Description of Artificial Sequence:
      primer/probe

<400> SEQUENCE: 21
gcgagaagct gaccctgcgg aagg                                           24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 22
tcgtcaccat cgccgtcatc tggg                                           24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 23
cgtcatctgg gccgagggac acag                                           24

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 24
tgacggcgat ggtgacgagc gcc                                            23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 25
cagcctccca acagcagttg gcc                                            23

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence:
      primer/probe

<400> SEQUENCE: 26
tagcaaggat ccgcatatgg aggggagcc ctccc                                35

<210> SEQ ID NO 27
<211> LENGTH: 36
<212> TYPE: DNA
<213> ORGANISM: Artificial Sequence
```

```
<220> FEATURE:
<223> OTHER INFORMATION: Description of Artificial Sequence:
      primer/probe

<400> SEQUENCE: 27
cttcatgaat tcatcgcctg catgtatctc gtgtcc                              36

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:
      primer/probe

<400> SEQUENCE: 28
cgtgtacggt gggaggtcta tataagcaga g                                   31

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:
      primer/probe

<400> SEQUENCE: 29
ccatcctaat acgactcact atagggc                                        27

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 30
actcactata gggctcgagc ggc                                            23

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 31
tgatagtgag ctttggttta aaaggg                                         26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 32
gaagatctac accactgtgc tgtttg                                         26

<210> SEQ ID NO 33
<211> LENGTH: 25
<212> TYPE: DNA
<213> ORGANISM: Artificial Sequence
<220> FEATURE:
```

<223> OTHER INFORMATION: Description of Artificial Sequence:
      primer/probe

<400> SEQUENCE: 33
aacatctacc tggctcccct ctccc                                              25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 34
ttgtcatcat gtatggaagg attgg                                              25

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 35
gaccacacac tggaacctat ctac                                               24

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 36
gcaattgcaa ctaacgtaaa gactg                                              25

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence:
      primer/probe

<400> SEQUENCE: 37
tagcaaggat ccgaggttca tcatgaatga gaaatgg                                 37

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 38
cttcatgaat tcgcgtagta gagttaggat tatcac                                  36

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:

primer/probe

<400> SEQUENCE: 39
ctcctactac caacactcct ctcc        24

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:
      primer/probe

<400> SEQUENCE: 40
acgggttacg agcatccag        19

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence:
      primer/probe

<400> SEQUENCE: 41
gatcagtgga ttggtccagg gaatatc        27

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 42
ccaggtagat gttggcaaac agcac        25

<210> SEQ ID NO 43
<211> LENGTH: 1334
<212> TYPE: DNA
<213> ORGANISM: Rattus norvegicus

<400> SEQUENCE: 43
agcctctcct ttgataaggt ccaccatggg caagagatgg gactcaaact cttcaggaag        60
ctgggatcac atctggagtg gcaatgacac acagcatcct tggtattcag atatcaacat       120
cacatacatg aactactatc tccaccagcc ccacgtgaca gctgtcttca ttagctccta       180
cttcctgatc ttcttcctgt gcatggtggg aaacactgtc gtttgctttg ttgtaataag       240
gaataggtac atgcacacgg tcactaattt cttcatcttc aacctcgcaa taagtgactt       300
actggttgga atattctgca tgcctatcac attgctggac aacatcatag caggatggcc       360
gtttggaagc agcatgtgca gatcagcgg gctggtgcaa gggatatcgg ttgccgcttc       420
tgtcttcacc ttggttgcca tagccgtaga cagattccgg tgtgtggtct acccctttaa       480
gcccaagctc actgtcaaga cagccttttgt catgatcgtg atcatctggg gcctggccat       540
caccattatg accccatctg caatcatgtt acatgtacag gaagaaaaat actaccgtgt       600
gaggctcagc tcccacaata aaaccagcac agtctactgg tgtcgggagg attggccaaa       660
ccaggaaatg aggaggatct acaccaccgt gctctttgcc actatctacc tggctccact       720
ctccctcatt gttatcatgt atgcaaggat tggggcttcc ctcttcaaga cctcagcaca       780

-continued

```
cagcacaggt aagcagcgcc tggagcagtg gcatgtatcc aagaagaaac agaaggtcat    840
caagatgctg ctgactgtgg ccctcctttt catcctttcc tggcttcccc tgtggactct    900
gatgatgctc tcagactatg ctgacctgtc acctaacaaa ctacgtgtca tcaatattta    960
tgtctaccct tttgcccact ggctcgcctt ctgcaatagc agtgtcaacc ccatcattta   1020
tggtttcttt aatgaaaatt ttcgcagtgg tttccaagat gctttccagt tctgccaaaa   1080
gaaagtcaaa ccccaggaag cctatggcct aagagctaaa cgcaacctgg acataaacac   1140
atctggcctg ttggtccatg aacctgcatc tcaaaaccca gtggggaaa acttgggatg    1200 tagaaaaagt gcagacaatc ccacacagga atccttgatg gaggaaacgg gagaagctac   1260
caacagtact gagacttaga aagatagtat gctatccaat gttatatagc atacgaagcc   1320
aactccgatg gctg                                                    1334
```

<210> SEQ ID NO 44
<211> LENGTH: 417
<212> TYPE: PRT
<213> ORGANISM: Rattus norvegicus

<400> SEQUENCE: 44

```
Met Gly Lys Arg Trp Asp Ser Asn Ser Gly Ser Trp Asp His Ile
  1               5                  10                  15

Trp Ser Gly Asn Asp Thr Gln His Pro Trp Tyr Ser Asp Ile Asn Ile
                 20                  25                  30

Thr Tyr Met Asn Tyr Tyr Leu His Gln Pro His Val Thr Ala Val Phe
             35                  40                  45

Ile Ser Ser Tyr Phe Leu Ile Phe Phe Leu Cys Met Val Gly Asn Thr
         50                  55                  60

Val Val Cys Phe Val Val Ile Arg Asn Arg Tyr Met His Thr Val Thr
 65                  70                  75                  80

Asn Phe Phe Ile Phe Asn Leu Ala Ile Ser Asp Leu Leu Val Gly Ile
                 85                  90                  95

Phe Cys Met Pro Ile Thr Leu Leu Asp Asn Ile Ile Ala Gly Trp Pro
            100                 105                 110

Phe Gly Ser Ser Met Cys Lys Ile Ser Gly Leu Val Gln Gly Ile Ser
        115                 120                 125

Val Ala Ala Ser Val Phe Thr Leu Val Ala Ile Ala Val Asp Arg Phe
130                 135                 140

Arg Cys Val Val Tyr Pro Phe Lys Pro Lys Leu Thr Val Lys Thr Ala
145                 150                 155                 160

Phe Val Met Ile Val Ile Ile Trp Gly Leu Ala Ile Thr Ile Met Thr
                165                 170                 175

Pro Ser Ala Ile Met Leu His Val Gln Glu Glu Lys Tyr Tyr Arg Val
            180                 185                 190

Arg Leu Ser Ser His Asn Lys Thr Ser Thr Val Tyr Trp Cys Arg Glu
        195                 200                 205

Asp Trp Pro Asn Gln Glu Met Arg Arg Ile Tyr Thr Thr Val Leu Phe
210                 215                 220

Ala Thr Ile Tyr Leu Ala Pro Leu Ser Leu Ile Val Ile Met Tyr Ala
225                 230                 235                 240

Arg Ile Gly Ala Ser Leu Phe Lys Thr Ser Ala His Ser Thr Gly Lys
                245                 250                 255

Gln Arg Leu Glu Gln Trp His Val Ser Lys Lys Gln Lys Val Ile
            260                 265                 270
```

```
Lys Met Leu Leu Thr Val Ala Leu Leu Phe Ile Leu Ser Trp Leu Pro
            275                 280                 285

Leu Trp Thr Leu Met Met Leu Ser Asp Tyr Ala Asp Leu Ser Pro Asn
        290                 295                 300

Lys Leu Arg Val Ile Asn Ile Tyr Val Tyr Pro Phe Ala His Trp Leu
305                 310                 315                 320

Ala Phe Cys Asn Ser Ser Val Asn Pro Ile Ile Tyr Gly Phe Phe Asn
            325                 330                 335

Glu Asn Phe Arg Ser Gly Phe Gln Asp Ala Phe Gln Phe Cys Gln Lys
            340                 345                 350

Lys Val Lys Pro Gln Glu Ala Tyr Gly Leu Arg Ala Lys Arg Asn Leu
            355                 360                 365

Asp Ile Asn Thr Ser Gly Leu Leu Val His Glu Pro Ala Ser Gln Asn
            370                 375                 380

Pro Ser Gly Glu Asn Leu Gly Cys Arg Lys Ser Ala Asp Asn Pro Thr
385                 390                 395                 400

Gln Glu Ser Leu Met Glu Glu Thr Gly Glu Ala Thr Asn Ser Thr Glu
                    405                 410                 415

Thr

<210> SEQ ID NO 45
<211> LENGTH: 8
<212> TYPE: PRT
<213> ORGANISM: Rattus norvegicus

<400> SEQUENCE: 45

Phe Leu Phe Gln Pro Gln Arg Phe
  1               5

<210> SEQ ID NO 46
<211> LENGTH: 18
<212> TYPE: PRT
<213> ORGANISM: Rattus norvegicus

<400> SEQUENCE: 46

Ala Gly Glu Gly Leu Ser Ser Pro Phe Trp Ser Leu Ala Ala Pro Gln
  1               5                  10                  15

Arg Phe

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 47
tttgtcatta ttatgatcat ctgg                                      24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 48
aataaaaagc agggccacaa tcag                                      24
```

```
<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 49
tcattatttc ctactttctg atc                                              23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 50
ctcatttcct ggtttggcca atcc                                             24

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 51
tcttcaagac ctcagcacac agc                                              23

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 52
gagctggaaa gcttcttgga aacc                                             24

<210> SEQ ID NO 53
<211> LENGTH: 49
<212> TYPE: DNA
<213> ORGANISM: Artificial Sequence
<220> FEATURE:
<223> OTHER INFORMATION: Description of Artificial Sequence:
      primer/probe

<400> SEQUENCE: 53
ctggtgtcgg gaggattggc caaaccagga aatgaggagg atctacacc                  49

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 54
gcagtgtcaa ccccatcatt tatgg                                            25
```

```
<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 55
caaagcaaac gacagtgttt cccacc                                          26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 56
agtgaccgtg tgcatgtacc tattcc                                          26

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence:
      primer/probe

<400> SEQUENCE: 57
ggtgggaaac actgtcgttt gctttgttgt aataaggaat aggtacatgc acacggtcac     60

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 58
gtcacggatc cagcctctcc tttgataagg tccacc                               36

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence:
      primer/probe

<400> SEQUENCE: 59
gtcagccatc gagttggctt cgtatgctat ataacattgg atagc                     45

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 60
ctggtcaccg tctacgcctt                                                 20

<210> SEQ ID NO 61
```

```
<211> LENGTH: 16
<212> TYPE: DNA
<213> ORGANISM: Artificial Sequence
<220> FEATURE:
<223> OTHER INFORMATION: Description of Artificial Sequence:
      primer/probe

<400> SEQUENCE: 61
ccgcggcgga agttct                                                      16

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence:
      primer/probe

<400> SEQUENCE: 62
acagcagcgc caaccccatc at                                               22

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 63
cctgattgtg gccctgct                                                    18

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 64
catttggaga aaggtcagcg tag                                              23

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 65
ctcatggctg cccctgtgga ctcaat                                           26

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence:
      primer/probe

<400> SEQUENCE: 66
gctgtggaaa ggttccgct                                                   19

<210> SEQ ID NO 67
<211> LENGTH: 17
```

```
<212> TYPE: DNA
<213> ORGANISM: Artificial Sequence
<220> FEATURE:
<223> OTHER INFORMATION: Description of Artificial Sequence:
      primer/probe

<400> SEQUENCE: 67
cgccttccga agggtca                                                    17

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence:
      primer/probe

<400> SEQUENCE: 68
atcgtgcacc ctttccgcga gaa                                             23

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 69
gaggatctac accaccgtgc tatt                                            24

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence:
      primer/probe

<400> SEQUENCE: 70
gaagccccaa tccttgcata c                                               21

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence:
      primer/probe

<400> SEQUENCE: 71
tctacctggc tccactctcc ctcattgtt                                       29
```